United States Patent
Oehlenschlaeger et al.

(10) Patent No.: US 11,407,964 B2
(45) Date of Patent: *Aug. 9, 2022

(54) CLEANING COMPOSITIONS AND USES THEREOF

(71) Applicant: Novozymes A/S, Bagsvaerd (DK)

(72) Inventors: Christian Berg Oehlenschlaeger, Valby (DK); Dorotea Raventos Segura, Rungsted (DK); Jesper Salomon, Holte (DK); Rebecca Munk Vejborg, Allerod (DK)

(73) Assignee: Novozymes A/S, Bagsværd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/500,465

(22) PCT Filed: Apr. 6, 2018

(86) PCT No.: PCT/EP2018/058825
§ 371 (c)(1),
(2) Date: Oct. 3, 2019

(87) PCT Pub. No.: WO2018/185267
PCT Pub. Date: Oct. 11, 2018

(65) Prior Publication Data
US 2020/0190440 A1     Jun. 18, 2020

(30) Foreign Application Priority Data

Apr. 6, 2017    (EP) ...................................... 17165331

(51) Int. Cl.
*C11D 3/386* (2006.01)
(52) U.S. Cl.
CPC .. *C11D 3/38636* (2013.01); *C12Y 301/21001* (2013.01); *C12Y 302/01109* (2013.01)
(58) Field of Classification Search
None
See application file for complete search history.

(56) References Cited

U.S. PATENT DOCUMENTS

| | | | | |
|---|---|---|---|---|
| 10,131,863 B2* | 11/2018 | Gori | ........................ | C12N 15/52 |
| 10,479,981 B2* | 11/2019 | Oestergaard | ............. | C12N 9/22 |
| 2015/0376554 A1 | 12/2015 | Christensen | | |
| 2016/0177279 A1 | 6/2016 | Bauer | | |
| 2017/0152462 A1 | 6/2017 | Baltsen | | |
| 2020/0109353 A1* | 4/2020 | Oehlenschlaeger | ......................... | C11D 17/0039 |

FOREIGN PATENT DOCUMENTS

| | | |
|---|---|---|
| WO | 2009/087523 A2 | 7/2009 |
| WO | 2011098579 A1 | 8/2011 |
| WO | 2012/125937 A2 | 9/2012 |
| WO | 2015/184526 A1 | 12/2015 |
| WO | 2016/066756 A2 | 5/2016 |
| WO | 2016/066757 A2 | 5/2016 |
| WO | 2016/087619 A1 | 6/2016 |
| WO | 2016/135351 A1 | 9/2016 |
| WO | 2016/176240 A1 | 11/2016 |
| WO | 2016/176241 A2 | 11/2016 |
| WO | 2016/176280 A1 | 11/2016 |
| WO | 2016/176282 A1 | 11/2016 |
| WO | 2016/176296 A1 | 11/2016 |
| WO | 2017/059802 A1 | 4/2017 |
| WO | 2017/162836 A1 | 9/2017 |
| WO | 2018/011276 A1 | 1/2018 |

OTHER PUBLICATIONS

Naumoff, D.G., "Hierarchical Classification of Glycoside Hydrolases", Biochemistry (Moscow), vol. 76, No. 6, pp. 622-635. (Year: 2011).*
Millard, UniProt Accession No. A0A0Q4EXK9 (2016).
Abot et al, 2016, BMC Genomics, vol. 17, No. 1, pp. 1-12.
Andrew et al, 2016, Uniprot access No. A0A0Q4EXK9.
Anonymous, 2015, UniProtKB Access No. A0A0k1QM56.
Anonymous, 2017, Uniprot access No. A0A1E4X7D3.
Cerqueira et al, 2013, EBI Accession No. N9CDL3.
Izano et al, 2008, Appl Environ Microbiol, vol. 74, No. 2, pp. 470-476.
Jaros et al, 2017, EBI Accession No. A0A1M5EJD7.
Lavstsen et al, 2017, EBI Accession No. A0A1A8LUE4.
Little et al, 2015, J Biol Chem, vol. 290, No. 37, pp. 22827-22840.
Naumoff, 2011, Mol Biol, vol. 45, No. 6, pp. 983-992.
Naumov et al, 2011, Mol. Biol. vol. 45, No. 4, pp. 703-714.
Rempel, 2016, Glycoside hydrolase family 39—CAZypedia, retrieved from the Internet URL:web.archive.org/web/28168828038338/www.cazypedia.org/index.php/Glycoside Hydrolase Family 39.
Tsaki et al, 2013, EBI Accession No. U3A496.
Yakandawala et al, 2011, Appl Environ Microbiol, vol. 77, No. 23, pp. 8303-8309.
Anonymous, 2013, NCBI Reference sequence WP_017336430.1.
Anonymous, 2017, NCBI Reference sequence WP_029565313.1.

* cited by examiner

*Primary Examiner* — Anand U Desai
(74) *Attorney, Agent, or Firm* — Yoshimi Barron

(57) ABSTRACT

The present invention relates to compositions such as cleaning compositions comprising a mix of enzymes. The invention further relates, use of compositions comprising such enzymes in cleaning processes and/or for deep cleaning of organic soiling, methods for removal or reduction of components of organic matter.

12 Claims, No Drawings

Specification includes a Sequence Listing.

CLEANING COMPOSITIONS AND USES THEREOF

CROSS-REFERENCE TO RELATED APPLICATIONS

This application is a 35 U.S.C. 371 national application of international application no. PCT/EP2018/058825 filed Apr. 6, 2018 which claims priority or the benefit under 35 U.S.C. 119 of European application no. EP 17165331.4 filed Apr. 6, 2017 the contents of which are fully incorporated herein by reference.

REFERENCE TO A SEQUENCE LISTING

This application contains a Sequence Listing in computer readable form, which is incorporated herein by reference.

BACKGROUND OF THE INVENTION

The present invention relates to compositions such as cleaning compositions comprising a mix of enzymes. The invention further relates, use of compositions comprising such enzymes in cleaning processes and/or for deep cleaning of organic soiling, methods for removal or reduction of components of organic matter.

DESCRIPTION OF THE RELATED ART

Enzymes have been used in detergents for decades. Usually a cocktail of various enzymes is added to detergent compositions. The enzyme cocktail often comprises various enzymes, wherein each enzyme targets it specific substrate e.g. amylases are active towards starch stains, proteases on protein stains and so forth. Textiles surface and hard surfaces, such as dishes or the inner space of a laundry machine enduring a number of wash cycles, become soiled with many different types of soiling which may compose of proteins, grease, starch etc. One type of soiling may be organic matter, such as biofilm, EPS, etc. Organic matter composes different molecules such as polysaccharides, extracellular DNA (eDNA), and proteins. Some organic matter composes an extracellular polymeric matrix, which may be sticky or gluing, which when present on textile, attracts soils and may course redeposition or backstaining of soil resulting in a greying of the textile. Additionally, organic matters such as biofilms often cause malodor issue as various malodor molecules can be adhered by the polysaccharides, extracellular DNA (eDNA), and proteins in the complex extracellular matrix and be slowly released out to cause consumer noticeable malodor issue. There is still a need for cleaning compositions, which effectively prevent, reduce or remove components of organic soiling, an effect described in the present application as "deep cleaning". The present invention provides new compositions fulfilling such need.

SUMMARY OF THE INVENTION

The present invention relates to a cleaning composition comprising a DNase, a Glyco_hydro_114 glycosyl hydrolase and a cleaning component. The invention further relates to compositions in particular to cleaning compositions comprising at least 0.001 ppm DNase and at least 0.001 ppm glycosyl hydrolase and a cleaning component, wherein the cleaning component is selected from
 a. 0.1 to 15 wt % of at least one a surfactant;
 b. 0.5 to 20 wt % of at least one builder; and
 c. 0.01 to 10 wt % of at least one bleach component The invention further relates to the use of a composition comprising a DNase, a Glyco_hydro_114 glycosyl hydrolase and a cleaning component for deep cleaning of an item, wherein the item is a textile or a surface. The invention further relates to a method of formulating a cleaning composition comprising adding a DNase, a glycosyl hydrolase, preferably a Glyco_hydro_114 glycosyl hydrolase, and at least one cleaning component. The invention further relates to a kit intended for deep cleaning, wherein the kit comprises a solution of an enzyme mixture comprising a DNase, glycosyl hydrolase, preferably a Glyco_hydro_114 glycosyl hydrolase and optionally a protease. The invention further relates to a method of deep cleaning on an item, comprising the steps of:
 a) contacting the item with a cleaning composition comprising a DNase, a Glyco_hydro_114 glycosyl hydrolase and a cleaning component; and
 b) optionally rinsing the item, wherein the item is preferably a textile.

The invention further relates to a method of deep cleaning of an item, comprising the steps of: a) contacting the item with a solution comprising an enzyme mixture comprising a DNase and a glycosyl hydrolase and optionally a protease; and a cleaning component, wherein the cleaning component is selected from 0.1 to 15 wt % of at least one a surfactant; 0.5 to 20 wt % of at least one builder; and 0.01 to 10 wt % of at least one bleach component; and b) optionally rinsing the item, wherein the item is preferably a textile. The invention also relates to a kit intended for deep cleaning, wherein the kit comprises a solution of an enzyme mixture comprising a DNase and a Glyco_hydro_114 glycosyl hydrolase.

DETAILED DESCRIPTION OF THE INVENTION

Various enzymes are applied in cleaning processes each targeting specific types of soiling such as protein, starch and grease soiling. Enzymes are now standard ingredients in detergents for laundry and dish wash. The effectiveness of these commercial enzymes provides detergents which removes much of the soiling. However, organic matters such as EPS (extracellular polymeric substance) comprised in much biofilm constitute a challenging type of soiling due to the complex nature of such organic matters. None of the commercially available cleaning compositions effectively remove or reduce EPS and/or biofilm related soiling e.g. on textiles. Provided here is cleaning compositions comprising at least one DNase, at least one glycosyl hydrolase e.g. a Glyco_hydro_114 glycosyl hydrolase and a cleaning component. Biofilm may be produced when a group of microorganisms' cells stick to each other or stick to a surface, such as a textile, dishware or hard surface or another kind of surface. These adherent cells are frequently embedded within a self-produced matrix of extracellular polymeric substance (EPS), which constitute 50% to 90% of the biofilm's total organic matter. EPS is mostly composed of polysaccharides (exopolysaccharides) and proteins, but include other macro-molecules such as eDNA, lipids and other organic substances. Organic matter like biofilm may be sticky or gluing, which when present on textile, may give rise to redeposition or backstaining of soil resulting in a greying of the textile. Another drawback of organic matter e.g. biofilm is the malodor as various malodor related molecules are often associated with organic matter e.g. biofilm. Further, when dirty laundry items are washed together with less dirty laundry items the dirt present in the wash liquor tend to stick to organic matter e.g. biofilm or biofilm components as a result, hereof the laundry item is more "soiled" after wash than before wash. This effect may also be termed redeposition.

The composition of the invention is preferably a cleaning composition; the composition comprises at least one DNase and at least one glycosyl hydrolase e.g. a Glyco_hydro_114 glycosyl hydrolase. Examples of useful DNases and glycosyl hydrolases are mentioned below in the sections "Polypeptides having DNase activity" and "Polypeptides having glycosyl hydrolase activity" respectively.

The compositions of the invention comprise a blend of a DNase and a glycosyl hydrolase e.g. a Glyco_hydro_114 glycosyl hydrolase are effective in reducing or removing organic components e.g. DNA and polysaccharides.

Enzymes

Polypeptides Having DNase Activity (DNase)

The term "DNase" means a polypeptide with DNase (deoxyribonuclease) activity that catalyzes the hydrolytic cleavage of phosphodiester linkages in a DNA backbone, thus degrading DNA. Exodeoxyribonuclease cut or cleaves residues at the end of the DNA back bone where endodeoxyribonucleases cleaves or cut within the DNA backbone. A DNase may cleave only double-stranded DNA or may cleave double stranded and single stranded DNA. The term "DNases" and the expression "a polypeptide with DNase activity" are used interchangeably throughout the application. For purposes of the present invention, DNase activity is determined according to the procedure described in the Assay I.

Preferably the DNase is selected from any of the enzyme classes E.C.3.1, preferably E.C.3.1.21, e.g. such as E.C.3.1.21.X, where X=1, 2, 3, 4, 5, 6, 7, 8 or 9, or e.g. Deoxyribonuclease I, Deoxyribonuclease IV, Type I site-specific deoxyribonuclease, Type II site-specific deoxyribonuclease, Type III site-specific deoxyribonuclease, CC-preferring endo-deoxyribonuclease, Deoxyribonuclease V, T(4) deoxyribonuclease II, T(4) deoxyribonuclease IV or E.C. 3.1.22.Y where Y=1, 2, 4 or 5, e.g. Deoxyribonuclease II, *Aspergillus* deoxyribonuclease K(1), Crossover junction endo-deoxyribonuclease, Deoxyribonuclease X.

Preferably, the polypeptide having DNase activity is obtained from a microorganism and the DNase is a microbial enzyme. The DNase is preferably of fungal or bacterial origin.

The DNase may be obtainable from *Bacillus* e.g. *Bacillus*, such as a *Bacillus licheniformis, Bacillus subtilis, Bacillus* sp-62451, *Bacillus* sp-18318, *Bacillus horikoshii, Bacillus* sp-62451, *Bacillus* sp-16840, *Bacillus* sp-62668, *Bacillus* sp-13395, *Bacillus horneckiae, Bacillus* sp-11238, *Bacillus cibi, Bacillus idriensis, Bacillus* sp-62520, *Bacillus* sp-16840, *Bacillus* sp-62668, *Bacillus algicola, Bacillus vietnamensis, Bacillus hwajinpoensis, Bacillus indicus, Bacillus marisflavi, Bacillus luciferensis, Bacillus* sp. SA2-6.

The DNase may also be obtained from any of the following *Pyrenochaetopsis* sp; *Vibrissea flavovirens, Setosphaeria rostrate, Endophragmiella valdina, Corynespora cassiicola, Paraphomia* sp. XZ1965, *Monilinia fructicola, Curvularia lunata, Penicillium reticulisporum, Penicillium quercetorum, Setophaeosphaeria* sp., *Alternaria, Alternaria* sp. XZ2545, *Trichoderma reesei, Chaetomium thermophilum, Scytalidium thermophilum, Metapochonia suchlasporia, Daldinia fissa, Acremonium* sp. XZ2007, *Acremonium* sp. XZ2414, *Acremonium dichromosporum, Sarocladium* sp. XZ2014, *Metarhizium* sp. HNA15-2, *Isaria tenuipes Scytalidium circinaturn, Metarhizium lepidiotae, Thermobispora bispora, Sporormia fimetaria, Pycnidiophora* cf. *dispera*, Enviromental sample D, Enviromental sample O, Enviromental sample J, *Clavicipitaceae* sp-70249, *Westerdykella* sp. AS85-2, *Humicolopsis cephalosporioides, Neosartorya massa, Roussoella intermedia, Pleosporales, Phaeosphaeria, Trichoderma harzianum, Aspergillus oryzae, Paenibacillus mucilaginosus* or *Didymosphaeria futilis*.

The DNases to be used in a composition of the invention preferable belong to the NUC1 group of DNases. The NUC1 group of DNases comprises polypeptides which in addition to having DNase activity, may comprise one or more of the motifs [T/D/S][G/N]PQL (SEQ ID NO 69), [F/L/Y/I]A[N/R]D[L/I/P/V] (SEQ ID NO: 70), or C[D/N]T[A/R] (SEQ ID NO: 71). One embodiment of the invention relates to a composition comprising a Glyco_hydro_114 glycosyl hydrolase and polypeptides having DNase activity, wherein the polypeptides comprises one or more of the motifs [T/D/S][G/N]PQL (SEQ ID NO 69), [F/L/Y/I]A[N/R]D[L/I/P/V] (SEQ ID NO: 70) or C[D/N]T[A/R] (SEQ ID NO: 71).

The DNases preferably comprises a NUC1_A domain [D/Q][IN]DH (SEQ ID NO 72). In addition to comprising any of the domain motifs [T/D/S][G/N]PQL, [F/L/Y/I]A[N/R]D[L/I/P/V] or C[D/N]T[A/R] the polypeptides having DNase activity, to be used in a composition of the invention, may comprise the NUC1_A domain and may share the common motif [D/Q][I/V]DH (SEQ ID NO 72). One embodiment the invention relates to compositions comprising a Glyco_hydro_114 glycosyl hydrolase and polypeptides, which comprises one or more motifs selected from the motifs [T/D/S][G/N]PQL, [F/L/Y/I]A[N/R]D[L/I/P/V], C[D/N]T[A/R] and [D/Q][IN]DH, wherein the polypeptides have DNase activity.

The DNases to be added to a composition of the invention preferably belong to the group of DNases comprised in the GYS-clade, which are group of DNases on the same branch of a phylogenetic tree having both structural and functional similarities. These NUC1 and/or NUC1_A DNases comprise the conservative motifs [D/M/L][S/1]GYSR[D/N] (SEQ ID NO: 73) or ASXNRSKG (SEQ ID NO: 74) and share similar structural and functional properties. The DNases of the GYS-clade are preferably obtained from *Bacillus* genus.

One embodiment of the invention relates to a composition comprising a Glyco_hydro_114 glycosyl hydrolase and a polypeptide of the GYS Glade having DNase activity, optionally wherein the polypeptide comprise one or both of the motifs [D/M/L][S/T]GYSR[D/N] (SEQ ID NO: 73), ASXNRSKG (SEQ ID NO: 74) and wherein the polypeptide is selected from the group of polypeptides:

a) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 1, b) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 2, c) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 3, d) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 4,
e) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 5,
f) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 6,
g) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 7,
h) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 8,
i) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 9,
j) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 10,
k) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 11,
l) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 12,
m) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 13,
n) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 14,
o) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 15,
p) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 16,
q) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 17,
r) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 18,
s) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 19,
t) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 20,
u) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 21,
v) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 22,
w) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 23,
x) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 24, and
y) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 25.

Polypeptides having DNase activity and which comprise the GYS-clade motifs have shown particularly good deep cleaning properties e.g. the DNases are particularly effective in removing or reducing components of organic matter, such as biofilm, from an item such as a textile or a hard surface. In addition, these DNases are particularly effective in removing or reducing malodor, from an item such as a textile or a hard surface. Further, the GYS-clade DNases are particularly effective in preventing redeposition when laundering an item such as textile.

In one embodiment the DNases to be added in a composition of the invention preferably belong to the group of DNases comprised in the NAWK-clade, which are NUC1 and NUC1_A DNases, which may further comprise the conservative motifs [V/I]PL[S/A]NAWK (SEQ ID NO: 75) or NPQL (SEQ ID NO: 76).

One embodiment of the invention relates to a composition comprising a Glyco_hydro_114 glycosyl hydrolase and a polypeptide of the NAWK-clade having DNase activity, optionally wherein the polypeptide comprise one or both of the motifs [V/I]PL[S/A]NAWK (SEQ ID NO: 75) or NPQL (SEQ ID NO: 76) and wherein the polypeptide is selected from the group of polypeptides:

a) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 26,
b) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 27,
c) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 28,
d) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 29,
e) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 30,
f) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 31,
g) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 32,
h) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 33,
i) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 34,
j) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 35,
k) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 36,
l) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 37, and
m) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 38.

Polypeptides having DNase activity and which comprise the NAWK-clade motifs have shown particularly good deep cleaning properties e.g. the DNases are particularly effective in removing or reducing components of organic matter, such as biofilm, from an item such as a textile or a hard surface. In addition, these DNases are particularly effective in removing or reducing malodor, from an item such as a textile or a hard surface. Further, the NAWK-clade DNases are particularly effective in preventing redeposition when laundering an item such as textile.

The DNases to be added in a composition of the invention preferably belong to the group of DNases comprised in the KNAW-clade, which are NUC1 and NUC1_A DNases which may further comprise the conservative motifs P[Q/E]L[W/Y] (SEQ ID NO: 77) or [K/H/E]NAW (SEQ ID NO: 78).

One embodiment of the invention relates to a composition comprising a Glyco_hydro_114 glycosyl hydrolase and a polypeptide of the KNAW Glade having DNase activity, optionally wherein the polypeptide comprise one or both of the motifs P[Q/E]L[W/Y] (SEQ ID NO: 77) or [K/H/E]NAW (SEQ ID NO: 78), and wherein the polypeptide is selected from the group of polypeptides:
a) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 39,
b) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 40,
c) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 41,
d) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 42,
e) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 43
f) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 44,
g) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 45,
h) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 46,
i) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 47, j) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 48, k) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 49, l) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 50, and m) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 51.

Polypeptides having DNase activity and which comprise the KNAW-clade motifs have shown particularly good deep cleaning properties e.g. the DNases are particularly effective in removing or reducing components of organic matter, such as biofilm, from an item such as a textile or a hard surface. In addition, these DNases are particularly effective in removing or reducing malodor, from an item such as a textile or a hard surface. Further, the KNAW-clade DNases are particularly effective in preventing redeposition when laundering an item such as textile.

In some embodiments, the present invention relates compositions comprising a Glyco_hydro_114 glycosyl hydrolase and a polypeptide obtainable from *Bacillus* e.g. obtainable from *Bacillus* sp-62451 and having a sequence identity to the polypeptide shown in SEQ ID NO: 1 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 1.

In some embodiments, the present invention relates compositions comprising a Glyco_hydro_114 glycosyl hydrolase and a polypeptide obtainable from *Bacillus* e.g. obtainable from *Bacillus horikoshii* and having a sequence identity to the polypeptide shown in SEQ ID NO: 2 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 2.

In some embodiments, the present invention relates compositions comprising a Glyco_hydro_114 glycosyl hydrolase and a polypeptide obtainable from *Bacillus* e.g. obtainable from *Bacillus* sp-62520 and having a sequence identity to the polypeptide shown in SEQ ID NO: 3 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 3.

In some embodiments, the present invention relates compositions comprising a Glyco_hydro_114 glycosyl hydrolase and a polypeptide obtainable from *Bacillus* e.g. obtainable from *Bacillus* sp-62520 and having a sequence identity to the polypeptide shown in SEQ ID NO: 4 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 4.

In some embodiments, the present invention relates compositions comprising a Glyco_hydro_114 glycosyl hydrolase and a polypeptide obtainable from *Bacillus* e.g. obtainable from *Bacillus horikoshii* and having a sequence identity to the polypeptide shown in SEQ ID NO: 5 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 5.

In some embodiments, the present invention relates compositions comprising a Glyco_hydro_114 glycosyl hydrolase and a polypeptide obtainable from *Bacillus* e.g. obtainable from *Bacillus horikoshii* and having a sequence identity to the polypeptide shown in SEQ ID NO: 6 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 6.

In some embodiments, the present invention relates compositions comprising a Glyco_hydro_114 glycosyl hydrolase and a polypeptide obtainable from *Bacillus* e.g. obtainable from *Bacillus* sp-16840 and having a sequence identity to the polypeptide shown in SEQ ID NO: 7 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 7.

In some embodiments, the present invention relates compositions comprising a Glyco_hydro_114 glycosyl hydrolase and a polypeptide obtainable from *Bacillus* e.g. obtainable from *Bacillus* sp-16840 and having a sequence identity to the polypeptide shown in SEQ ID NO: 8 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 8.

In some embodiments, the present invention relates compositions comprising a Glyco_hydro_114 glycosyl hydrolase and a polypeptide obtainable from *Bacillus* e.g. obtainable from *Bacillus* sp-62668 and having a sequence identity to the polypeptide shown in SEQ ID NO: 9 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 9.

In some embodiments, the present invention relates compositions comprising a Glyco_hydro_114 glycosyl hydrolase and a polypeptide obtainable from *Bacillus* e.g. obtainable from *Bacillus* sp-13395 and having a sequence identity to the polypeptide shown in SEQ ID NO: 10 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 10.

In some embodiments, the present invention relates compositions comprising a Glyco_hydro_114 glycosyl hydrolase and a polypeptide obtainable from *Bacillus* e.g. obtainable from *Bacillus horneckiae* and having a sequence identity to the polypeptide shown in SEQ ID NO: 11 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 11.

In some embodiments, the present invention relates compositions comprising a Glyco_hydro_114 glycosyl hydrolase and a polypeptide obtainable from *Bacillus* e.g. obtainable from *Bacillus* sp-11238 and having a sequence identity to the polypeptide shown in SEQ ID NO: 12 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 12.

In some embodiments, the present invention relates compositions comprising a Glyco_hydro_114 glycosyl hydrolase and a polypeptide obtainable from *Bacillus* e.g. obtainable from *Bacillus cibi* and having a sequence identity to the polypeptide shown in SEQ ID NO: 13 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 13.

In some embodiments, the present invention relates compositions comprising a Glyco_hydro_114 glycosyl hydrolase and a polypeptide obtainable from *Bacillus* e.g. obtainable from *Bacillus* sp-18318 and having a sequence identity to the polypeptide shown in SEQ ID NO: 14 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 14.

In some embodiments, the present invention relates compositions comprising a Glyco_hydro_114 glycosyl hydrolase and a polypeptide obtainable from *Bacillus* e.g. obtainable from *Bacillus idriensis* and having a sequence identity to the polypeptide shown in SEQ ID NO: 15 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 15.

In some embodiments, the present invention relates compositions comprising a Glyco_hydro_114 glycosyl hydrolase and a polypeptide obtainable from *Bacillus* e.g. obtainable from *Bacillus algicola* having a sequence identity to the polypeptide shown in SEQ ID NO: 16 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 16.

In some embodiments, the present invention relates compositions comprising a Glyco_hydro_114 glycosyl hydrolase and a polypeptide obtainable from Enviromental sample J and having a sequence identity to the polypeptide shown in SEQ ID NO: 17 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 17.

In some embodiments, the present invention relates compositions comprising a Glyco_hydro_114 glycosyl hydrolase and a polypeptide obtainable from *Bacillus* e.g. obtainable from *Bacillus vietnamensis* and having a sequence identity to the polypeptide shown in SEQ ID NO: 18 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 18.

In some embodiments, the present invention relates compositions comprising a Glyco_hydro_114 glycosyl hydrolase and a polypeptide obtainable from *Bacillus* e.g. obtainable from *Bacillus hwajinpoensis* and having a sequence identity to the polypeptide shown in SEQ ID NO: 19 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 19.

In some embodiments, the present invention relates compositions comprising a Glyco_hydro_114 glycosyl hydrolase and a polypeptide obtainable from *Paenibacillus mucilaginosus* and having a sequence identity to the polypeptide shown in SEQ ID NO: 20 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 20.

In some embodiments, the present invention relates compositions comprising a Glyco_hydro_114 glycosyl hydrolase and a polypeptide obtainable from *Bacillus* e.g. obtainable from *Bacillus indicus* and having a sequence identity to the polypeptide shown in SEQ ID NO: 21 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 21.

In some embodiments, the present invention relates compositions comprising a Glyco_hydro_114 glycosyl hydrolase and a polypeptide obtainable from *Bacillus* e.g. obtainable from *Bacillus marisflavi* and having a sequence identity to the polypeptide shown in SEQ ID NO: 22 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 22.

In some embodiments, the present invention relates compositions comprising a Glyco_hydro_114 glycosyl hydrolase and a polypeptide obtainable from *Bacillus* e.g. obtainable from *Bacillus luciferensis* and having a sequence identity to the polypeptide shown in SEQ ID NO: 23 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 23.

In some embodiments, the present invention relates compositions comprising a Glyco_hydro_114 glycosyl hydrolase and a polypeptide obtainable from *Bacillus* e.g. obtainable from *Bacillus marisflavi* and having a sequence identity to the polypeptide shown in SEQ ID NO: 24 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 24.

In some embodiments, the present invention relates compositions comprising a Glyco_hydro_114 glycosyl hydrolase and a polypeptide obtainable from *Bacillus* e.g. obtainable from *Bacillus* sp. SA2-6 and having a sequence identity to the polypeptide shown in SEQ ID NO: 25 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 25.

In some embodiments, the present invention relates compositions comprising a Glyco_hydro_114 glycosyl hydrolase and a polypeptide obtainable from *Pyrenochaetopsis* sp. and having a sequence identity to the polypeptide shown in SEQ ID NO: 26 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 26.

In some embodiments, the present invention relates compositions comprising a Glyco_hydro_114 glycosyl hydrolase and a polypeptide obtainable from *Vibrissea flavovirens* and having a sequence identity to the polypeptide shown in SEQ ID NO: 27 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 27.

In some embodiments, the present invention relates compositions comprising a Glyco_hydro_114 glycosyl hydrolase and a polypeptide obtainable from *Setosphaeria rostrate* and having a sequence identity to the polypeptide shown in SEQ ID NO: 28 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 28.

In some embodiments, the present invention relates compositions comprising a Glyco_hydro_114 glycosyl hydrolase and a polypeptide obtainable from *Endophragmiella valdina* and having a sequence identity to the polypeptide shown in SEQ ID NO: 29 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 29.

In some embodiments, the present invention relates compositions comprising a Glyco_hydro_114 glycosyl hydrolase and a polypeptide obtainable from *Corynespora cassiicola* and having a sequence identity to the polypeptide shown in SEQ ID NO: 30 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 30.

In some embodiments, the present invention relates compositions comprising a Glyco_hydro_114 glycosyl hydrolase and a polypeptide obtainable from *Paraphoma* sp. XZ1965 and having a sequence identity to the polypeptide shown in SEQ ID NO: 31 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 31.

In some embodiments, the present invention relates compositions comprising a Glyco_hydro_114 glycosyl hydrolase and a polypeptide obtainable from *Monilinia fructicola* and having a sequence identity to the polypeptide shown in SEQ ID NO: 32 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 32.

In some embodiments, the present invention relates compositions comprising a Glyco_hydro_114 glycosyl hydrolase and a polypeptide obtainable from *Curvularia lunata* and having a sequence identity to the polypeptide shown in SEQ ID NO: 33 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 33.

In some embodiments, the present invention relates compositions comprising a Glyco_hydro_114 glycosyl hydrolase and a polypeptide obtainable from *Penicillium reticulisporum* and having a sequence identity to the polypeptide shown in SEQ ID NO: 34 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 34.

In some embodiments, the present invention relates compositions comprising a Glyco_hydro_114 glycosyl hydrolase and a polypeptide obtainable from *Penicillium quercetorum* and having a sequence identity to the polypeptide shown in SEQ ID NO: 35 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 35.

In some embodiments, the present invention relates compositions comprising a Glyco_hydro_114 glycosyl hydrolase and a polypeptide obtainable from *Setophaeosphaeria* sp. and having a sequence identity to the polypeptide shown in SEQ ID NO: 36 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 36.

In some embodiments, the present invention relates compositions comprising a Glyco_hydro_114 glycosyl hydrolase and a polypeptide obtainable from *Alternaria* sp. XZ2545 and having a sequence identity to the polypeptide shown in SEQ ID NO: 37 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 37.

In some embodiments, the present invention relates compositions comprising a Glyco_hydro_114 glycosyl hydrolase and a polypeptide obtainable from *Alternaria* and having a sequence identity to the polypeptide shown in SEQ ID NO: 38 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 38.

In some embodiments, the present invention relates compositions comprising a Glyco_hydro_114 glycosyl hydrolase and a polypeptide obtainable from *Trichoderma reesei* and having a sequence identity to the polypeptide shown in SEQ ID NO: 39 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 39.

In some embodiments, the present invention relates compositions comprising a Glyco_hydro_114 glycosyl hydrolase and a polypeptide obtainable from *Chaetomium thermophilum* and having a sequence identity to the polypeptide shown in SEQ ID NO: 40 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 40.

In some embodiments, the present invention relates compositions comprising a Glyco_hydro_114 glycosyl hydrolase and a polypeptide obtainable from *Scytalidium thermophilum* and having a sequence identity to the polypeptide shown in SEQ ID NO: 41 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 41.

In some embodiments, the present invention relates compositions comprising a Glyco_hydro_114 glycosyl hydrolase and a polypeptide obtainable from *Metapochonia suchlasporia* and having a sequence identity to the polypeptide shown in SEQ ID NO: 42 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 42.

In some embodiments, the present invention relates compositions comprising a Glyco_hydro_114 glycosyl hydrolase and a polypeptide obtainable from *Daldinia fissa* and having a sequence identity to the polypeptide shown in SEQ ID NO: 43 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 43.

In some embodiments, the present invention relates compositions comprising a Glyco_hydro_114 glycosyl hydrolase and a polypeptide obtainable from *Acremonium* sp. XZ2007 and having a sequence identity to the polypeptide shown in SEQ ID NO: 44 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 44.

In some embodiments, the present invention relates compositions comprising a Glyco_hydro_114 glycosyl hydrolase and a polypeptide obtainable from *Acremonium dichromosporum* and having a sequence identity to the polypeptide shown in SEQ ID NO: 45 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 45.

In some embodiments, the present invention relates compositions comprising a Glyco_hydro_114 glycosyl hydrolase and a polypeptide obtainable from *Sarocladium* sp. XZ2014 and having a sequence identity to the polypeptide shown in SEQ ID NO: 46 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 46.

In some embodiments, the present invention relates compositions comprising a Glyco_hydro_114 glycosyl hydrolase and a polypeptide obtainable from *Metarhizium* sp. HNA15-2 and having a sequence identity to the polypeptide shown in SEQ ID NO: 47 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 47.

In some embodiments, the present invention relates compositions comprising a Glyco_hydro_114 glycosyl hydrolase and a polypeptide obtainable from *Acremonium* sp. XZ2414 and having a sequence identity to the polypeptide shown in SEQ ID NO: 48 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 48.

In some embodiments, the present invention relates compositions comprising a Glyco_hydro_114 glycosyl hydrolase and a polypeptide obtainable from *Isaria tenuipes* and having a sequence identity to the polypeptide shown in SEQ ID NO: 49 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 49.

In some embodiments, the present invention relates compositions comprising a Glyco_hydro_114 glycosyl hydrolase and a polypeptide obtainable from *Scytalidium circinatum* and having a sequence identity to the polypeptide shown in SEQ ID NO: 50 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 50.

In some embodiments, the present invention relates compositions comprising a Glyco_hydro_114 glycosyl hydrolase and a polypeptide obtainable from *Metarhizium lepidiotae* and having a sequence identity to the polypeptide shown in SEQ ID NO: 51 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 51.

In some embodiments, the present invention relates compositions comprising a Glyco_hydro_114 glycosyl hydrolase and a polypeptide obtainable from *Thermobispora bispora* and having a sequence identity to the polypeptide shown in SEQ ID NO: 52 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 52.

In some embodiments, the present invention relates compositions comprising a Glyco_hydro_114 glycosyl hydrolase and a polypeptide obtainable from *Sporormia fimetaria* and having a sequence identity to the polypeptide shown in SEQ ID NO: 53 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 53.

In some embodiments, the present invention relates compositions comprising a Glyco_hydro_114 glycosyl hydrolase and a polypeptide obtainable from *Pycnidiophora* cf. *dispera* and having a sequence identity to the polypeptide shown in SEQ ID NO: 54 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 54.

In some embodiments, the present invention relates compositions comprising a Glyco_hydro_114 glycosyl hydrolase and a polypeptide obtainable from Environmental sample D and having a sequence identity to the polypeptide shown in SEQ ID NO: 55 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 55.

In some embodiments, the present invention relates compositions comprising a Glyco_hydro_114 glycosyl hydrolase and a polypeptide obtainable from Environmental sample 0 and having a sequence identity to the polypeptide shown in SEQ ID NO: 56 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 56.

In some embodiments, the present invention relates compositions comprising a Glyco_hydro_114 glycosyl hydrolase and a polypeptide obtainable from *Clavicipitaceae* sp-70249 and having a sequence identity to the polypeptide shown in SEQ ID NO: 57 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 57.

In some embodiments, the present invention relates compositions comprising a Glyco_hydro_114 glycosyl hydrolase and a polypeptide obtainable from *Westerdykella* sp. AS85-2 and having a sequence identity to the polypeptide shown in SEQ ID NO: 58 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 58.

In some embodiments, the present invention relates compositions comprising a Glyco_hydro_114 glycosyl hydrolase and a polypeptide obtainable from *Humicolopsis cephalosporioides* and having a sequence identity to the polypeptide shown in SEQ ID NO: 59 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 59.

In some embodiments, the present invention relates compositions comprising a Glyco_hydro_114 glycosyl hydrolase and a polypeptide obtainable from *Neosartorya massa* and having a sequence identity to the polypeptide shown in SEQ ID NO: 60 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 60.

In some embodiments, the present invention relates compositions comprising a Glyco_hydro_114 glycosyl hydrolase and a polypeptide obtainable from *Roussoella intermedia* and having a sequence identity to the polypeptide shown in SEQ ID NO: 61 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 61.

In some embodiments, the present invention relates compositions comprising a Glyco_hydro_114 glycosyl hydrolase and a polypeptide obtainable from Pleosporales and having a sequence identity to the polypeptide shown in SEQ ID NO: 62 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 62.

In some embodiments, the present invention relates compositions comprising a Glyco_hydro_114 glycosyl hydrolase and a polypeptide obtainable from *Phaeosphaeria* and having a sequence identity to the polypeptide shown in SEQ ID NO: 63 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 63.

In some embodiments, the present invention relates compositions comprising a Glyco_hydro_114 glycosyl hydrolase and a polypeptide obtainable from *Didymosphaeria futilis* and having a sequence identity to the polypeptide shown in SEQ ID NO: 64 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 64.

In some embodiments, the present invention relates compositions comprising a Glyco_hydro_114 glycosyl hydrolase and a polypeptide obtainable from *Bacillus* e.g. obtainable from *Bacillus licheniformis* having a sequence identity to the polypeptide shown in SEQ ID NO: 65 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 65.

In some embodiments, the present invention relates compositions comprising a Glyco_hydro_114 glycosyl hydrolase and a polypeptide obtainable from *Bacillus* e.g. obtainable from *Bacillus subtilis* having a sequence identity to the polypeptide shown in SEQ ID NO: 66 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 66.

In some embodiments, the present invention relates compositions comprising a Glyco_hydro_114 glycosyl hydrolase and a polypeptide obtainable from *Aspergillus* e.g. obtainable from *Aspergillus oryzae* having a sequence identity to the polypeptide shown in SEQ ID NO: 67 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 67.

In some embodiments, the present invention relates compositions comprising a Glyco_hydro_114 glycosyl hydrolase and a polypeptide obtainable from *Trichoderma* e.g. obtainable from *Trichoderma harzianum* having a sequence identity to the polypeptide shown in SEQ ID NO: 68 of at least 60%, e.g., at least 65%, at least 70%, at least 75%, at least 80%, at least 85%, at least 90%, at least 95%, at least 96%, at least 97%, at least 98%, at least 99%, or 100% and which have DNase activity. In one aspect, the polypeptides differ by up to 10 amino acids, e.g., 1, 2, 3, 4, 5, 6, 7, 8, 9, or 10, from the mature polypeptide shown in SEQ ID NO: 68.

The DNases above may be combined with any of the glycosyl hydrolases below to form a blend to be added to a composition according to the invention.

Polypeptides Having Glycosyl Hydrolase Activity (Glycosyl Hydrolase)

Glycosyl hydrolases (EC 3.2.1.-), which are a widespread group of enzymes that hydrolyse the glyosidic bond between two or more carbohydrates or between a carbohydrate and a non-carbohydrate moiety. A classification of glycoside hydrolases in families based on amino acid sequence similarities has been proposed. The polypeptides to be combined with a DNase and formulated into a detergent composition of the invention comprise at least one glycosyl hydrolase domain and are in the present context defined as glycosyl hydrolases. Thus, polypeptides of the invention hydrolyse glyosidic bonds and the polypeptide of the invention have hydrolytic activity. The glycosyl hydrolase domain comprised in the polypeptide of the invention may be classified as a Glyco_hydro_114 (Pfam domain id PF03537, Pfam version 31.0 Finn (2016). Nucleic Acids Research, Database Issue 44:D279-D285). The polypeptides of the invention may further comprise a polysaccharide deacetylase domain (CE4) and in a preferred embodiment the polypeptides of the invention have hydrolytic and/or deacetylase activity. Polypeptides according to the invention having hydrolytic and/or deacetylase activity includes Glyco_hydro_114 glycosyl hydrolases. A Glyco_hydro_114 glycosyl hydrolase is in the context of the present invention a glycosyl hydrolase comprising glycosyl hydrolase domain (DUF297), which here is termed Glyco_hydro_114 (Pfam domain id PF03537, Pfam version 31.0 Finn (2016). The polypeptides of the invention are glycosyl hydrolases preferably Glyco_hydro_114 glycosyl hydrolases. In one preferred embodiment, the polypeptides of the invention are endo-alpha-1,4-polygalactosaminidases. The polypeptides of the invention have at least hydrolytic activity to glyosidic bond and may also have deacetylase activity. In the context of the present invention the Glyco_hydro_114 glycosyl hydrolase is a PelA enzyme, which is active towards the polysaccharide pel, present in many biofilms. The pellicle (pel) polysaccharide is synthesized e.g. by *Pseudomonas aeruginosa* and is an important biofilm constituent critical for bacterial virulence and persistence. Pel is a cationic polymer composed of partially acetylated 1→4 glycosidic linkages of N-acetylgalactosamine and N-acetylglucosamine that promotes cell-cell interactions within the biofilm matrix through electrostatic interactions with extracellular DNA (Jennings et al. PNAS September 2015, vol. 112, no 36, 11353-11358; Marmont et. al. J Biol Chem. 2017 Nov. 24; 292(47):19411-19422. 2017). The glycosyl hydrolases to be incorporated with a DNase in a composition according to the invention preferably belongs to the Glyco_hydro_114 pFam domain (PF03537) family. The glycosyl hydrolases to be incorporated in a composition of the invention preferably comprise a domain termed here as CE4_PelA_like domain, which polypeptides are represented by a protein PelA that is encoded by a gene in the pelA-G gene cluster for pellicle production and biofilm formation in *Pseudomonas aeruginosa*. PelA and most of the family members contain a domain of unknown function, DUF297 (PF03537). The glycosyl hyrdrolases are preferably PelA homologues.

The glycosyl hydrolase may be obtainable from *Pseudomonas* protegenes Pf-5, *Pseudomonas aeruginosa* or *Geobacter metallireducens*. Preferably the glycosyl hydrolases to be combined with a DNase of the invention are any of those shown in table 1.

TABLE 1

| PelA | *Pseudomonas protegenes* Pf-5 | GenBank: AAY92244 |
| PelA | *Pseudomonas aeruginosa* | GenBank: AAG06452 |
| PelA | *Geobacter metallireducens* | GenBank: ABB32191 |

In one embodiment of the invention relates to a composition comprising a DNase and a glycosyl hydrolase, wherein the glycosyl hydrolase is glycosyl hydrolase comprising a Glyco_hydro_114 domain and a cleaning component The glycosyl hydrolases to be combined with a DNase in a composition according to the invention comprises a GH domain which may be classified as a Glyco_hydro_114 domain and in a preferred embodiment the polypeptides have hydrolytic (EC 3.2.1.) activity (as described at www.cazy.org). The polypeptides comprising the Glyco_hydro_114 domain are preferably homologues of PelA enzymes, which are proteins that degrade the exopolysaccharide Pel. In one embodiment, the glycosyl hydrolase is a glycosyl hydrolase comprising the domain Glyco_hydro_114 glycosyl preferably obtained from *Pseudomonas* such as *Pseudomonas* sp-62208, *Pseudomonas seleniipraecipitans*, *Pseudomonas migulae*, *Pseudomonas corrugate*, *Pseudomonas pelagia*, *Pseudomonas aeruginosa*, *Pseudomonas composti*. The Glyco_hydro_114 glycosyl hydrolase is preferably obtained from *Myxococcus* such as *Myxococcus macrosporus*, *Myxococcus virescens*, *Myxococcus fulvus* *Myxococcus stipitatus*. The Glyco_hydro_114 glycosyl hydrolase may also preferably be obtained from any of the following organisms: *Thermus rehai*, *Burkholderia* sp-63093, *Gallaecimonas pentaromativorans*, *Nonomuraea coxensis*, *Glycomyces rutgersensis*, *Paraburkholderia phenazinium*, *Streptomyces griseofuscus*, *Lysinibacillus xylanilyticus*, *Tumebacillus ginsengisoli*, *Lysinibacillus boronitolerans*, *Microbulbifer hydrolyticus*, *Carnobacterium inhibens* subsp.

In one embodiment, the invention relates to a composition comprising a DNase, a glycosyl hydrolase, wherein the glycosyl hydrolase comprises the Glyco_hydro_114 glycosyl hydrolase domain, and a cleaning component The glycosyl hydrolases preferably comprise one or more or both the motif(s) GX[FY][LYF]D (SEQ ID NO 82) or AYX[SET]XX[EAS] (SEQ ID NO: 83).

One embodiment of the invention relates to a composition comprising a polypeptide having glycosyl hydrolase activity, optionally wherein the polypeptide optionally comprises one or both the motifs GX[FY][LYF]D (SEQ ID NO 82) or AYX[SET]XX[EAS] (SEQ ID NO: 83) and wherein the polypeptide is selected from the group of polypeptides:

a) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 84, b) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 85, c) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 86, d) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 87, e) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, f) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, g) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, h) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, i) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, j) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, k) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, l) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, m) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, n) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, o) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, p) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, q) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, r) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, s) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, t) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, u) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, v) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 105, w) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, x) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, y) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, z) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, aa) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, bb) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, cc) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, dd) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, ee) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and ff) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 115.

In some preferred embodiment of the invention a DNase of the invention is combined with a glycosyl hydrolase wherein the glycosyl hydrolase is any of the following:

In some embodiments, the present invention relates compositions comprising a polypeptide obtainable from *Pseudomonas* sp-62208 and having a sequence identity to the polypeptide shown in SEQ ID NO: 84 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 84.

In some embodiments, the present invention relates compositions comprising a polypeptide obtainable from Environmental bacterial community A and having a sequence identity to the polypeptide shown in SEQ ID NO: 85 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 85.

In some embodiments, the present invention relates compositions comprising a polypeptide obtainable from *Thermus rehai* and having a sequence identity to the polypeptide shown in SEQ ID NO: 86 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 86.

In some embodiments, the present invention relates compositions comprising a polypeptide obtainable from Environmental bacterial community LE and having a sequence identity to the polypeptide shown in SEQ ID NO: 87 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 87.

In some embodiments, the present invention relates compositions comprising a polypeptide obtainable from *Burkholderia* sp-63093 and having a sequence identity to the polypeptide shown in SEQ ID NO: 88 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 88.

In some embodiments, the present invention relates compositions comprising a polypeptide obtainable from *Myxococcus macrosporus* and having a sequence identity to the polypeptide shown in SEQ ID NO: 89 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 89.

In some embodiments, the present invention relates compositions comprising a polypeptide obtainable from *Gallaecimonas pentaromativorans* and having a sequence identity to the polypeptide shown in SEQ ID NO: 90 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 90.

In some embodiments, the present invention relates compositions comprising a polypeptide obtainable from *Nonomuraea coxensis* and having a sequence identity to the polypeptide shown in SEQ ID NO: 91 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 91.

In some embodiments, the present invention relates compositions comprising a polypeptide obtainable from *Glycomyces rutgersensis* and having a sequence identity to the polypeptide shown in SEQ ID NO: 92 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 92.

In some embodiments, the present invention relates compositions comprising a polypeptide obtainable from Environmental bact. community XE and having a sequence identity to the polypeptide shown in SEQ ID NO: 93 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 93.

In some embodiments, the present invention relates compositions comprising a polypeptide obtainable from *Paraburkholderia phenazinium* and having a sequence identity to the polypeptide shown in SEQ ID NO: 94 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 94.

In some embodiments, the present invention relates compositions comprising a polypeptide obtainable from Environmental bacterial community and having a sequence identity to the polypeptide shown in SEQ ID NO: 95 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 95.

In some embodiments, the present invention relates compositions comprising a polypeptide obtainable from *Myxococcus virescens* and having a sequence identity to the polypeptide shown in SEQ ID NO: 96 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 96.

In some embodiments, the present invention relates compositions comprising a polypeptide obtainable from *Myxococcus fulvus* and having a sequence identity to the polypeptide shown in SEQ ID NO: 97 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 97.

In some embodiments, the present invention relates compositions comprising a polypeptide obtainable from *Myxococcus macrosporus* and having a sequence identity to the polypeptide shown in SEQ ID NO: 98 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 98.

In some embodiments, the present invention relates compositions comprising a polypeptide obtainable from *Myxococcus stipitatus* and having a sequence identity to the polypeptide shown in SEQ ID NO: 99 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 99.

In some embodiments, the present invention relates compositions comprising a polypeptide obtainable from *Myxococcus macrosporus* and having a sequence identity to the polypeptide shown in SEQ ID NO: 100 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 100.

In some embodiments, the present invention relates compositions comprising a polypeptide obtainable from *Pseudomonas seleniipraecipitans* and having a sequence identity to the polypeptide shown in SEQ ID NO: 101 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 101.

In some embodiments, the present invention relates compositions comprising a polypeptide obtainable from *Pseudomonas migulae* and having a sequence identity to the polypeptide shown in SEQ ID NO: 102 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 102.

In some embodiments, the present invention relates compositions comprising a polypeptide obtainable from *Pseudomonas corrugate* and having a sequence identity to the polypeptide shown in SEQ ID NO: 103 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 103.

In some embodiments, the present invention relates compositions comprising a polypeptide obtainable from *Pseudomonas pelagia* and having a sequence identity to the polypeptide shown in SEQ ID NO: 104 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 104.

In some embodiments, the present invention relates compositions comprising a polypeptide obtainable from *Pseudomonas aeruginosa* and having a sequence identity to the polypeptide shown in SEQ ID NO: 105 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 105.

In some embodiments, the present invention relates compositions comprising a polypeptide obtainable from *Streptomyces griseofuscus* and having a sequence identity to the polypeptide shown in SEQ ID NO: 106 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 106.

In some embodiments, the present invention relates compositions comprising a polypeptide obtainable from *Lysinibacillus xylanilyticus* and having a sequence identity to the polypeptide shown in SEQ ID NO: 107 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 107.

In some embodiments, the present invention relates compositions comprising a polypeptide obtainable from *Tumebacillus ginsengisoli* and having a sequence identity to the polypeptide shown in SEQ ID NO: 108 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 108.

In some embodiments, the present invention relates compositions comprising a polypeptide obtainable from *Lysinibacillus boronitolerans* and having a sequence identity to the polypeptide shown in SEQ ID NO: 109 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 109.

In some embodiments, the present invention relates compositions comprising a polypeptide obtainable from *Microbulbifer hydrolyticus* and having a sequence identity to the polypeptide shown in SEQ ID NO: 110 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 110.

In some embodiments, the present invention relates compositions comprising a polypeptide obtainable from *Carnobacterium inhibens* subsp. and having a sequence identity to the polypeptide shown in SEQ ID NO: 111 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 111.

In some embodiments, the present invention relates compositions comprising a polypeptide obtainable from environmental bacterial community subsp. and having a sequence identity to the polypeptide shown in SEQ ID NO: 112 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 112.

In some embodiments, the present invention relates compositions comprising a polypeptide obtainable from *Pseudomonas composti* and having a sequence identity to the polypeptide shown in SEQ ID NO: 113 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 113.

In some embodiments, the present invention relates compositions comprising a polypeptide obtainable from *Paraburkholderia phenazinium* and having a sequence identity to the polypeptide shown in SEQ ID NO: 114 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 114.

In some embodiments, the present invention relates compositions comprising a polypeptide obtainable from *Burkholderia* sp-63093 and having a sequence identity to the polypeptide shown in SEQ ID NO: 115 of at least 60%, e.g., at least 65%, at least 70%, at least 75%, at least 80%, at least 85%, at least 90%, at least 95%, at least 96%, at least 97%, at least 98%, at least 99%, or 100% and which have glycosyl hydrolase activity. In one aspect, the polypeptides differ by up to 10 amino acids, e.g., 1, 2, 3, 4, 5, 6, 7, 8, 9, or 10, from the mature polypeptide shown in SEQ ID NO: 115.

A composition comprising:

The invention relates to cleaning compositions e.g. detergent compositions comprising an enzyme combination of the present invention in combination with one or more additional cleaning composition components. The choice of additional components is within the skill of the artisan and includes conventional ingredients, including the exemplary non-limiting components set forth below. An enzyme blend of the current invention comprises a DNase and a glycosyl hydrolase preferably a Glyco_hydro_114 glycosyl hydrolase. One embodiment of the invention relates to a cleaning composition comprising a DNase, a Glyco_hydro_114 glycosyl hydrolase and a cleaning component.

The DNase is preferably microbial, preferably obtained from bacteria or fungi. One embodiment of the invention relates to a cleaning composition comprising a DNase, a Glyco_hydro_114 glycosyl hydrolase and a cleaning component, wherein the DNase is microbial preferably bacteria or fungi.

In one embodiment, the DNase is obtained from bacteria. One embodiment of the invention relates to a cleaning composition comprising a DNase, a Glyco_hydro_114 glycosyl hydrolase and a cleaning component, wherein the DNase is obtained from *Bacillus*, preferably *Bacillus cibi, Bacillus horikoshii, Bacillus licheniformis, Bacillus subtilis, Bacillus horneckiae, Bacillus idriensis, Bacillus algicola, Bacillus vietnamensis, Bacillus hwajinpoensis, Bacillus indicus, Bacillus marisflavi* or *Bacillus luciferensis*.

The Glyco_hydro_114 glycosyl hydrolase is preferably obtained from *Pseudomonas* such as *Pseudomonas* sp-62208, *Pseudomonas seleniipraecipitans, Pseudomonas migulae, Pseudomonas corrugate, Pseudomonas pelagia, Pseudomonas aeruginosa, Pseudomonas composti*. The Glyco_hydro_114 glycosyl hydrolase is preferably obtained from *Myxococcus* such as *Myxococcus macrosporus, Myxococcus virescens, Myxococcus fulvus Myxococcus stipitatus*. The Glyco_hydro_114 glycosyl hydrolase may also preferably be obtained from any of the following organisms: *Thermus rehai, Burkholderia* sp-63093, *Gallaecimonas pentaromativorans, Nonomuraea coxensis, Glycomyces rutgersensis, Paraburkholderia phenazinium, Streptomyces griseofuscus, Lysinibacillus xylanilyticus, Tumebacillus ginsengisoli, Lysinibacillus boronitolerans, Microbulbifer hydrolyticus, Carnobacterium inhibens* subsp. One embodiment of the invention relates to a cleaning composition comprising a DNase, a Glyco_hydro_114 glycosyl hydrolase and a cleaning component, wherein the DNase is obtained from *Bacillus*, preferably *Bacillus cibi, Bacillus horikoshii, Bacillus licheniformis, Bacillus subtilis, Bacillus horneckiae, Bacillus idriensis, Bacillus algicola, Bacillus vietnamensis, Bacillus hwajinpoensis, Bacillus indicus, Bacillus marisflavi* or *Bacillus luciferensis* and wherein the Glyco_hydro_114 glycosyl hydrolase is obtained from *Pseudomonas* such as *Pseudomonas* sp-62208, *Pseudomonas seleniipraecipitans, Pseudomonas migulae, Pseudomonas corrugate, Pseudomonas pelagia, Pseudomonas aeruginosa, Pseudomonas composti*. The Glyco_hydro_114 glycosyl hydrolase is preferably obtained from *Myxococcus* such as *Myxococcus macrosporus, Myxococcus virescens, Myxococcus fulvus Myxococcus stipitatus*. The Glyco_hydro_114 glycosyl hydrolase may also preferably be obtained from any of the following organisms: *Thermus rehai, Burkholderia* sp-63093, *Gallaecimonas pentaromativorans, Nonomuraea coxensis, Glycomyces rutgersensis, Paraburkholderia phenazinium, Streptomyces griseofuscus, Lysinibacillus xylanilyticus, Tumebacillus* ginsengisoli, *Lysinibacillus boronitolerans, Microbulbifer hydrolyticus, Camobacterium inhibens* subsp.

One embodiment of the invention relates to a cleaning composition comprising a DNase, a Glyco_hydro_114 glycosyl hydrolase and a cleaning component, wherein the DNase is obtained from *Bacillus*, preferably *Bacillus cibi, Bacillus horikoshii, Bacillus licheniformis, Bacillus subtilis, Bacillus horneckiae, Bacillus idriensis, Bacillus algicola, Bacillus vietnamensis, Bacillus hwajinpoensis, Bacillus indicus, Bacillus marisflavi* or *Bacillus luciferensis* and wherein the Glyco_hydro_114 glycosyl hydrolase is selected from the group consisting of;

a) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 84, b) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 85, c) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 86, d) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 87, e) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 88, f) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 89, g) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 90, h) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 91, i) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 92, j) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 93, k) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 94, l) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 95, m) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, n) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 97, o) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 98, p) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 99, q) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 100, r) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 101, s) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 102, t) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 103, u) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 104,
v) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 105,
w) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 106,
x) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 107,
y) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 108,
z) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, aa) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, bb) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 111,
cc) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 112,
dd) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 113,
ee) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and
ff) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 115.

The DNases preferable belong to the NUC1 group of DNases and comprise one or more of the motifs [T/D/S][G/N]PQL (SEQ ID NO 69), [F/L/Y/I]A[N/R]D[L/I/P/V] (SEQ ID NO: 70), or C[D/N]T[A/R] (SEQ ID NO: 71). The DNases even more preferably comprises a NUC1_A domain [D/Q][I/V]DH (SEQ ID NO 72). In addition, the DNases may preferably comprise any of the domain motifs [T/D/S][G/N]PQL, [F/L/Y/I]A[N/R]D[L/I/P/V] or C[D/N]T[A/R]. The DNases to be added to a composition of the invention preferably belong to the group of DNases comprised in the GYS-clade, which are group of DNases on the same branch of a phylogenetic tree having both structural and functional similarities. These NUC1 and/or NUC1_A DNases comprise the conservative motifs [D/M/L][S/T]GYSR[D/N] (SEQ ID NO: 73) or ASXNRSKG (SEQ ID NO: 74) and share similar structural and functional properties. The DNases of the GYS-clade are preferably obtained from *Bacillus* genus. One embodiment of the invention relates to a cleaning composition comprising a DNase, a Glyco_hydro_114 glycosyl hydrolase and a cleaning component, wherein the DNase comprises one or both of the motif(s) [D/M/L][S/T]GYSR[D/N] (SEQ ID NO: 73) or ASXNRSKG (SEQ ID NO: 74). One embodiment of the invention relates to a cleaning composition comprising a DNase, a Glyco_hydro_114 glycosyl hydrolase and a cleaning component, wherein the DNase preferably comprises one or both of the motif(s) [D/M/L][S/T]GYSR[D/N] (SEQ ID NO: 73) or ASXNRSKG (SEQ ID NO: 74), and wherein the a Glyco_hydro_114 glycosyl hydrolase is selected from the group consisting of;
a) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 84,
b) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 85,
c) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 86,
d) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 87,
e) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 88,
f) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 89,
g) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 90,
h) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 91,
i) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 92,
j) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 93,
k) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 94,
l) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 95,
m) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 96,
n) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 97,
o) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 98,
p) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 99,
q) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 100,
r) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 101,
s) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 102,
t) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 103,
u) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 104,
v) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 105,
w) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 106,
x) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 107,
y) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 108,
z) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 109,
aa) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 110,
bb) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 111,
cc) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 112,
dd) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 113,
ee) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and
ff) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 115.

The glycosyl hydrolases preferably comprise one or more or both the motif(s) GX[FY][LYF]D (SEQ ID NO 82) or AYX[SET]XX[EAS] (SEQ ID NO: 83).

One embodiment of the invention relates to a cleaning composition comprising a DNase, a Glyco_hydro_114 glycosyl hydrolase and a cleaning component, wherein the a Glyco_hydro_114 glycosyl hydrolase optionally comprise one or both the motif(s) GX[FY][LYF]D (SEQ ID NO 82) or AYX[SET]XX[EAS] (SEQ ID NO: 83) and wherein the DNase optionally comprise one or both of the motifs [D/M/L][S/T]GYSR[D/N] (SEQ ID NO: 73), ASXNRSKG (SEQ ID NO: 74) and wherein the DNase is selected from the group consisting of polypeptides comprising or consisting of the polypeptides:
a) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 1, b) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 2,
c) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 3,
d) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 4,
e) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 5,
f) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 6,
g) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 7,
h) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 8,
i) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 9,
j) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 10,
k) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 11,
l) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 12,
m) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 13,
n) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 14,
o) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 15,
p) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 16,
q) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 17,
r) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 18,
s) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 19,
t) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 20,
u) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 21,
v) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 22,
w) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 23,
x) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 24, and
y) a polypeptide having at least 60%, at least 65%, at least 70%, at least 75% at least 80%, at least 85%, at least 90%, at least 95%, at least 98%, at least 99% or 100% sequence identity to the polypeptide shown in SEQ ID NO: 25.

The DNase is preferably a *bacillus* DNase, such as a *Bacillus cibi, Bacillus subtilis* or *Bacillus licheniformis*.

One embodiment of the invention relates to a cleaning composition comprising a DNase, a glycosyl hydrolase, preferably a Glyco_hydro_114 glycosyl hydrolase, and a cleaning component, wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 13.

One embodiment of the invention relates to a cleaning composition comprising a DNase, a glycosyl hydrolase, preferably a Glyco_hydro_114 glycosyl hydrolase, and a cleaning component, wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO: 65.

One embodiment of the invention relates to a cleaning composition comprising a DNase, a glycosyl hydrolase, preferably a Glyco_hydro_114 glycosyl hydrolase, and a cleaning component, wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO: 66.

The DNase may also be fungal, one embodiment of the invention relates to a cleaning composition comprising a DNase, a glycosyl hydrolase, preferably a Glyco_hydro_114 glycosyl hydrolase, and a cleaning component, wherein the DNase is fungal, preferably obtained from *Aspergillus* and even more preferably from *Aspergillus oryzae* and wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO: 67.

One embodiment relates to a cleaning composition comprising a DNase, a glycosyl hydrolase, preferably a Glyco_hydro_114 glycosyl hydrolase, and a cleaning component, wherein the DNase is fungal, preferably obtained from *Trichoderma* and even more preferably from *Trichoderma harzianum* and wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO: 68.

One embodiment of the invention relates to a cleaning composition comprising a DNase, a glycosyl hydrolase, preferably a Glyco_hydro_114 glycosyl hydrolase, and a cleaning component, wherein the glycosyl hydrolase is selected from the group consisting of: *Pseudomonas* protegenes Pf-5 (GenBank: AAY92244), *Pseudomonas aeruginosa* (GenBank:AAG06452) and *Geobacter metallireducens* (GenBank: ABB32191).

One embodiment of the invention relates to a cleaning composition comprising a *Bacillus* DNase, a glycosyl hydrolase, preferably a Glyco_hydro_114 glycosyl hydrolase, and a cleaning component, wherein the glycosyl hydrolase is selected from the group consisting of: *Pseudomonas* protegenes Pf-5 (GenBank: AAY92244), *Pseudomonas aeruginosa* (GenBank:AAG06452) and *Geobacter metallireducens* (GenBank: ABB32191).

One embodiment of the invention relates to a cleaning composition comprising a DNase, a glycosyl hydrolase, preferably a Glyco_hydro_114 glycosyl hydrolase, and a cleaning component, wherein the glycosyl hydrolase is selected from the group consisting of: *Pseudomonas* protegenes Pf-5 (GenBank: AAY92244), *Pseudomonas aeruginosa* (GenBank:AAG06452) and *Geobacter metallireducens* (GenBank: ABB32191) and wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 13.

One embodiment of the invention relates to a cleaning composition comprising a DNase, a glycosyl hydrolase, preferably a Glyco_hydro_114 glycosyl hydrolase, and a cleaning component, wherein the glycosyl hydrolase is selected from the group consisting of: *Pseudomonas* protegenes Pf-5 (GenBank: AAY92244), *Pseudomonas aeruginosa* (GenBank:AAG06452) and *Geobacter metallireducens* (GenBank: ABB32191) and wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO: 65.

One embodiment of the invention relates to a cleaning composition comprising a DNase, a glycosyl hydrolase, preferably a Glyco_hydro_114 glycosyl hydrolase, and a cleaning component, wherein the glycosyl hydrolase is selected from the group consisting of: *Pseudomonas* protegenes Pf-5 (GenBank: AAY92244), *Pseudomonas aeruginosa* (GenBank:AAG06452) and *Geobacter metallireducens* (GenBank: ABB32191) and wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO: 66.

The DNase may also be fungal, one embodiment of the invention relates to a cleaning composition comprising a DNase, a glycosyl hydrolase, preferably a Glyco_hydro_114 glycosyl hydrolase, and a cleaning component, wherein the glycosyl hydrolase is selected from the group consisting of: *Pseudomonas* protegenes Pf-5 (GenBank: AAY92244), *Pseudomonas aeruginosa* (GenBank:AAG06452) and *Geobacter metallireducens* (GenBank: ABB32191), wherein the DNase is fungal, preferably obtained from *Aspergillus* and even more preferably from *Aspergillus oryzae* and wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO: 67.

One embodiment relates to a cleaning composition comprising a DNase, a glycosyl hydrolase, preferably a Glyco_hydro_114 glycosyl hydrolase, and a cleaning component, wherein the glycosyl hydrolase is selected from the group consisting of: *Pseudomonas* protegenes Pf-5 (GenBank: AAY92244), *Pseudomonas aeruginosa* (GenBank: AAG06452) and *Geobacter metallireducens* (GenBank: ABB32191), wherein the DNase is fungal, preferably obtained from *Trichoderma* and even more preferably from *Trichoderma harzianum* and wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO: 68

One embodiment of the invention relates to a cleaning composition comprising a DNase, a glycosyl hydrolase, preferably a Glyco_hydro_114 glycosyl hydrolase, and a cleaning component, wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 13 and wherein the glycosyl hydrolase is selected from the group of glycosyl hydrolases comprising an amino acid sequence with;
    i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84,
    ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85,
    iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86, iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87, v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.

xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115.

One embodiment of the invention relates to a cleaning composition comprising a DNase, a glycosyl hydrolase, preferably a Glyco_hydro_114 glycosyl hydrolase, and a cleaning component, wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 65 and wherein the glycosyl hydrolase is selected from the group of glycosyl hydrolases comprising an amino acid sequence with;

i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84, ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85, iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86, iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87, v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.

xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115.

One embodiment of the invention relates to a cleaning composition comprising a DNase, a glycosyl hydrolase, preferably a Glyco_hydro_114 glycosyl hydrolase and a cleaning component, wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 66 and wherein the glycosyl hydrolase is selected from the group of glycosyl hydrolases comprising an amino acid sequence with;

i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84,
ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85,
iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86,
iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87,
v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88,
vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89,
vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90,
viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91,
ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92,
x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93,
xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94,
xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95,
xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96,
xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97,
xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98,
xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99,
xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100,
xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101,
xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102,
xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103,
xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104,
xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.
xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106,
xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107,
xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108,
xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109,
xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110,
xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111,
xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112,
xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113,
xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and
xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115.

One embodiment of the invention relates to a cleaning composition comprising a DNase, a glycosyl hydrolase, preferably a Glyco_hydro_114 and a cleaning component, wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 67 and wherein the glycosyl hydrolase is selected from the group of glycosyl hydrolases comprising an amino acid sequence with;

i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84, ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85, iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86, iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87, v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.

xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115.

One embodiment of the invention relates to a cleaning composition comprising a DNase, a glycosyl hydrolase, preferably a Glyco_hydro_114, and a cleaning component, wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 68 and wherein the glycosyl hydrolase is selected from the group of glycosyl hydrolases comprising an amino acid sequence with;

i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84,
ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85,
iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86,
iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87,
v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88,
vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89,
vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90,
viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91,
ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92,
x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93,
xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94,
xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95,
xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96,
xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97,
xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98,
xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99,
xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100,
xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101,
xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102,
xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103,
xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104,
xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.
xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106,
xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107,
xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108,
xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109,
xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110,
xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111,
xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112,
xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115.

One embodiment of the invention relates to a composition e.g. A composition comprising a) at least 0.001 ppm of at least one DNase, wherein the DNase is selected from the group consisting of:
  i) a DNase comprising one or more of the motifs [T/D/S][G/N]PQL (SEQ ID NO 69), [F/L/Y/I]A[N/R]D[L/I/P/V] (SEQ ID NO: 70), or C[D/N]T[A/R] (SEQ ID NO: 71);
  ii) a DNase comprising the motif [D/Q][IN]DH (SEQ ID NO 72);
  iii) a DNase comprising one or both of the motifs [D/M/L][S/T]GYSR[D/N] (SEQ ID NO: 73) or ASXNRSKG (SEQ ID NO: 74);
  iv) a DNase comprising one or both of the motifs [V/I]PL[S/A]NAWK (SEQ ID NO: 75) or NPQL (SEQ ID NO: 76);
  v) a DNase comprising one or both of the motifs P[Q/E]L[W/Y] (SEQ ID NO: 77) or [K/H/E]NAW (SEQ ID NO:78);
  vi) a DNase selected from: a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 1, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 2, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 3, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 4, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 5, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 6, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 7, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 8, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 9, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 10, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 11, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 12, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 13, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 14, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 15, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 16, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 17, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 18, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 19, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 20, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 21, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 22, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 23, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 24, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 25, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 26, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 27, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 28, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 29, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 30, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 31, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 32, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 33, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 34, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 35, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 36, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 37, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 38, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 39, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 40, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 41, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 42, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 43, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 44, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 45, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 46, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 47, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 48, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 49, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 50, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 51, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 52, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 53, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 54, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 55, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 56, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 57, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 58, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 59, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 60, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 61, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 62, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 63, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 64, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 65, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 66, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 67, and a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 68, and b) at least 0.001 ppm of one or more glycosyl hydrolase, wherein the glycosyl hydrolase is selected from the group consisting of;
  i) a glycosyl hydrolase comprising one or both the motifs motif(s) GX[FY][LYF]D (SEQ ID NO 82) or AYX[SET]XX[EAS] (SEQ ID NO: 83);
  ii) a glycosyl hydrolase selected from a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 85, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 86, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 87, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 99 a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 103 a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 105, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 114 and a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 115;

iii) a glycosyl hydrolase selected from the group of glycosyl hydrolases consisting of *Pseudomonas protegenes* Pf-5 with GenBank no. AAY92244, *Pseudomonas aeruginosa* with GenBank No. AAG06452 and *Geobacter metallireducens* with GenBank No. ABB32191; and iv) A glycosyl hydrolase of the Glyco_hydro_114 pFam domain (PF03537) family; and c) At least one cleaning component, preferably selected from surfactants, builders, bleach components, polymers and dispersing agents.

Optionally the cleaning composition comprises at least 0.001 ppm of one or more protease, selected from the group consisting of, i) a protease variant of a protease parent, wherein the protease variant comprises one or more alteration(s) compared to a protease shown in SEQ ID NO 79 or SEQ ID NO 80 in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269, wherein the positions correspond to the positions of the protease shown in SEQ ID NO 79 and wherein the protease variant has at least 60%, at least 65%, at least 70%, at least 75% at least 80%, at least 85%, at least 90%, at least 95%, at least 98% but less than 100% sequence identity to SEQ ID NO 79 or SEQ ID NO 80;

ii) a protease variant of a protease parent, wherein the protease variant comprises one or more mutation selected from the group consisting of: S3T, V4I, S9R, S9E, A15T, S24G, S24R, K27R, N42R, S55P, G59E, G59D, N60D, N60E, V66A, N74D, S85R, A96S, S97G, S97D, S97A, S97SD, S99E, S99D, S99G, S99M, S99N, S99R, S99H, S101A, V102I, V102Y, V102N, S104A, G116V, G116R, H118D, H118N, A120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A and R269H, wherein the positions correspond to the positions of the protease shown in SEQ ID NO 79, wherein the protease variant has at least 60%, at least 65%, at least 70%, at least 75% at least 80%, at least 85%, at least 90%, at least 95%, at least 98% but less than 100% sequence identity to SEQ ID NO 79 or SEQ ID NO 80;

iii) a protease comprising a substitution at one or more positions corresponding to positions 171, 173, 175, 179, or 180 of SEQ ID NO: 81, compared to the protease shown in SEQ ID NO 81, wherein the protease variant has a sequence identity of at least 60%, at least 65%, at least 70%, at least 75% at least 80%, at least 85%, at least 90%, at least 95%, at least 98% but less than 100% sequence identity to the amino acid sequence 1 to 311 of SEQ ID NO 81, iv) a protease comprising the amino acid sequence shown in SEQ ID NO 79, 80, 81, 82 or a protease having at least 60%, at least 65%, at least 70%, at least 75% at least 80%, at least 85%, at least 90%, at least 95%, at least 98% but less than 100% sequence identity to; the polypeptide comprising amino acids 1-269 of SEQ ID NO 79, the polypeptide comprising amino acids 1-311 of SEQ ID NO 81 or the polypeptide comprising amino acids 1-275 of SEQ ID NO 80;

v) One or more of the following protease variants selected from the group:
SEQ ID NO 79+T22R+S99G+S101A+V102I+A226V+Q239R,
SEQ ID NO 80+S24G+S53G+S78N+S101N+G128A+Y217Q,
SEQ ID NO 80+S24G+S53G+S78N+S101N+G128S+Y217Q,
SEQ ID NO 79+S9E+N42R+N74D+V199I+Q200L+Y203W+S253D+N255W+L256E,
SEQ ID NO 79+S9E+N42R+N74D+H118V+Q176E+A188P+V199I+Q200L Y203W+S250D+S253D+N255W+L256E
SEQ ID NO 79+S9E+N42R+N74D+Q176E+A188P+V199I+Q200L+Y203W S250D+S253D+N255W+L256E
SEQ ID NO 79+S3V+N74D+H118V+Q176E+N179E+S182E+V199I+Q200L Y203W+S210V+S250D+S253D+N255W+L256E
SEQ ID NO 79+T22A+N60D+S99G+S101A+V102I+N114L+G157D+S182 D+T207A+A226V+Q239R+N242D+E265F,
SEQ ID NO 79+S9E+N42R+N74D+H118V+Q176E+A188P+V199I+Q200L+Y203W+S250D+S253D+N255W+L256E,
SEQ ID NO 79+S9E+N42R+N74D+Q176E+A188P+V199I+Q200L+Y203W+S250D+S253D+N255W+L256E,
SEQ ID NO 79+S9E+N42R+N74D+H118V+Q176E+A188P+V199I+Q200L+Y203W+S250D+N255W+L256E+*269aH+*269bH,
SEQ ID NO 79+S3V+N74D+H118V+Q176E+N179E+S182E+V199I+Q200L+Y203W+S210V+S250D+N255W+L256E,
SEQ ID NO 79+S9E+N74D+G113W+G157P+Q176E+V199I+Q200L+Y203W+S250D+T254E+N255W+L256E,
SEQ ID NO 79+S3V+S9R+N74D+H118V+Q176E+N179E+S182E+V199I+Q200L+Y203W+S212V+S250D+N255W+L256E,
SEQ ID NO 79+S99E, and
SEQ ID NO 80+L217D.

The term "corresponding to" reflects the numbering system used and that various starting proteases (parent proteases) may have different length. Thus, a given starting protease is aligned with e.g. SEQ ID NO 79 and the position corresponding to e.g. pos 3 is determined. SEQ ID NO XX+mutation(s) is to be understood as variants of a protease parent comprising specified mutations compared to the specific parent sequence e.g. SEQ ID NO 80+L217D is a variant of a protease shown in SEQ ID NO 80, which compared to SEQ ID NO 80 comprise the mutation L217D (substitution of Leucine in position 217 of SEQ ID NO 80 with Aspartic acid). The protease suitable for combining with the DNase in a composition of the invention are preferably any of the above, such proteases are very useful in detergents and are suitable for combining with DNases.

The glycosyl hydrolase and DNase may be included in the cleaning composition of the present invention at a level of from 0.01 to 1000 ppm, from 1 ppm to 1000 ppm, from 10 ppm to 1000 ppm, from 50 ppm to 1000 ppm, from 100 ppm to 1000 ppm, from 150 ppm to 1000 ppm, from 200 ppm to 1000 ppm, from 250 ppm to 1000 ppm, from 250 ppm to 750 ppm, from 250 ppm to 500 ppm. The DNases above may be combined with the glycosyl hydrolase to form a blend to be added to the wash liquor solution according to the invention. The concentration of the DNase in the wash liquor solution is typically in the range of wash liquor from 0.00001 ppm to 10 ppm, from 0.00002 ppm to 10 ppm, from 0.0001 ppm to 10 ppm, from 0.0002 ppm to 10 ppm, from 0.001 ppm to 10 ppm, from 0.002 ppm to 10 ppm, from 0.01 ppm to 10 ppm, from 0.02 ppm to 10 ppm, 0.1 ppm to 10 ppm, from 0.2 ppm to 10 ppm, from 0.5 ppm to 5 ppm. The concentration of the Glyco_hydro_114 glycosyl hydrolase in the wash liquor solution is typically in the range of wash liquor from 0.00001 ppm to 10 ppm, from 0.00002 ppm to 10 ppm, from 0.0001 ppm to 10 ppm, from 0.0002 ppm to 10 ppm, from 0.001 ppm to 10 ppm, from 0.002 ppm to 10 ppm, from 0.01 ppm to 10 ppm, from 0.02 ppm to 10 ppm, 0.1 ppm to 10 ppm, from 0.2 ppm to 10 ppm, from 0.5 ppm to 5 ppm. The DNases may be combined with any of the glycosyl hydrolases mentioned above to form a blend to be added to a composition according to the invention.

One embodiment relates to a cleaning composition comprising a DNase, a Glyco_hydro_114 glycosyl hydrolase and at least one cleaning component, wherein the amount of DNase in the composition is from 0.01 to 1000 ppm and the amount of Glyco_hydro_114 glycosyl hydrolase is from 0.01 to 1000 ppm.

A method of formulating a cleaning composition comprising a DNase, a Glyco_hydro_114 glycosyl hydrolase and at least one cleaning component, comprising adding a DNase, a Glyco_hydro_114 glycosyl hydrolase and at least one cleaning component.

The choice of cleaning components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

A composition comprising
a) at least 0.001 ppm of at least one DNase, wherein the DNase is selected from the group consisting of:
 i) a DNase comprising one or more of the motifs [T/D/S][G/N]PQL (SEQ ID NO 69), [F/L/Y/I]A[N/R]D[L/I/P/V] (SEQ ID NO: 70), or C[D/N]T[A/R] (SEQ ID NO: 71);
 ii) a DNase comprising the motif [D/Q][IN]DH (SEQ ID NO 72);
 iii) a DNase comprising one or both of the motifs [D/M/L][S/T]GYSR[D/N] (SEQ ID NO: 73) or ASXNRSKG (SEQ ID NO: 74);
 iv) a DNase comprising one or both of the motifs [V/I]PL[S/A]NAWK (SEQ ID NO: 75) or NPQL (SEQ ID NO: 76);

v) a DNase comprising one or both of the motifs P[Q/E]L[W/Y] (SEQ ID NO: 77) or [K/H/E]NAW (SEQ ID NO:78);
vi) a DNase selected from the group consisting of: a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 1, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 2, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 3, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 4, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 5, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 6, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 7, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 8, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 9, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 10, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 11, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 12, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 13, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 14, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 15, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 16, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 17, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 18, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 19, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 20, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 21, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 22, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 23, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 24, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 25, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 26, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 27, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 28, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 29, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 30, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 31, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 32, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 33, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 34, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 35, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 36, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 37, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 38, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 39, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 40, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 41, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 42, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 43, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 44, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 45, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 46, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 47, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 48, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 49, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 50, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 51, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 52, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 53, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 54, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 55, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 56, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 57, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 58, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 59, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 60, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 61, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 62, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 63, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 64, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 65, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 66, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 67, and a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 68, and b) at least 0.001 ppm of one or more glycosyl hydrolase, wherein the glycosyl hydrolase is selected from the group consisting of;
 i) a glycosyl hydrolase comprising one or both the motifs motif(s) GX[FY][LYF]D (SEQ ID NO 82) or AYX[SET]XX[EAS] (SEQ ID NO: 83);
 ii) a glycosyl hydrolase selected from a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 84, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 85, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 86, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 87, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 105, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 114 and a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 115;
iii) a glycosyl hydrolase selected from the group of glycosyl hydrolases consisting of *Pseudomonas* protegenes Pf-5 with GenBank no. AAY92244, *Pseudomonas aeruginosa* with GenBank No. AAG06452 and *Geobacter metallireducens* with GenBank No. ABB32191; and
iv) A glycosyl hydrolase of the Glyco_hydro_114 pFam domain (PF03537) family; and c) At least one cleaning component, preferably selected from surfactants, builders, bleach components, polymers and dispersing agents.

Optionally the cleaning composition comprises at least 0.001 ppm of one or more protease, selected from,
i) a protease variant of a protease parent, wherein the protease variant comprises one or more alteration(s) compared to a protease shown in SEQ ID NO 79 or SEQ ID NO 80 in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269, wherein the positions correspond to the positions of the protease shown in SEQ ID NO 79 and wherein the protease variant has at least 80% sequence identity to SEQ ID NO 79, SEQ ID NO 80 or SEQ ID NO 81;
ii) a protease variant of a protease parent, wherein the protease variant comprises one or more mutation selected from the group consisting of S3T, V4I, S9R, S9E, A15T, S24G, S24R, K27R, N42R, S55P, G59E, G59D, N60D, N60E, V66A, N74D, N85S, N85R, G96S, G96A, S97G, S97D, S97A, S97SD, S99E, S99D, S99G, S99M, S99N, S99R, S99H, S101A, V102I, V102Y, V102N, S104A, G116V, G116R, H118D, H118N, N120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A and R269H, wherein the positions correspond to the positions of the protease shown in SEQ ID NO 79, wherein the protease variant has at least 80% sequence identity to SEQ ID NO 79, SEQ ID NO 80 or SEQ ID NO 81;
iii) a protease comprising a substitution at one or more positions corresponding to positions 171, 173, 175, 179, or 180 of SEQ ID NO: 81, compared to the protease shown in SEQ ID NO 81, wherein the protease variant has a sequence identity of at least 75% but less than 100% to amino acid 1 to 311 of SEQ ID NO 81, a protease comprising the amino acid sequence shown in SEQ ID NO 79, 80 or 81 or a protease having at least 80% sequence identity to; the polypeptide comprising amino acids 1-269 of SEQ ID NO 79, the polypeptide comprising amino acids 1-311 of SEQ ID NO 81 or the polypeptide comprising amino acids 1-275 of SEQ ID NO 80.

The DNases may be combined with any of the Glyco_hydro_114 glycosyl hydrolase of the invention to form a blend to be added to a composition according to the invention.

One embodiment relates to a cleaning composition comprising a DNase, a Glyco_hydro_114 glycosyl hydrolase and at least one cleaning component, wherein the amount of DNase in the composition is from 0.01 to 1000 ppm and the amount of Glyco_hydro_114 glycosyl hydrolase is from 0.01 to 1000 ppm.

In addition to the Glyco_hydro_114 glycosyl hydrolase and DNase the cleaning composition further comprises one or more cleaning component. One embodiment relates to a cleaning composition comprising a DNase, a Glyco_hydro_114 glycosyl hydrolase and at least one cleaning component, wherein the cleaning component is selected from surfactants, preferably anionic and/or nonionic, builders and bleach components.

The choice of cleaning components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0.01% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0.01% to about 10% by weight of a zwitterionic surfactant. Non-limiting examples of zwitterionic surfactants include betaines such as alkyldimethylbetaines, sulfobetaines, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2- sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Bleaching Systems

The detergent may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O]manganese(II). The bleach catalysts may also be other metal compounds; such as iron or cobalt complexes.

In some embodiments, where a source of a peracid is included, an organic bleach catalyst or bleach booster may be used having one of the following formulae:

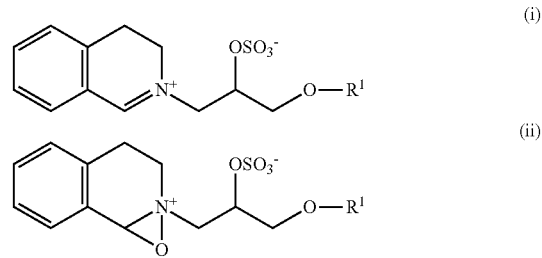

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Metal Care Agents

Metal care agents may prevent or reduce the tarnishing, corrosion or oxidation of metals, including aluminium, stainless steel and non-ferrous metals, such as silver and copper. Suitable examples include one or more of the following:

(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain Ci-C20-alkyl groups (e.g., C1-C20-alkyl groups) and hydroxyl, thio, phenyl or halogen such as fluorine, chlorine, bromine and iodine.

(b) metal salts and complexes chosen from the group consisting of zinc, manganese, titanium, zirconium, hafnium, vanadium, cobalt, gallium and cerium salts and/or complexes, the metals being in one of the oxidation states II, III, IV, V or VI. In one aspect, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate; (c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859. Preferably the composition of the invention comprises from 0.1 to 5% by weight of the composition of a metal care agent, preferably the metal care agent is a zinc salt.

Hydrotropes

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF, which helps to prevent redeposition of soil in the wash liquor.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Enzymes

The composition of the invention is preferably a cleaning composition as well as the detergent composition and the composition may comprise one or more additional enzymes such as one or more lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Proteases

The term "protease" is defined herein as an enzyme that hydrolyzes peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in *Eur. J. Biochem.* 1223: 1-5 (1994); *Eur. J. Biochem.* 232: 1-6 (1995); *Eur. J. Biochem.* 237: 1-5 (1996); Eur. J. *Biochem.* 250: 1-6 (1997); and *Eur. J. Biochem.* 264: 610-650 (1999); respectively. The most widely used proteases in the detergent industry such as laundry and dish wash are the serine proteases. Serine proteases is a subgroup of proteases characterized by having a serine in the active site, which forms a covalent adduct with the substrate. Serine proteases are characterized by having two active site amino acid residues apart from the serine, namely a histidine residue and an aspartic acid residue. Subtilase refer to a sub-group of serine protease according to Siezen et al., 1991, *Protein Engng.* 4: 719-737 and Siezen et al., 1997, *Protein Science* 6: 501-523. The subtilases may be divided into 6 sub-divisions, i.e., the Subtilisin family, the Thermitase family, the Proteinase K family, the Lantibiotic peptidase family, the Kexin family and the Pyrolysin family. The term "protease activity" means a proteolytic activity (EC 3.4). Proteases usably in cleaning compositions of the present invention are mainly endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1.

Suitable proteases for the compositions of the invention include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloproteases, such as those from M5, M7 or M8 families.

Examples of subtilases are those derived from *Bacillus* such as *Bacillus lentus, Bacillus alkalophilus, Bacillus subtilis, Bacillus amyloliquefaciens, Bacillus pumilus* and *Bacillus gibsonii* described in; U.S. Pat. No. 7,262,042 and WO09/021867, and subtilisin lentus, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellumonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially protease variants comprising a substitution in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269, wherein the positions correspond to the positions of the *Bacillus lentus* protease shown in SEQ ID NO 79. More preferred the protease variants may comprise one or more of the mutations selected from the group consisting of: S3T, V4I, S9R, S9E, A15T, S24G, S24R, K27R, N42R, S55P, G59E, G59D, N60D, N60E, V66A, N74D, S85R, A96S, S97G, S97D, S97A, S97SD, S99E, S99D, S99G, S99M, S99N, S99R, S99H, S101A, V102I, V102Y, V102N, S104A, G116V, G116R, H118D, H118N, A120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A and R269H. The protease variants are preferably variants of the *Bacillus lentus* protease shown in SEQ ID NO 1 of WO2016/001449 or the *Bacillus amylolichenifaciens* protease (BPN') shown in SEQ ID NO 2 of WO2016/001449. The protease variants preferably have at least 80% sequence identity to SEQ ID NO 1 or SEQ ID NO 2 of WO 2016/001449.

A protease variant comprising a substitution at one or more positions corresponding to positions 171, 173, 175, 179, or 180 of SEQ ID NO: 81, wherein said protease variant has a sequence identity of at least 75% but less than 100% to SEQ ID NO: 81.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme@, Coronase®, Coronase® Ultra, Blaze®, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™ Purafect Prime®, Preferenz P110™, Effectenz P1000™, Purafect®™, Effectenz P1050™ Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Mannanases

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. A commercially available mannanase is Mannaway (Novozymes A/S).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes A/S).

Lipases and Cutinases:

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases:

Suitable amylases include alpha-amylases and/or a glucoamylases and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 of WO 2006/066594 are those having the substitutions:

M197T;

H156Y+A181T+N190F+A209V+Q264S; or

G48A+T491+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one or more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;

N128C+K178L+T182G+F202Y+Y305R+D319T+ G475K;

S125A+N128C+K178L+T182G+Y305R+G475K; or

S125A+N128C+T131I+T165I+K178L+T182G+Y305R+ G475K wherein the variants are C-terminally truncated and optionally further comprises a substitution at position 243 and/or a deletion at position 180 and/or position 181.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K

E187P+I203Y+R458N+T459S+D460T+G476K wherein the variants optionally further comprise a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21D+D97N+V128I wherein the variants optionally further comprise a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz S110 (from Genencor International Inc./DuPont).

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A suitable peroxidase includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. Preferably, the haloperoxidase is a vanadium haloperoxidase, i.e., a vanadate-containing haloperoxidase. Haloperoxidases have been isolated from many different fungi, in particular from the fungus group dematiaceous hyphomycetes, such as Caldariomyces, e.g., *C. fumago, Alternaria, Curvularia*, e.g., *C. verruculosa* and *C. inaequalis, Drechslera, Ulocladium* and *Botrytis*.

Haloperoxidases have also been isolated from bacteria such as *Pseudomonas*, e.g., *P. pyrrocinia* and *Streptomyces*, e.g., *S. aureofaciens*.

A suitable oxidase includes in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885). Suitable examples from bacteria include a laccase derivable from a strain of *Bacillus*. A laccase derived from *Coprinopsis* or *Myceliophthora* is preferred; in particular, a laccase derived from *Coprinopsis cinerea*, as disclosed in WO 97/08325; or from *Myceliophthora thermophila*, as disclosed in WO 95/33836.

Dispersants

The cleaning compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The cleaning compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2,2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers

The cleaning compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, CI-C6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose derivatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The cleaning compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The cleaning compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The cleaning composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Granular Detergent Formulations

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The DNase may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multienzyme co-granulate for the detergent industry is disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component. The multi-enzyme co-granule may comprise an enzyme of the invention and one or more enzymes selected from the group consisting of proteases, lipases, cellulases, xyloglucanases, perhydrolases, peroxidases, lipoxygenases, laccases, hemicellulases, proteases, cellulases, cellobiose dehydrogenases, xylanases, phospholipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof.

WO 2013/188331 also relates to a method of treating and/or cleaning a surface, preferably a fabric surface comprising the steps of (i) contacting said surface with the detergent composition as claimed and described herein in aqueous wash liquor, (ii) rinsing and/or drying the surface.

An embodiment of the invention relates to an enzyme granule/particle comprising the DNase and Glyco_hydro_114 glycosyl hydrolase. The granule is composed of a core, and optionally one or more coatings (outer layers) surrounding the core. Typically, the granule/particle size, measured as equivalent spherical diameter (volume based average particle size), of the granule is 20-2000 μm, particularly 50-1500 μm, 100-1500 μm or 250-1200 μm. The core may include additional materials such as fillers, fibre materials (cellulose or synthetic fibres), stabilizing agents, solubilising agents, suspension agents, viscosity regulating agents, light spheres, plasticizers, salts, lubricants and fragrances. The core may include binders, such as synthetic polymer, wax, fat, or carbohydrate. The core may comprise a salt of a multivalent cation, a reducing agent, an antioxidant, a peroxide decomposing catalyst and/or an acidic buffer component, typically as a homogenous blend. The core may consist of an inert particle with the enzyme absorbed into it, or applied onto the surface, e.g., by fluid bed coating. The core may have a diameter of 20-2000 μm, particularly 50-1500 μm, 100-1500 μm or 250-1200 μm. The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606. The coating may be applied in an amount of at least 0.1% by weight of the core, e.g., at least 0.5%, 1% or 5%. The amount may be at most 100%, 70%, 50%, 40% or 30%. The coating is preferably at least 0.1 µm thick, particularly at least 0.5 µm, at least 1 µm or at least 5 µm. In a one embodiment, the thickness of the coating is below 100 µm. In another embodiment, the thickness of the coating is below 60 µm. In an even more particular embodiment the total thickness of the coating is below 40 µm. The coating should encapsulate the core unit by forming a substantially continuous layer. A substantially continuous layer is to be understood as a coating having few or no holes, so that the core unit it is encapsulating/enclosing has few or none uncoated areas. The layer or coating should be homogeneous in thickness. The coating can further contain other materials as known in the art, e.g., fillers, antisticking agents, pigments, dyes, plasticizers and/or binders, such as titanium dioxide, kaolin, calcium carbonate or talc. A salt coating may comprise at least 60% by weight w/w of a salt, e.g., at least 65%, at least 70%, at least 75%, at least 80%, at least 85%, at least 90%, at least 95% or at least 99% by weight w/w. The salt may be added from a salt solution where the salt is completely dissolved or from a salt suspension wherein the fine particles is less than 50 µm, such as less than 10 µm or less than 5 µm. The salt coating may comprise a single salt or a mixture of two or more salts. The salt may be water soluble, and may have a solubility at least 0.1 grams in 100 g of water at 20° C., preferably at least 0.5 g per 100 g water, e.g., at least 1 g per 100 g water, e.g., at least 5 g per 100 g water. The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used. The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710. Specific examples of suitable salts are NaCl ($CH_{20°\ C.}$=76%), $Na_2CO_3$ ($CH_{20°\ C.}$=92%), $NaNO_3$ ($CH_{20°\ C.}$=73%), $Na_2HPO_4$ ($CH_{20°\ C.}$=95%), $Na_3PO_4$ ($CH_{25°\ C.}$=92%), $NH_4Cl$ ($CH_{20°\ C.}$=79.5%), $(NH_4)_2HPO_4$ ($CH_{20°\ C.}$=93.0%), $NH_4H_2PO_4$ ($CH_{20°\ C.}$=93.1%), $(NH_4)_2SO_4$ ($CH_{20°\ C.}$=81.1%), KCl ($CH_{20°\ C.}$=85%), $K_2HPO_4$ ($CH_{20°\ C.}$=92%), $KH_2PO_4$ ($CH_{20°\ C.}$=96.5%), $KNO_3$ ($CH_{20°\ C.}$=93.5%), $Na_2SO_4$ ($CH_{20°\ C.}$=93%), $K_2SO_4$ ($CH_{20°\ C.}$=98%), $KHSO_4$ ($CH_{20°\ C.}$=86%), $MgSO_4$ ($CH_{20°\ C.}$=90%), $ZnSO_4$ ($CH_{20°\ C.}$=90%) and sodium citrate ($CH_{25°\ C.}$=86%). Other examples include $NaH_2PO_4$, $(NH_4)H_2PO_4$, $CuSO_4$, $Mg(NO_3)_2$ and magnesium acetate. The salt may be in anhydrous form, or it may be a hydrated salt, i.e. a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4.7H_2O$), zinc sulfate heptahydrate ($ZnSO_4.7H_2O$), sodium phosphate dibasic heptahydrate ($Na_2HPO_4.7H_2O$), magnesium nitrate hexahydrate ($Mg(NO_3)_2(6H_2O)$), sodium citrate dihydrate and magnesium acetate tetrahydrate. Preferably the salt is applied as a solution of the salt, e.g., using a fluid bed. One embodiment of the present invention provides a granule, which comprises:

(a) a core comprising a DNase and a Glyco_hydro_114 glycosyl hydrolase, and
(b) optionally a coating consisting of one or more layer(s) surrounding the core.

One embodiment of the invention relates to a granule, which comprises:

(a) a core comprising a DNase and a glycosyl hydrolase, preferably a Glyco_hydro_114 glycosyl hydrolase wherein the glycosyl hydrolase is selected from a group consisting of glycosyl hydrolases comprising an amino acid sequence with;
  i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84,
  ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85,
  iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86,
  iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87,
  v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88,
  vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89,
  vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90,
  viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91,
  ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.

xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115, and wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 13, and (b) optionally a coating consisting of one or more layer(s) surrounding the core.

One embodiment of the invention relates to a granule, which comprises:

(a) a core comprising a DNase and a glycosyl hydrolase, preferably a Glyco_hydro_114 glycosyl hydrolase wherein the glycosyl hydrolase is selected from the group consisting of glycosyl hydrolases comprising an amino acid sequence with;

i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84, ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85, iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86,
iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87,
v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88,
vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89,
vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90,
viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91,
ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92,
x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93,
xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94,
xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95,
xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96,
xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97,
xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98,
xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99,
xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100,
xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101,
xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102,
xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103,
xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104,
xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.
xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106,
xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107,
xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108,
xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109,
xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110,
xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111,
xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112,
xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113,
xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and
xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115, and wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 65, and (b) optionally a coating consisting of one or more layer(s) surrounding the core.

One embodiment of the invention relates to a granule, which comprises:

(a) a core comprising a DNase and a glycosyl hydrolase, preferably a Glyco_hydro_114 glycosyl hydrolase, wherein the glycosyl hydrolase is selected from the group consisting of glycosyl hydrolases comprising an amino acid sequence with;

i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84, ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85, iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86, iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87, v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.

xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110,
xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111,
xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112,
xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113,
xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114,
xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115,
and wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 66, and
(b) optionally a coating consisting of one or more layer(s) surrounding the core.

One embodiment of the invention relates to a granule, which comprises:
(a) a core comprising a DNase and a glycosyl hydrolase, preferably a Glyco_hydro_114 glycosyl hydrolase, wherein the glycosyl hydrolase is selected from the group consisting of glycosyl hydrolases comprising an amino acid sequence with;
i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84,
ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85,
iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86,
iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87,
v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88,
vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89,
vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90,
viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91,
ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92,
x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93,
xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94,
xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95,
xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96,
xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97,
xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98,
xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99,
xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100,
xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101,
xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102,
xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103,
xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104,
xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.

xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115, and wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 67, and (b) optionally a coating consisting of one or more layer(s) surrounding the core.

One embodiment of the invention relates to a granule, which comprises:

(a) a core comprising a DNase and a glycosyl hydrolase, preferably a Glyco_hydro_114 glycosyl hydrolase, wherein the glycosyl hydrolase is selected from the group of glycosyl hydrolases comprising an amino acid sequence with;

i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84, ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85, iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86, iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87, v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.

xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115, and wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 68, and (b) optionally a coating consisting of one or more layer(s) surrounding the core.

Uses

The present invention is also directed to methods for using the compositions thereof. Laundry/textile/fabric (House hold laundry washing, Industrial laundry washing). Hard surface cleaning (ADW, car wash, Industrial surface)

Use of Cleaning Composition

The detergent composition of the present invention may be formulated, for example, as a hand or machine laundry detergent composition including a laundry additive composition suitable for pretreatment of stained fabrics and a rinse added fabric softener composition, or be formulated as a detergent composition for use in general household hard surface cleaning operations, or be formulated for hand or machine dishwashing operations. In a specific aspect, the present invention provides a detergent additive comprising one or more enzymes as described herein.

The present invention is also directed to methods for using the compositions thereof. Laundry/textile/fabric (House hold laundry washing, Industrial laundry washing). Hard surface cleaning (ADW, car wash, Industrial surface). The compositions of the invention comprise a blend of DNase and Glyco_hydro_114 glycosyl hydrolase and effectively reduce or remove organic components, such as polysaccharide and DNA from surfaces such as textiles and hard surfaces e.g. dishes.

The compositions of the invention comprise a blend of DNase and Glyco_hydro_114 glycosyl hydrolase, and effectively reduce or remove organic components, such as polysaccharides and DNA from surfaces such as textiles and hard surfaces e.g. dishes. One embodiment of the invention relates to the use of a cleaning composition comprising a DNase, a Glyco_hydro_114 glycosyl hydrolase and at least one cleaning component for reduction or removal of components of biofilm, such as DNA and Glyco_hydro_114 glycosyl hydrolase, of an item, wherein the item is a textile or a hard surface.

One embodiment of the invention relates to the use of a cleaning composition comprising a DNase, at least one Glyco_hydro_114 glycosyl hydrolase and a cleaning component for deep cleaning of an item, wherein the item is a textile or a surface.

One embodiment of the invention relates to the use of a composition comprising a DNase and a Glyco_hydro_114 glycosyl hydrolase for reduction or removal of biofilm and/or compounds such as polysaccharide and DNA of an item. One embodiment of the invention relates to the use of a cleaning composition comprising a DNase and a Glyco_ hydro_114 glycosyl hydrolase for reduction or removal of biofilm and/or compounds such as polysaccharide and DNA of an item such as textile. One embodiment of the invention relates to the use of a cleaning composition comprising a DNase and a Glyco_hydro_114 glycosyl hydrolase for deep cleaning when the cleaning composition is applied in e.g. laundry process.

One embodiment of the invention relates to the use of a composition comprising a DNase and Glyco_hydro_114 glycosyl hydrolase for reduction of redeposition or reduction of malodor. One embodiment of the invention relates to the use of a cleaning composition comprising a DNase and Glyco_hydro_114 glycosyl hydrolase for reduction of redeposition or reduction of malodor.

One embodiment of the invention relates to the use of a cleaning composition comprising a DNase and Glyco_hydro_114 glycosyl hydrolase for reduction of redeposition or reduction of malodor when the cleaning composition is applied in e.g. laundry process. One embodiment of the invention relates to the use of a cleaning composition comprising a DNase and Glyco_hydro_114 glycosyl hydrolase for reduction of redeposition or reduction of malodor on an item e.g. textile. In one embodiment, the composition is an anti-redeposition composition.

One embodiment of the invention relates to the use of a cleaning composition comprising a DNase and a glycosyl hydrolase preferably a Glyco_hydro_114 glycosyl hydrolase for deep cleaning of an item or reduction of redeposition or malodor, wherein the glycosyl hydrolase is selected from the group consisting of polypeptides comprising an amino acid sequence having i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84, ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85, iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86, iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87, v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.

xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109,
xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110,
xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111,
xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112,
xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113,
xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and
xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115.

One embodiment of the invention relates to the use of a cleaning composition comprising a DNase and a glycosyl hydrolase, preferably a Glyco_hydro_114 glycosyl hydrolase for deep cleaning of an item or reduction of redeposition or malodor, wherein the glycosyl hydrolase is selected from the group of polypeptides consisting of polypeptides comprising an amino acid sequence having;

i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84,
ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85,
iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86,
iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87,
v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88,
vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89,
vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90,
viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91,
ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92,
x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93,
xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94,
xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95,
xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96,
xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97,
xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98,
xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99,
xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100,
xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101,
xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102,
xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103,
xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104,
xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.
xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106,
xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107,
xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115, and wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 13.

One embodiment of the invention relates to the use of a cleaning composition comprising a DNase and a glycosyl hydrolase, preferably a Glyco_hydro_114 glycosyl hydrolase for deep cleaning of an item or reduction of redeposition or malodor, wherein the glycosyl hydrolase is selected from the group of polypeptides consisting of polypeptides comprising an amino acid sequence having;

i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84, ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85, iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86, iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87, v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.

xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115, and wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 65.

One embodiment of the invention relates to the use of a cleaning composition comprising a DNase and a glycosyl hydrolase, preferably a Glyco_hydro_114 glycosyl hydrolase for deep cleaning of an item or reduction of redeposition or malodor, wherein the glycosyl hydrolase is selected from the group of polypeptides consisting of polypeptides comprising an amino acid sequence having;

i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84, ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85, iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86, iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87, v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.

xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115, and wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 66.

One embodiment of the invention relates to the use of a cleaning composition comprising a DNase and a glycosyl hydrolase, preferably a Glyco_hydro_114 glycosyl hydrolase for deep cleaning of an item or reduction of redeposition or malodor, wherein the glycosyl hydrolase is selected from the group of polypeptides consisting of polypeptides comprising an amino acid sequence having;

i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84, ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85, iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86, iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87, v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102,
xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103,
xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104,
xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.
xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106,
xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107,
xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108,
xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109,
xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110,
xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111,
xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112,
xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113,
xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and
xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115,
wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 67.

One embodiment of the invention relates to the use of a cleaning composition comprising a DNase and a glycosyl hydrolase, preferably a Glyco_hydro_114 glycosyl hydrolase for deep cleaning of an item or reduction of redeposition or malodor, wherein the glycosyl hydrolase is selected from the group of polypeptides consisting of polypeptides comprising an amino acid sequence having;

i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84,
ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85,
iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86,
iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87,
v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88,
vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89,
vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90,
viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91,
ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92,
x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93,
xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94,
xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95,
xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96,
xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97,
xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98,
xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99,
xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.

xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115, wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 68.

The invention further relates to a method of deep cleaning on an item, comprising the steps of:
a) contacting the item with a cleaning composition comprises a DNase, a Glyco_hydro_114 glycosyl hydrolase and a cleaning component; and
b) and optionally rinsing the item, wherein the item is preferably a textile.

The invention further relates to a method of deep cleaning on an item, comprising the steps of:
a) contacting the item with a cleaning composition comprises a DNase, wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 13, a glycosyl hydrolase, preferably a Glyco_hydro_114 glycosyl hydrolase, wherein the glycosyl hydrolase is selected from the group consisting of polypeptides having;

i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84, ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85, iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86, iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87, v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.

xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115, and a cleaning component;

b) and optionally rinsing the item, wherein the item is preferably a textile.

The invention further relates to a method of deep cleaning on an item, comprising the steps of:

a) contacting the item with a cleaning composition comprises a DNase, wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 65, a glycosyl hydrolase, preferably a Glyco_hydro_114 glycosyl hydrolase, wherein the glycosyl hydrolase is selected from the group consisting of polypeptides having;

i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84, ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85, iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86, iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87, v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.

xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115, and a cleaning component;

b) and optionally rinsing the item, wherein the item is preferably a textile.

The invention further relates to a method of deep cleaning on an item, comprising the steps of:

a) contacting the item with a cleaning composition comprises a DNase, wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 66, a glycosyl hydrolase, preferably a Glyco_hydro_114 glycosyl hydrolase, wherein the glycosyl hydrolase is selected from the group consisting of polypeptides having;

i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84, ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85, iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86, iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87, v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.

xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115, and a cleaning component;

b) and optionally rinsing the item, wherein the item is preferably a textile.

The invention further relates to a method of deep cleaning on an item, comprising the steps of:

a) contacting the item with a cleaning composition comprises a DNase, wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 67, a glycosyl hydrolase, preferably a Glyco_hydro_114 glycosyl hydrolase, wherein the glycosyl hydrolase is selected from the group consisting of polypeptides having;

i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84,
ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85,
iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86,
iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87,
v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88,
vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89,
vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90,
viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91,
ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92,
x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93,
xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94,
xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95,
xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96,
xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97,
xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98,
xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99,
xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100,
xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101,
xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102,
xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103,
xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104,
xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.
xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106,
xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107,
xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108,
xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109,
xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110,
xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111,
xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112,
xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113,
xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and
xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115, and a cleaning component;
b) and optionally rinsing the item, wherein the item is preferably a textile.

The invention further relates to a method of deep cleaning on an item, comprising the steps of:
a) contacting the item with a cleaning composition comprises a DNase, wherein the DNase has at least 60%, at least 65%, at least 70%, at least 75%, at least 80%, at least 85%, at least 90%, at least 95%, at least 98%, at least 99% or 100% sequence identity to the amino acid sequence shown in SEQ ID NO 68, a glycosyl hydrolase, preferably a Glyco_hydro_114 glycosyl hydrolase, wherein the glycosyl hydrolase is selected from the group consisting of polypeptides having;
  i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84,
  ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85,
  iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86,
  iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87,
  v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88,
  vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89,
  vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90,
  viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91,
  ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92,
  x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93,
  xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94,
  xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95,
  xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96,
  xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97,
  xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98,
  xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99,
  xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100,
  xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101,
  xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102,
  xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103,
  xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104,
  xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.
  xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106,
  xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107,
  xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108,
  xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109,
  xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110,
  xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111,
  xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112,
  xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113,
  xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115, and a cleaning component;

b) and optionally rinsing the item, wherein the item is preferably a textile.

The invention further relates to a kit intended for deep cleaning, wherein the kit comprises a solution of an enzyme mixture comprising a DNase and a Glyco_hydro_114 glycosyl hydrolase. The DNase is preferably selected from polypeptides having at least 60%, at least 65%, at least 70%, at least 75%, at least 80%, at least 85%, at least 90%, at least 95%, at least 98%, at least 99% or 100% sequence identity to the amino acid sequence shown in SEQ ID NO 13, SEQ ID NO 65, SEQ ID NO 66, SEQ ID NO 67 and SEQ ID NO 68, and the Glyco_hydro_114 glycosyl hydrolase is preferably selected from from a polypeptide comprising;

i) at least 60%, at least 65%, at least 70%, at least 75%, at least 80%, at least 85%, at least 90%, at least 95%, at least 98%, at least 99% or 100% sequence identity to the polypeptide shown in SEQ ID NO: 84, ii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 85, iii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 86, iv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 87, v) at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, vi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, vii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, viii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, ix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, x) at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, xi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 94.

xii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, xiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, xiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, xv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, xvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, xvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, xviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, xix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, xx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, xxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, xxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 105.

xxiii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, xxvii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, xxviii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, xxix) at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, xxx) at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, xxxi) at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) at least 60%, at least 65%, at least 70%, at least 75%, at least 80%, at least 85%, at least 90%, at least 95%, at least 98%, at least 99% or 100% sequence identity to the polypeptide shown in SEQ ID NO: 115, The invention is further described in the following paragraphs.

Paragraph 1 A cleaning composition comprising at least 0.001 ppm DNase and at least 0.001 ppm glycosyl hydrolase and a cleaning component, wherein the cleaning component is selected from
a. 0.1 to 15 wt % of at least one a surfactant;
b. 0.5 to 20 wt % of at least one builder; and
c. 0.01 to 10 wt % of at least one bleach component.

Paragraph 2 The cleaning composition according to paragraph 1, wherein the DNase comprises one or both of the motif(s) [D/M/L][S/T]GYSR[D/N] (SEQ ID NO: 73), ASXNRSKG (SEQ ID NO: 74) and the glycosyl hydrolase comprises one or both the motifs GX[FY][LYF]D (SEQ ID NO 82) or AYX[SET]XX[EAS] (SEQ ID NO: 83).

Paragraph 3 The cleaning composition according to paragraph 1 or 2, wherein the DNase is selected from the group of polypeptides having DNase activity consisting of:

a) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 1, b) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 2, c) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 3, d) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 4, e) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 5, f) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 6, g) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 7, h) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 8, i) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 9, j) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 10, k) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 11, l) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 12, m) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 13, n) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 14, o) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 15, p) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 16, q) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 17, r) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 18, s) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 19, t) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 20,
u) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 21,
v) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 22,
w) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 23,
x) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 24,
y) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 25, and
wherein the glycosyl hydrolase is selected from the group of polypeptides having glycosyl hydrolase activity consisting of;
i) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 84,
ii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 85,
iii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 86,
iv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 87,
v) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 88,
vi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 89,
vii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 90,
viii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 91,
ix) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 92,
x) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 93,
xi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 94,
xii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 95,
xiii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 96,
xiv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 97,
xv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 98,
xvi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 99,
xvii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 100,
xviii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 101,
xix) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 102,
xx) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 103,
xxi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, xxii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 105, xxiii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, xxvii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, xxviii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, xxix) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, xxx) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, xxxi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 115.

Paragraph 4 The a cleaning composition according to paragraph 1, wherein the DNase comprises one or both of the motif(s) [V/I]PL[S/A]NAWK (SEQ ID NO: 75) or NPQL (SEQ ID NO: 76) and the glycosyl hydrolase comprises one or both the motifs GX[FY][LYF]D (SEQ ID NO 82) or AYX[SET]XX[EAS] (SEQ ID NO: 83).

Paragraph 5 The cleaning composition according to paragraph 1 or 4, wherein the DNase is selected from the group of polypeptides consisting of:

a) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 26, b) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 27, c) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 28, d) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 29, e) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 30, f) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 31, g) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 32, h) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 33, i) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 34, j) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 35, k) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 36, l) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 37, m) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 38;

and wherein the glycosyl hydrolase is selected from the group of polypeptides having glycosyl hydrolase activity consisting of;

i) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 84, ii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 85, iii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 86, iv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 87, v) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, vi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, vii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, viii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, ix) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, x) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, xi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, xii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, xiii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, xiv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, xv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, xvi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, xvii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, xviii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, xix) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, xx) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, xxi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, xxii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 105, xxiii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 109,
- xxvii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 110,
- xxviii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 111,
- xxix) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 112,
- xxx) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 113,
- xxxi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and
- xxxii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 115.

Paragraph 6 The cleaning composition according to paragraph 1 wherein the DNase comprises one or both of the motif(s) P[Q/E]L[W/Y] (SEQ ID NO: 77) or [K/H/E]NAW (SEQ ID NO: 78) and the glycosyl hydrolase comprises one or both the motifs GX[FY][LYF]D (SEQ ID NO 82) or AYX[SET]XX[EAS] (SEQ ID NO: 83).

Paragraph 7 The cleaning composition according to paragraph 1 or 6, wherein the DNase is selected from the group of polypeptides consisting of:
- a) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 39,
- b) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 40,
- c) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 41,
- d) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 42,
- e) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 43
- f) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 44,
- g) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 45,
- h) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 46,
- i) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 47,
- j) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 48,
- k) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 49,
- l) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 50,
- m) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 51 and wherein the glycosyl hydrolase is selected from the group of polypeptides having glycosyl hydrolase activity consisting of;
- i) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 84,
- ii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 85,
- iii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 86,
- iv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 87,
- v) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 88, vi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 89, vii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 90, viii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 91, ix) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 92, x) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 93, xi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 94, xii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 95, xiii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 96, xiv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 97, xv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 98, xvi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 99, xvii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 100, xviii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 101, xix) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 102, xx) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 103, xxi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 104, xxii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 105, xxiii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 106, xxiv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 107, xxv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 108, xxvi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 109, xxvii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 110, xxviii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 111, xxix) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 112, xxx) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 113, xxxi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and xxxii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 115.

Paragraph 8 The cleaning composition according to paragraph 1 wherein the DNase is selected from the group consisting of:
  a) polypeptide obtainable from *Bacillus licheniformis* having a sequence identity to the polypeptide shown in SEQ ID NO: 65 of at least 80%, at least 85%, at least 90%, at least 95%, at least 96%, at least 97%, at least 98%, at least 99%, or 100% and which have DNase activity,
  b) polypeptide obtainable from *Bacillus subtilis* having a sequence identity to the polypeptide shown in SEQ ID NO: 66 of at least 80%, at least 85%, at least 90%, at least 95%, at least 96%, at least 97%, at least 98%, at least 99%, or 100% and which have DNase activity,
  c) polypeptide obtainable from *Aspergillus oryzae* having a sequence identity to the polypeptide shown in SEQ ID NO: 67 of at least 80%, at least 85%, at least 90%, at least 95%, at least 96%, at least 97%, at least 98%, at least 99%, or 100% and which have DNase activity,
  d) polypeptide obtainable from *Trichoderma harzianum* having a sequence identity to the polypeptide shown in SEQ ID NO: 68 of at least 80%, at least 85%, at least 90%, at least 95%, at least 96%, at least 97%, at least 98%, at least 99%, or 100% and which have DNase activity, and wherein the glycosyl hydrolase is selected from the group of polypeptides having glycosyl hydrolase activity consisting of;
  i) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 84,
  ii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 85,
  iii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 86,
  iv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 87,
  v) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 88,
  vi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 89,
  vii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 90,
  viii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 91,
  ix) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 92,
  x) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 93,
  xi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 94,
  xii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 95,
  xiii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 96,
  xiv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 97,
  xv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 98,
  xvi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 99,
  xvii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 100,
  xviii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 101,
  xix) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 102,
  xx) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 103,
  xxi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 104,
xxii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 105,
xxiii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 106,
xxiv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 107,
xxv) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 108,
xxvi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 109,
xxvii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 110,
xxviii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 111,
xxix) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 112,
xxx) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 113,
xxxi) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 114, and
xxxii) a polypeptide having at least 60%, at least 65%, at least 70%, at least 75%, at least 80%, at least 85%, at least 90%, at least 95%, at least 98%, at least 99% or 100% sequence identity to the polypeptide shown in SEQ ID NO: 115.

Paragraph 9 The cleaning composition according to any of the preceding paragraphs, wherein the composition further comprises at least one protease selected from,
i) a protease variant of a protease parent, wherein the protease variant comprises one or more alteration(s) compared to a protease shown in SEQ ID NO 79 or SEQ ID NO 80 in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269, wherein the positions correspond to the positions of the protease shown in SEQ ID NO 79 and wherein the protease variant has at least 80% sequence identity to SEQ ID NO 79, SEQ ID NO 80 or SEQ ID NO 81;
ii) a protease variant of a protease parent, wherein the protease variant comprises one or more mutation selected from the group consisting of S3T, V4I, S9R, S9E, A15T, S24G, S24R, K27R, N42R, S55P, G59E, G59D, N60D, N60E, V66A, N74D, S85R, A96S, S97G, S97D, S97A, S97SD, S99E, S99D, S99G, S99M, S99N, S99R, S99H, S101A, V102I, V102Y, V102N, S104A, G116V, G116R, H118D, H118N, A120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A and R269H, wherein the positions correspond to the positions of the protease shown in SEQ ID NO 79, wherein the protease variant has at least 80% sequence identity to SEQ ID NO 79, SEQ ID NO 80 or SEQ ID NO 81;
iii) a protease comprising a substitution at one or more positions corresponding to positions 171, 173, 175, 179, or 180 of SEQ ID NO: 81, compared to the protease shown in SEQ ID NO 81, wherein the protease variant has a sequence identity of at least 75% but less than 100% to amino acid 1 to 311 of SEQ ID NO 81; and
iv) a protease comprising the amino acid sequence shown in SEQ ID NO 79, 80 or 81 or a protease having at least 80% sequence identity to; the polypeptide comprising amino acids 1-269 of SEQ ID NO 79, the polypeptide comprising amino acids 1-311 of SEQ ID NO 81 or the polypeptide comprising amino acids 1-275 of SEQ ID NO 80.

Paragraph 10 The use of a composition according to any of the previous paragraphs for deep cleaning of an item, wherein the item is a textile or a surface.

Paragraph 11 A method of formulating a cleaning composition comprising adding a DNase, a glycosyl hydrolase and at least one cleaning component.

Paragraph 12 A kit intended for deep cleaning, wherein the kit comprises a solution of an enzyme mixture comprising a DNase, glycosyl hydrolase and optionally a protease.

Paragraph 13 A method of deep cleaning on an item, comprising the steps of:
a) contacting the item with a solution comprising an enzyme mixture comprising a DNase and a glycosyl hydrolase and optionally a protease; and a cleaning component, wherein the cleaning component is selected from 0.1 to 15 wt % of at least one a surfactant; 0.5 to 20 wt % of at least one builder; and 0.01 to 10 wt % of at least one bleach component; and
b) and optionally rinsing the item, wherein the item is preferably a textile.

Definitions

Nomenclature

For purposes of the present invention, the nomenclature [E/Q] means that the amino acid at this position may be a glutamic acid (Glu, E) or a glutamine (Gln, Q). Likewise, the nomenclature [V/G/A/I] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

The term "biofilm" is produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community. On laundry biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp. On hard surfaces biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis, Staphylococcus aureus* and *Stenotrophomonas* sp. In one aspect, the biofilm producing strain is *Brevundimonas* sp. In one aspect, the biofilm producing strain is *Pseudomonas* particularly, *Pseudomonas aeruginosa Pseudomonas alcaliphila* or *Pseudomonas fluorescens*. In one aspect, the biofilm producing strain is *Staphylococcus aureus*.

By the term "deep cleaning" is meant disruption or removal of components of organic matter, e.g. biofilm, such as polysaccharides e.g. pel, proteins, DNA, soil or other components present in the organic matter.

Cleaning component: The cleaning component e.g. the detergent adjunct ingredient is different to the DNase and Glyco_hydro_114 glycosyl hydrolase enzymes. The precise nature of these additional cleaning components e.g. adjunct components, and levels of incorporation thereof, will depend on the physical form of the composition and the nature of the operation for which it is to be used. Suitable cleaning components e.g. adjunct materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, antifoaming agents, dispersants, processing aids, and/or pigments.

Cleaning composition: The term "cleaning composition" refers to compositions that find use in the removal of undesired compounds from items to be cleaned, such as textiles. The cleaning composition may be used to e.g. clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pretreatment). In addition to containing the enzymes, the cleaning composition may contain one or more additional enzymes (such as amylases, lipases, cutinases, cellulases, endoglucanases, xyloglucanases, pectinases, pectin lyases, xanthanases, peroxidases, haloperoxygenases, catalases and mannanases, or any mixture thereof), and/or cleaning components e.g. detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides. Textile care benefits, which are not directly related to catalytic stain removal or prevention of redeposition of soils, are also important for enzyme detergency benefits. Examples of such textile care benefits are prevention or reduction of dye transfer from one textile to another textile or another part of the same textile (an effect that is also termed dye transfer inhibition or anti-backstaining), removal of protruding or broken fibers from a textile surface to decrease pilling tendencies or remove already existing pills or fuzz (an effect that also is termed anti-pilling), improvement of the textile-softness, colour clarification of the textile and removal of particulate soils which are trapped in the fibers of the textile. Enzymatic bleaching is a further enzyme detergency benefit where the catalytic activity generally is used to catalyze the formation of bleaching component such as hydrogen peroxide or other peroxides or other bleaching species."

The term "Hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, cutlery such as spoons, knives, forks, serving utensils, ceramics, plastics, metals, china, glass and acrylics.

The term "wash performance" is used as an enzyme's ability to remove stains present on the object to be cleaned during e.g. wash or hard surface cleaning.

The term "Whiteness" is defined herein as a greying, yellowing of a textile. Loss of whiteness may be due to removal of optical brighteners/hueing agents. Greying and yellowing can be due to soil redeposition, body soils, colouring from e.g. iron and copper ions or dye transfer. Whiteness might include one or several issues from the list below: colourant or dye effects; incomplete stain removal (e.g. body soils, sebum etc.); redeposition (greying, yellowing or other discolourations of the object) (removed soils reassociate with other parts of textile, soiled or unsoiled); chemical changes in textile during application; and clarification or brightening of colours.

The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

By the term "malodor" is meant an odor which is not desired on clean items. The cleaned item should smell fresh and clean without malodors adhered to the item. One example of malodor is compounds with an unpleasant smell, which may be produced by microorganisms. Another example is unpleasant smells can be sweat or body odor adhered to an item which has been in contact with human or animal. Another example of malodor can be the odor from spices, which sticks to items for example curry or other exotic spices which smells strongly.

The term "mature polypeptide" means a polypeptide in its final form following translation and any post-translational modifications, such as N-terminal processing, C-terminal truncation, glycosylation, phosphorylation, etc.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 6.6.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g. polyamide fiber, acrylic fiber, polyester fiber, polyvinyl chloride fiber, polyurethane fiber, polyurea fiber, aramid fiber), and/or cellulose-containing fiber (e.g. rayon/viscose, ramie, flax/linen, jute, cellulose acetate fiber, lyocell). Fabric may be conventional washable laundry, for example stained household laundry. When the term fabric or garment is used it is intended to include the broader term textiles as well.

The term "variant" means a polypeptide having the activity of the parent or precursor polypeptide and comprising an alteration, i.e., a substitution, insertion, and/or deletion, at one or more (e.g., several) positions compared to the precursor or parent polypeptide. A substitution means replacement of the amino acid occupying a position with a different amino acid; a deletion means removal of the amino acid occupying a position; and an insertion means adding an amino acid adjacent to and immediately following the amino acid occupying a position.

EXAMPLES

Assays

Assay I: Testing of DNase Activity

DNase activity was determined on DNase Test Agar with Methyl Green (BD, Franklin Lakes, N.J., USA), which was prepared according to the manual from supplier. Briefly, 21 g of agar was dissolved in 500 ml water and then autoclaved for 15 min at 121° C. Autoclaved agar was temperated to 48° C. in water bath, and 20 ml of agar was poured into petridishes with and allowed to solidify by incubation o/n at room temperature. On solidified agar plates, 5 µl of enzyme solutions are added and DNase activity is observed as colorless zones around the spotted enzyme solutions.

Assay II

DNase activity may be determined by fluorescence using a fluorescence-quenched DNA oligonucleotide probe. This probe emits a signal after nuclease degradation according to the manual from the supplier (DNase alert kit, Integrated DNA Technology, Coralville, Iowa, USA). Briefly, 5 µl of the substrate is added to 95 µl of DNase. If the signal is too high, further dilutions of DNase are performed in a suitable buffer. Kinetic curves are measured for 20 min at 22° C. using a Clariostar microplate reader (536 nm excitation, 556 nm emission).

Assay III: Testing Activity of Glyco_Hydro_114 Glycosyl Hydrolases

The activity of the Glyco_hydro_114 glycosyl hydrolases of the invention may be measured in a pNP-acetate assay as described in Marmont et. al. (2017) "PelA and PelB proteins form a modification and secretion complex essential for Pel polysaccharide-dependent biofilm formation in *Pseudomonas aeruginosa*", J. Biol. Chem. 292, 19411-19422 or as described by Colvin, K. M., et. al (2013) "PelA deacetylase activity is required for Pel polysaccharide synthesis in *Pseudomonas aeruginosa*". J. Bacteriol. 195, 2329-2339.

Automatic Mechanical Stress Assay (AMSA) for Laundry

In order to assess the wash performance in laundry, washing experiments are performed using the Automatic Mechanical Stress Assay (AMSA). With the AMSA, the wash performance of many small volume enzyme-detergent solutions can be examined. The AMSA plate has a number of slots for test solutions and a lid that firmly squeezes the textile to be washed against the slot openings. During the wash, the plate, test solutions, textile and lid are vigorously shaken to bring the test solution in contact with the textile and apply mechanical stress in a regular, periodic, oscillating manner. For further description see WO02/42740 especially the paragraph "Special method embodiments" at page 23-24.

The laundry experiments may be conducted under the experimental conditions specified below:

| | |
|---|---|
| Detergent dosage | 5 g/L (liquid detergent) |
| | 2.5 g/L (powder detergent) |
| Test solution volume | 160 micro L |
| pH | Adjusted to pH 7 or pH 6 (liquid detergent) |
| | As is (powder detergent) |
| Wash time | 20 minutes |
| Temperature | 60° C., 40° C. and 20° C. or 15° C. |
| Water hardness | 15° dH |

Model detergents and test materials are as follows:

| | |
|---|---|
| Laundry liquid model detergent | Sodium alkylethoxy sulfate (C-9-15, 2EO) 6.0% |
| | Sodium dodecyl benzene sulfonate 3.0% |
| | Sodium toluene sulfonate 3.0% |
| | Oleic acid 2.0% |
| | Primary alcohol ethoxylate (C12-15, 7EO) 3.0% |
| | Primary alcohol ethoxylate (C12-15, 3EO) 2.5% |
| | Ethanol 0.5% |
| | Monopropylene glycol 2.0% |
| | Tri-sodium citrate dihydrate 4.0% |
| | Triethanolamine 0.4% |
| | De-ionized water ad 100% |
| | pH adjusted to 8.5 with NaOH |
| Laundry powder model detergent | Sodium citrate dihydrate 32.3% |
| | Sodium-LAS 24.2% |
| | Sodium lauryl sulfate 32.2% |
| | Neodol 25-7 (alcohol ethoxylate) 6.4% |
| | Sodium sulfate 4.9% |

Water hardness was adjusted to 15° dH by addition of $CaCl_2$, $MgCl_2$, and $NaHCO_3$ ($Ca^{2+}:Mg^{2+}=4:1:7.5$) to the test system. After washing the textiles were flushed in tap water and dried.

The wash performance is measured as the brightness of the colour of the textile washed. Brightness can also be expressed as the intensity of the light reflected from the sample when illuminated with white light. When the sample is stained the intensity of the reflected light is lower, than that of a clean sample. Therefore, the intensity of the reflected light can be used to measure wash performance.

Colour measurements are made with a professional flat-bed scanner (Kodak iQsmart, Kodak, Midtager 29, DK-2605 Brondby, Denmark), which is used to capture an image of the washed textile.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int=\sqrt{r^2+g^2+b^2}.$$

Mini Wash Assay

Wash performance is assessed in laundry wash experiment using a Mini wash assay, which is a test method where soiled textile is continuously is lifted up and down into the test solution and subsequently rinsed.

The wash experiment is conducted under various experimental conditions one examples specified below:

| | |
|---|---|
| Detergent | Model A detergent |
| | Model detergent A wash liquor (100%) is prepared by dissolving 3.33 g/l of model detergent A containing 12% LAS, 1.1% AEO Biosoft N25-7 (NI), 7% AEOS (SLES), 6% MPG, 3% ethanol, 3% TEA (triethanolamine), 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w (weight volume) in water with hardness 15 dH. |
| Detergent dose | 3.33 g/l |
| pH | Example: "as is" in the current detergent solution and is not adjusted. |
| Water hardness | 15° dH, adjusted by adding $CaCl_2*2H_2O$, $MgCl_2*6H_2O$ and $NaHCO_3$ (4:1:7.5) to milli-Q water. |
| Enzymes | Enzyme blend according to the invention |
| Enzyme conc. | Example 2.5 nM, 5 nM, 10 nM, 30 nM, 60 nM |
| Test material | Example: Biofilm or EPS swatches |
| Temperature | e.g. 15° C., 20° C., 30° C., 40° C. or 60° C. |
| Test system | Soiled textile continuously lifted up and down into the test solutions, 50 times per minute. The test solutions are kept in 125 ml glass beakers. After wash of the textiles are continuously lifted up and down into tap water, aprox. 50 times per minute. |

Test materials may be obtained from EMPA Testmaterials AG Mövenstrasse 12, CH-9015 St. Gallen, Switzerland, from Center for Testmaterials BV, P.O. Box 120, 3133 KT Vlaardingen, the Netherlands, and WFK Testgewebe GmbH, Christenfeld 10, D-41379 Bruggen, Germany.

The textiles are subsequently air-dried and the wash performance is measured as the brightness of the colour of these textiles. Brightness can also be expressed as the Remission (R), which is a measure for the light reflected or emitted from the test material when illuminated with white light. The Remission (R) of the textiles is measured at 460 nm using a Zeiss MCS 521 VIS spectrophotometer. The measurements are done according to the manufacturer's protocol.

Example 1

Synergistic Effect Between PelAs (Glyco_Hydro_114 Glycosyl Hydrolase) and DNase on Deep-Cleaning in Liquid Model Detergent on EPS Swatches A crude extract of biofilm EPS (containing Pel and eDNA) was prepared from *Pseudomonas aeruginosa* PA14 (DSM 19882) as follows; The strain was restreaked on LB Agar (pH 7.3) and incubated for 3 days at 30° C. 500 mL of T-broth (10 g/L Bacto™ Tryptone (211705, BD), 5 g/L sodium chloride (31434, Sigma-Aldrich)) was then inoculated and incubated statically for 6 days at 37° C. The biofilm pellicle was carefully removed from the flask, and pelleted by centrifugation (5 min, 10000 g, 25° C.). The pellet was then resuspended in 3M NaCl, vortexed vigorously and incubated for 15 min at ambient temperature to extract the surface-associated polymer. The cells were then re-pelleted (5 min, 10000 g, 25° C.) and the EPS-containing supernatant was retrieved. The extract was stored at −200C until further use (termed EPS extract). For testing wash performance, 50 ul aliquots of the crude EPS were spotted on sterile textile swatches (WFK20A) and incubated for 15 min at ambient temperature. Swatches spotted with sterile 3M NaCl were included as controls. The swatches (sterile or with EPS) were placed in 50 mL test tubes and 10 mL of wash liquor (15°dH water with 0.2 g/L iron(III) oxide nano-powder (544884; Sigma-Aldrich) and 3.33 g/L liquid model A detergent (12% LAS, 11% AEO Biosoft N25-7 (NI), 5% AEOS (SLES), 6% MPG (monopropylene glycol), 3% ethanol, 3% TEA, 2.75% coco soap, 2.75% soya soap, 2% glycerol, 2% sodium hydroxide, 2% sodium citrate, 1% sodium formate, 0.2% DTMPA and 0.2% PCA (all percentages are w/w)) and 0.2 µg/ml enzyme(s) was added to each tube. Washes without enzyme were included as controls. The test tubes were placed in a Stuart rotator and incubated for 1 hour at 30° C. at 20 rpm. The wash liquor was then removed, and the swatches were rinsed twice with 15°dH water and dried on filter paper over night. The tristimulus light intensity (Y) values were measured using a Handheld Minolta CR-300, and are displayed in table 1. Wash performance, WP ($\Delta Y = Y_{(swatch\ washed\ with\ enzyme)} - Y_{(swatch\ washed\ without\ enzyme)}$) and the wash performance synergies, $WP_{syn}$ ($\Delta Y_{(cocktail)} - \Delta Y_{(sum\ of\ individual\ enzyme\ treatments)}$) are also indicated.

TABLE 1

Synergistic effect of PelAs (Glyco_hydro_114 glycosyl hydrolases) and DNase on deep-cleaning in model A detergent on EPS swatches.

| Swatch | Enzyme | Enzyme conc. (µg/ml) | Avg. Y values | WP (ΔY) | WPsyn |
|---|---|---|---|---|---|
| Wfk20A, no EPS | no enzyme | 0 | 82.2 | | |
| Wfk20A, EPS swatch | no enzyme | 0 | 44.2 | | |
| Wfk20A, EPS swatch | DNase (SEQ ID NO 67) | 0.2 | 64.4 | 20.2 | |
| Wfk20A, EPS swatch | DNase (SEQ ID NO 13) | 0.2 | 62.4 | 18.2 | |
| Wfk20A, EPS swatch | PelA (SEQ ID NO 84) | 0.2 | 49 | 4.8 | |
| Wfk20A, EPS swatch | PelA (SEQ ID NO 87) | 0.2 | 47.7 | 3.5 | |
| Wfk20A, EPS swatch | PelA (SEQ ID NO 84) + DNase (SEQ ID NO 67) | 0.2 + 0.2 | 72.3 | 28.1 | 3.1 |
| Wfk20A, EPS swatch | PelA (SEQ ID NO 87) + DNase (SEQ ID NO 67) | 0.2 + 0.2 | 79.9 | 35.7 | 12 |
| Wfk20A, EPS swatch | PelA (SEQ ID NO 84) + DNase (SEQ ID NO 13) | 0.2 + 0.2 | 74.4 | 30.2 | 7.2 |
| Wfk20A, EPS swatch | PelA (SEQ ID NO 87) + DNase (SEQ ID NO 13) | 0.2 + 0.2 | 80.4 | 36.2 | 14.5 |

As seen in table 1, an enzyme cocktail comprising PelA (Glyco_hydro_114 glycosyl hydrolases) and DNase provides superior deep-cleaning properties in model A detergent as compared to the individual enzymes, given that the wash performance of the enzyme cocktail (ΔY (cocktail)) clearly exceed the sum of the performances seen for of the individual enzymes (ΔY (sum of individual enzyme treatments)), i.e. $WP_{syn} > 0$. This clearly suggests that there is a synergetic effect between the two enzymes on the deep-cleaning properties in model A.

Example 2

Synergistic Effect Between PelAs
(Glyco_Hydro_114 Glycosyl Hydrolases) and
DNase on Deep-Cleaning in Liquid Model
Detergent on EPS Swatches Crude biofilm EPS was extracted from *Pseudomonas aeruginosa* PA14 (DSM 19882) and wash performances were tested as described in the example above. The tristimulus light intensity (Y) values were measured using a Handheld Minolta CR-300, and are displayed in table 2. Wash performance, WP ($\Delta Y = Y_{(swatch\ washed\ with\ enzyme)} - Y_{(swatch\ washed\ without\ enzyme)}$) and the wash performance synergies, $WP_{syn}$ ($\Delta Y_{(cocktail)} - \Delta Y_{(sum\ of\ individual\ enzyme\ treatments)}$) are also presented.

TABLE 2

Synergistic effect of PelA (Glyco_hydro_114 glycosyl hydrolases) and DNase on deep-cleaning in model A detergent on EPS swatches.

| Swatch | Enzyme | Enzyme concentration (µg/ml) | Y values | WP(ΔY) | WP$_{Syn}$ |
|---|---|---|---|---|---|
| Wfk20A, no EPS | no enzyme | 0 | 75.2 | | |
| Wfk20A, EPS swatch | no enzyme | 0 | 49.1 | | |
| Wfk20A, EPS swatch | DNase (SEQ ID NO 67) | 0.002 | 62.5 | 13.4 | |
| Wfk20A, EPS swatch | DNase (SEQ ID NO 13) | 0.002 | 60.5 | 11.4 | |
| Wfk20A, EPS swatch | PelA (SEQ ID NO 105) | 20 | 50.8 | 1.7 | |
| Wfk20A, EPS swatch | PelA (SEQ ID NO 105) + DNase (SEQ ID NO 67) | 0.002 + 20 | 66.8 | 17.7 | 2.6 |
| Wfk20A, EPS swatch | PelA (SEQ ID NO 105) + DNase (SEQ ID NO 13) | 0.002 + 20 | 67.9 | 18.8 | 5.7 |

As seen in table 2, an enzyme cocktail comprising PelA (Glyco_hydro_114 glycosyl hydrolases) and DNase also provides superior deep-cleaning properties in model A detergent as compared to the individual enzymes, given that $WP_{syn} > 0$. This clearly suggests that there is a synergetic effect between the two enzymes on the deep-cleaning properties in model A.

The invention claimed is:

1. A cleaning composition comprising a DNase, a Glyco_hydro_114 glycosyl hydrolase and a cleaning component, wherein the DNase has at least 80% sequence identity to the polypeptide shown in SEQ ID NO: 67, and the Glyco_hydro_114 glycosyl hydrolase is a PelA enzyme with at least 80% sequence identity to the polypeptide shown in SEQ ID NO: 87.

2. The cleaning composition according to claim 1, wherein the DNase is microbial.

3. The cleaning composition according to claim 1, wherein the DNase has at least 85% sequence identity to the amino acid sequence shown in SEQ ID NO: 67.

4. The cleaning composition according to claim 1, wherein the DNase has at least 90% sequence identity to the amino acid sequence shown in SEQ ID NO: 67.

5. The cleaning composition according to claim 1, wherein the glycosyl hydrolase is selected from the group consisting of:
   a) a polypeptide having at least 80% sequence identity to the polypeptide shown in SEQ ID NO: 87,
   b) a polypeptide having at least 80% sequence identity to the polypeptide shown in SEQ ID NO: 89,
   c) a polypeptide having at least 80% sequence identity to the polypeptide shown in SEQ ID NO: 96,
   d) a polypeptide having at least 80% sequence identity to the polypeptide shown in SEQ ID NO: 97,
   e) a polypeptide having at least 80% sequence identity to the polypeptide shown in SEQ ID NO: 98,
   f) a polypeptide having at least 80% sequence identity to the polypeptide shown in SEQ ID NO: 99.

6. The cleaning composition according to claim 1, wherein the amount of DNase in the composition is from 0.01 to 1000 ppm and the amount of glycosyl hydrolase is from 0.01 to 1000 ppm.

7. The cleaning composition according to claim 1, wherein the cleaning component is selected from surfactants, builders and bleach components.

8. A method of formulating a cleaning composition according to claim 1, the method comprising adding the DNase, the glycosyl hydrolase, and at least one cleaning component according to claim 1.

9. A kit intended for deep cleaning, wherein the kit comprises a solution of an enzyme mixture comprising a DNase, a Glyco_hydro_114 glycosyl hydrolase and optionally a protease, wherein the DNase has at least 80% sequence identity to the polypeptide shown in SEQ ID NO: 67, and the Glyco_hydro_114 glycosyl hydrolase is a PelA enzyme with at least 80% sequence identity to the polypeptide shown in SEQ ID NO: 87.

10. A method of deep cleaning on an item, comprising the steps of:
   a) contacting the item with a cleaning composition according to claim 1; and
   b) optionally rinsing the item,
   wherein the item is a textile.

11. The method of claim 10, wherein the cleaning composition comprises a DNase which has at least 85% sequence identity to the amino acid sequence shown in SEQ ID NO: 67.

12. The method of claim 10, wherein the cleaning composition comprises a DNase which has at least 90% sequence identity to the amino acid sequence shown in SEQ ID NO: 67.

* * * * *

SEQUENCE LISTING

```
<160> NUMBER OF SEQ ID NOS: 115

<210> SEQ ID NO 1
<211> LENGTH: 182
<212> TYPE: PRT
<213> ORGANISM: Bacillus sp-62451

<400> SEQUENCE: 1

Leu Pro Pro Asp Leu Pro Ser Lys Ser Thr Thr Gln Ala Gln Leu Asn
1               5                   10                  15

Ser Leu Asn Val Lys Asn Glu Glu Ser Met Ser Gly Tyr Ser Arg Glu
            20                  25                  30

Lys Phe Pro His Trp Ile Ser Gln Gly Asp Gly Cys Asp Thr Arg Gln
        35                  40                  45

Val Ile Leu Lys Arg Asp Ala Asp Asn Tyr Ser Gly Asn Cys Pro Val
    50                  55                  60

Thr Ser Gly Lys Trp Tyr Ser Tyr Tyr Asp Gly Ile Thr Phe Asn Asp
65                  70                  75                  80

Pro Ser Gln Leu Asp Ile Asp His Val Val Pro Leu Ala Glu Ala Trp
                85                  90                  95
```

```
Arg Ser Gly Ala Ser Ser Trp Ser Thr Ala Lys Arg Glu Asp Phe Ala
            100                 105                 110

Asn Asp Leu Asn Gly Pro Gln Leu Ile Ala Val Ser Ala Ser Ser Asn
            115                 120                 125

Arg Ser Lys Gly Asp Gln Asp Pro Ser Thr Trp Gln Pro Pro Arg Ala
        130                 135                 140

Gly Ala Asn Cys Ala Tyr Ala Lys Met Trp Ile Asn Thr Lys Tyr Asn
145                 150                 155                 160

Trp Gly Leu His Leu Gln Ser Ser Glu Lys Thr Ala Leu Gln Gly Met
                165                 170                 175

Leu Asn Ser Cys Ser Tyr
            180

<210> SEQ ID NO 2
<211> LENGTH: 182
<212> TYPE: PRT
<213> ORGANISM: Bacillus horikoshii

<400> SEQUENCE: 2

Leu Pro Pro Gly Thr Pro Thr Lys Ser Glu Ala Gln Asn Gln Leu Asn
1               5                   10                  15

Ser Leu Thr Val Lys Ser Glu Gly Ser Met Thr Gly Tyr Ser Arg Asp
            20                  25                  30

Leu Phe Pro His Trp Ser Gly Gln Gly Asn Gly Cys Asp Thr Arg Gln
        35                  40                  45

Ile Val Leu Gln Arg Asp Ala Asp Tyr Tyr Thr Gly Thr Cys Pro Thr
    50                  55                  60

Thr Ser Gly Lys Trp Tyr Ser Tyr Phe Asp Gly Val Ile Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Gln Arg Arg Ala Phe Ala
            100                 105                 110

Asn Asp Leu Asn Gly Pro Gln Leu Ile Ala Val Thr Ala Ser Val Asn
            115                 120                 125

Arg Ser Lys Gly Asp Gln Asp Pro Ser Thr Trp Gln Pro Pro Arg Ala
        130                 135                 140

Gly Ala Arg Cys Ala Tyr Ala Lys Trp Trp Ile Asn Thr Lys His Arg
145                 150                 155                 160

Trp Asn Leu His Leu Gln Ser Ser Glu Lys Ser Ser Leu Gln Thr Met
                165                 170                 175

Leu Asn Gly Cys Ala Tyr
            180

<210> SEQ ID NO 3
<211> LENGTH: 182
<212> TYPE: PRT
<213> ORGANISM: Bacillus sp-62520

<400> SEQUENCE: 3

Leu Pro Pro Gly Thr Pro Ser Lys Ser Glu Ala Gln Ser Gln Leu Asn
1               5                   10                  15

Ala Leu Thr Val Lys Pro Glu Asp Pro Met Thr Gly Tyr Ser Arg Asp
            20                  25                  30

His Phe Pro His Trp Ile Ser Gln Gly Asn Gly Cys Asn Thr Arg Gln
        35                  40                  45
```

Ile Val Leu Gln Arg Asp Ala Asp Tyr Tyr Ser Gly Ala Cys Pro Val
    50                  55                  60

Thr Thr Gly Lys Trp Tyr Ser Tyr Phe Asp Gly Val Ile Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Arg Ser Phe Ala
                100                 105                 110

Asn Asp Leu Asn Gly Pro Gln Leu Ile Ala Val Thr Ala Ser Val Asn
                115                 120                 125

Arg Ser Lys Gly Asp Gln Asp Pro Ser Thr Trp Gln Pro Pro Arg Ala
130                 135                 140

Gly Ala Arg Cys Ala Tyr Ala Lys Trp Trp Ile Asn Thr Lys His Arg
145                 150                 155                 160

Trp Gly Leu His Leu Gln Ser Ser Glu Lys Ser Ser Leu Gln Ser Met
                165                 170                 175

Leu Asn Gly Cys Ala Tyr
            180

<210> SEQ ID NO 4
<211> LENGTH: 182
<212> TYPE: PRT
<213> ORGANISM: Bacillus sp-62520

<400> SEQUENCE: 4

Leu Pro Pro Gly Thr Pro Ser Lys Ser Glu Ala Gln Ser Gln Leu Asn
1               5                   10                  15

Ala Leu Thr Val Lys Pro Glu Asp Pro Met Thr Gly Tyr Ser Arg Asp
                20                  25                  30

His Phe Pro His Trp Ile Ser Gln Gly Asn Gly Cys Asn Thr Arg Gln
            35                  40                  45

Ile Val Leu Gln Arg Asp Ala Asp Tyr Tyr Ser Gly Ala Cys Pro Val
    50                  55                  60

Thr Thr Gly Lys Trp Tyr Ser Tyr Phe Asp Gly Val Ile Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Gln Arg Arg Ser Phe Ala
                100                 105                 110

Asn Asp Leu Asn Gly Pro Gln Leu Ile Ala Val Thr Ala Ser Val Asn
                115                 120                 125

Arg Ser Lys Gly Asp Gln Asp Pro Ser Thr Trp Gln Pro Pro Arg Ala
130                 135                 140

Gly Ala Arg Cys Ala Tyr Ala Lys Trp Trp Ile Asn Thr Lys His Arg
145                 150                 155                 160

Trp Gly Leu His Leu Gln Ser Ser Glu Lys Ser Ser Leu Gln Ser Met
                165                 170                 175

Leu Asn Gly Cys Ala Tyr
            180

<210> SEQ ID NO 5
<211> LENGTH: 182
<212> TYPE: PRT
<213> ORGANISM: Bacillus horikoshii

<400> SEQUENCE: 5

```
Leu Pro Pro Gly Thr Pro Ser Lys Ser Glu Ala Gln Ser Gln Leu Asn
1               5                   10                  15

Ser Leu Thr Val Lys Ser Glu Asp Pro Met Thr Gly Tyr Ser Arg Asp
            20                  25                  30

His Phe Pro His Trp Ser Gly Gln Gly Asn Gly Cys Asp Thr Arg Gln
            35                  40                  45

Ile Val Leu Gln Arg Asp Ala Asp Tyr Tyr Ser Gly Asn Cys Pro Val
        50                  55                  60

Thr Ser Gly Lys Trp Tyr Ser Tyr Phe Asp Gly Val Ile Val Tyr Ser
65                  70                  75                  80

Pro Ser Glu Ile Asp Ile Asp His Val Val Pro Leu Ala Glu Ala Trp
                85                  90                  95

Arg Ser Gly Ala Ser Ser Trp Thr Thr Glu Gln Arg Arg Ser Phe Ala
            100                 105                 110

Asn Asp Leu Asn Gly Pro Gln Leu Ile Ala Val Thr Ala Ser Val Asn
            115                 120                 125

Arg Ser Lys Gly Asp Gln Asp Pro Ser Thr Trp Gln Pro Pro Arg Ala
        130                 135                 140

Gly Ala Arg Cys Ala Tyr Ala Lys Trp Trp Ile Asn Thr Lys His Arg
145                 150                 155                 160

Trp Asn Leu His Leu Gln Ser Ser Glu Lys Ser Ala Leu Gln Thr Met
            165                 170                 175

Leu Asn Gly Cys Val Tyr
            180

<210> SEQ ID NO 6
<211> LENGTH: 182
<212> TYPE: PRT
<213> ORGANISM: Bacillus horikoshii

<400> SEQUENCE: 6

Leu Pro Pro Gly Thr Pro Ser Lys Ser Glu Ala Gln Ser Gln Leu Asn
1               5                   10                  15

Ser Leu Thr Val Lys Thr Glu Asp Pro Met Thr Gly Tyr Ser Arg Asp
            20                  25                  30

Leu Phe Pro His Trp Ser Gly Gln Gly Ser Gly Cys Asp Thr Arg Gln
            35                  40                  45

Ile Val Leu Gln Arg Asp Ala Asp Tyr Phe Thr Gly Thr Cys Pro Thr
        50                  55                  60

Thr Ser Gly Lys Trp Tyr Ser Tyr Phe Asp Gly Val Ile Val Tyr Ser
65                  70                  75                  80

Pro Ser Glu Ile Asp Val Asp His Ile Val Pro Leu Ala Glu Ala Trp
                85                  90                  95

Arg Ser Gly Ala Ser Ser Trp Thr Thr Glu Gln Arg Arg Ala Phe Ala
            100                 105                 110

Asn Asp Leu Thr Gly Pro Gln Leu Ile Ala Val Thr Ala Ser Val Asn
            115                 120                 125

Arg Ser Lys Gly Asp Gln Asp Pro Ser Thr Trp Gln Pro Pro Arg Ala
        130                 135                 140

Gly Ala Arg Cys Ala Tyr Ala Lys Trp Trp Ile Asn Thr Lys His Arg
145                 150                 155                 160

Trp Asn Leu His Leu Gln Ser Ser Glu Lys Ser Ser Leu Gln Thr Met
            165                 170                 175

Leu Asn Gly Cys Ala Tyr
            180
```

<210> SEQ ID NO 7
<211> LENGTH: 182
<212> TYPE: PRT
<213> ORGANISM: Bacillus sp-16840

<400> SEQUENCE: 7

```
Leu Pro Pro Gly Thr Pro Ser Lys Ser Glu Ala Gln Ser Gln Leu Asn
1               5                   10                  15

Ala Leu Thr Val Lys Ala Glu Asp Pro Met Thr Gly Tyr Ser Arg Asn
            20                  25                  30

Leu Phe Pro His Trp Asn Ser Gln Gly Asn Gly Cys Asn Thr Arg Gln
        35                  40                  45

Leu Val Leu Gln Arg Asp Ala Asp Tyr Tyr Ser Gly Asn Cys Pro Val
    50                  55                  60

Thr Ser Gly Arg Trp Tyr Ser Tyr Phe Asp Gly Val Val Val Thr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Lys Glu Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ala
    130                 135                 140

Ala Ala Arg Cys Gly Tyr Ala Lys Trp Trp Ile Asn Thr Lys Tyr Arg
145                 150                 155                 160

Trp Asp Leu Ser Leu Gln Ser Ser Glu Lys Ser Ser Leu Gln Thr Met
                165                 170                 175

Leu Asn Thr Cys Ser Tyr
            180
```

<210> SEQ ID NO 8
<211> LENGTH: 182
<212> TYPE: PRT
<213> ORGANISM: Bacillus sp-16840

<400> SEQUENCE: 8

```
Leu Pro Pro Gly Thr Pro Ser Lys Ser Gln Ala Gln Ser Gln Leu Asn
1               5                   10                  15

Ala Leu Thr Val Lys Ala Glu Asp Pro Met Thr Gly Tyr Ser Arg Asn
            20                  25                  30

Leu Phe Pro His Trp Ser Ser Gln Gly Asn Gly Cys Asn Thr Arg Gln
        35                  40                  45

Leu Val Leu Gln Arg Asp Ala Asp Tyr Tyr Ser Gly Asn Cys Pro Val
    50                  55                  60

Thr Ser Gly Arg Trp Tyr Ser Tyr Phe Asp Gly Val Val Val Thr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Arg Glu Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Val
    130                 135                 140
```

```
Ala Ala Arg Cys Gly Tyr Ala Lys Trp Trp Ile Asn Thr Lys Tyr Arg
145                 150                 155                 160

Trp Asp Leu Ser Leu Gln Ser Ser Glu Lys Ser Ser Leu Gln Thr Met
            165                 170                 175

Leu Asn Thr Cys Ser Tyr
            180

<210> SEQ ID NO 9
<211> LENGTH: 182
<212> TYPE: PRT
<213> ORGANISM: Bacillus sp-62668

<400> SEQUENCE: 9

Leu Pro Pro Gly Thr Pro Ser Lys Ser Glu Ala Gln Ser Gln Leu Thr
1               5                   10                  15

Ser Leu Thr Val Lys Pro Glu Asp Pro Met Thr Gly Tyr Ser Arg Asp
            20                  25                  30

His Phe Pro His Trp Ile Ser Gln Gly Asn Gly Cys Asn Thr Arg Gln
        35                  40                  45

Ile Val Leu Gln Arg Asp Ala Asp Tyr Tyr Ser Gly Asn Cys Pro Val
50                  55                  60

Thr Thr Gly Lys Trp Tyr Ser Tyr Phe Asp Gly Val Ile Val Tyr Ser
65                  70                  75                  80

Pro Ser Glu Ile Asp Ile Asp His Ile Val Pro Leu Ala Glu Ala Trp
            85                  90                  95

Arg Ser Gly Ala Ser Ser Trp Thr Ala Glu Gln Arg Asn Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Thr
130                 135                 140

Gly Ala Arg Cys Ala Tyr Ala Lys Trp Trp Ile Asn Thr Lys Tyr Arg
145                 150                 155                 160

Trp Gly Leu His Leu Gln Ser Ser Glu Lys Ser Ser Leu Gln Ser Met
            165                 170                 175

Leu Asn Gly Cys Ala Tyr
            180

<210> SEQ ID NO 10
<211> LENGTH: 183
<212> TYPE: PRT
<213> ORGANISM: Bacillus sp-13395

<400> SEQUENCE: 10

Ala Phe Pro Pro Gly Thr Pro Ser Lys Ser Thr Ala Gln Ser Gln Leu
1               5                   10                  15

Asn Ser Leu Thr Val Lys Ser Glu Gly Ser Met Thr Gly Tyr Ser Arg
            20                  25                  30

Asp Lys Phe Pro His Trp Ile Ser Gln Gly Asp Gly Cys Asp Thr Arg
        35                  40                  45

Gln Leu Val Leu Lys Arg Asp Gly Asp Tyr Tyr Ser Gly Asn Cys Pro
50                  55                  60

Val Thr Ser Gly Lys Trp Tyr Ser Tyr Asp Gly Ile Ala Val Tyr
65                  70                  75                  80

Ser Pro Ser Glu Ile Asp Ile Asp His Ile Val Pro Leu Ala Glu Ala
            85                  90                  95
```

```
Trp Arg Ser Gly Ala Ser Gly Trp Thr Thr Glu Lys Arg Gln Asn Phe
            100                 105                 110

Ala Asn Asp Leu Asn Gly Pro Gln Leu Ile Ala Val Thr Ala Ser Val
        115                 120                 125

Asn Arg Ser Lys Gly Asp Gln Asp Pro Ser Thr Trp Gln Pro Pro Arg
    130                 135                 140

Ser Gly Ser His Cys Ala Tyr Ala Lys Met Trp Val Asn Thr Lys Tyr
145                 150                 155                 160

Arg Trp Gly Leu His Leu Gln Ser Ala Glu Lys Ser Ala Leu Gln Ser
                165                 170                 175

Met Leu Asn Ala Cys Ser Tyr
            180

<210> SEQ ID NO 11
<211> LENGTH: 185
<212> TYPE: PRT
<213> ORGANISM: Bacillus horneckiae

<400> SEQUENCE: 11

Ala Ser Ala Phe Pro Pro Gly Thr Pro Ser Lys Ser Thr Ala Gln Ser
1               5                   10                  15

Gln Leu Asn Ser Leu Thr Val Lys Ser Glu Gly Ser Met Thr Gly Tyr
            20                  25                  30

Ser Arg Asp Lys Phe Pro His Trp Ile Ser Gln Gly Asp Gly Cys Asp
        35                  40                  45

Thr Arg Gln Leu Val Leu Lys Arg Asp Gly Asp Tyr Tyr Ser Gly Asn
    50                  55                  60

Cys Pro Val Thr Ser Gly Lys Trp Tyr Ser Tyr Tyr Asp Gly Ile Thr
65                  70                  75                  80

Val Tyr Ser Pro Ser Glu Ile Asp Ile Asp His Ile Val Pro Leu Ala
                85                  90                  95

Glu Ala Trp Arg Ser Gly Ala Ser Gly Trp Thr Thr Glu Lys Arg Gln
            100                 105                 110

Ser Phe Ala Asn Asp Leu Asn Gly Pro Gln Leu Ile Ala Val Thr Ala
        115                 120                 125

Ser Val Asn Arg Ser Lys Gly Asp Gln Asp Pro Ser Thr Trp Gln Pro
    130                 135                 140

Pro Arg Ser Gly Ser His Cys Ala Tyr Ala Lys Met Trp Val Asn Thr
145                 150                 155                 160

Lys Tyr Arg Trp Gly Leu His Val Gln Ser Ala Glu Lys Ser Ala Leu
                165                 170                 175

Gln Ser Met Leu Asn Ala Cys Ser Tyr
            180                 185

<210> SEQ ID NO 12
<211> LENGTH: 182
<212> TYPE: PRT
<213> ORGANISM: Bacillus sp-11238

<400> SEQUENCE: 12

Phe Pro Pro Glu Ile Pro Ser Lys Ser Thr Ala Gln Ser Gln Leu Asn
1               5                   10                  15

Ser Leu Thr Val Lys Ser Glu Asp Ala Met Thr Gly Tyr Ser Arg Asp
            20                  25                  30

Lys Phe Pro His Trp Ile Ser Gln Gly Asp Gly Cys Asp Thr Arg Gln
        35                  40                  45
```

```
Met Val Leu Lys Arg Asp Ala Asp Tyr Tyr Ser Gly Ser Cys Pro Val
    50                  55                  60

Thr Ser Gly Lys Trp Tyr Ser Tyr Tyr Asp Gly Ile Thr Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Arg Asn Phe Ala
                100                 105                 110

Asn Asp Leu Asn Gly Pro Gln Leu Ile Ala Val Thr Ala Ser Val Asn
            115                 120                 125

Arg Ser Lys Gly Asp Gln Asp Pro Ser Thr Trp Gln Pro Pro Arg Ser
        130                 135                 140

Gly Ala Arg Cys Ala Tyr Ala Lys Met Trp Val Asn Thr Lys Tyr Arg
145                 150                 155                 160

Trp Gly Leu His Leu Gln Ser Ala Glu Lys Ser Gly Leu Glu Ser Met
                165                 170                 175

Leu Asn Thr Cys Ser Tyr
            180
```

<210> SEQ ID NO 13
<211> LENGTH: 182
<212> TYPE: PRT
<213> ORGANISM: Bacillus cibi

<400> SEQUENCE: 13

```
Thr Pro Pro Gly Thr Pro Ser Lys Ser Ala Gln Ser Gln Leu Asn
1               5                   10                  15

Ala Leu Thr Val Lys Thr Glu Gly Ser Met Ser Gly Tyr Ser Arg Asp
                20                  25                  30

Leu Phe Pro His Trp Ile Ser Gln Gly Ser Gly Cys Asp Thr Arg Gln
                35                  40                  45

Val Val Leu Lys Arg Asp Ala Asp Ser Tyr Ser Gly Asn Cys Pro Val
            50                  55                  60

Thr Ser Gly Ser Trp Tyr Ser Tyr Tyr Asp Gly Val Thr Phe Thr Asn
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ser Lys Arg Gln Asp Phe Ala
                100                 105                 110

Asn Asp Leu Ser Gly Pro Gln Leu Ile Ala Val Ser Ala Ser Thr Asn
            115                 120                 125

Arg Ser Lys Gly Asp Gln Asp Pro Ser Thr Trp Gln Pro Pro Arg Ser
        130                 135                 140

Gly Ala Ala Cys Gly Tyr Ser Lys Trp Trp Ile Ser Thr Lys Tyr Lys
145                 150                 155                 160

Trp Gly Leu Ser Leu Gln Ser Ser Glu Lys Thr Ala Leu Gln Gly Met
                165                 170                 175

Leu Asn Ser Cys Ser Tyr
            180
```

<210> SEQ ID NO 14
<211> LENGTH: 182
<212> TYPE: PRT
<213> ORGANISM: Bacillus sp-18318

<400> SEQUENCE: 14

```
Phe Pro Pro Gly Thr Pro Ser Lys Ser Thr Ala Gln Ser Gln Leu Asn
1               5                   10                  15

Ser Leu Thr Val Lys Ser Glu Gly Ser Met Thr Gly Tyr Ser Arg Asp
            20                  25                  30

Lys Phe Pro His Trp Ile Gly Gln Gly Ser Gly Cys Asp Thr Arg Gln
            35                  40                  45

Leu Val Leu Gln Arg Asp Ala Asp Tyr Tyr Ser Gly Ser Cys Pro Val
        50                  55                  60

Thr Ser Gly Lys Trp Tyr Ser Tyr Tyr Asp Gly Val Thr Phe Tyr Asp
65                  70                  75                  80

Pro Ser Asp Leu Asp Ile Asp His Val Val Pro Leu Ala Glu Ala Trp
                85                  90                  95

Arg Ser Gly Ala Ser Ser Trp Ser Thr Gln Lys Arg Lys Asp Phe Ala
                100                 105                 110

Asn Asp Leu Ser Gly Pro Gln Leu Ile Ala Val Ser Ala Ser Ser Asn
            115                 120                 125

Arg Ser Lys Gly Asp Gln Asp Pro Ser Thr Trp Gln Pro Thr Arg Ser
        130                 135                 140

Gly Ala Ala Cys Gly Tyr Ser Lys Trp Trp Ile Ser Thr Lys His Lys
145                 150                 155                 160

Trp Gly Leu Ser Leu Gln Ser Ser Glu Lys Asn Ala Leu Gln Gly Met
                165                 170                 175

Leu Asn Ser Cys Val Tyr
            180

<210> SEQ ID NO 15
<211> LENGTH: 182
<212> TYPE: PRT
<213> ORGANISM: Bacillus idriensis

<400> S

180

<210> SEQ ID NO 16
<211> LENGTH: 182
<212> TYPE: PRT
<213> ORGANISM: Bacillus algicola

<400> SEQUENCE: 16

```
Phe Pro Pro Gly Thr Pro Ser Lys Ser Glu Ala Gln Ser Gln Leu Asn
1               5                   10                  15

Ser Leu Thr Val Gln Ser Glu Gly Ser Met Ser Gly Tyr Ser Arg Asp
            20                  25                  30

Lys Phe Pro His Trp Ile Gly Gln Gly Asn Gly Cys Asp Thr Arg Gln
        35                  40                  45

Leu Val Leu Gln Arg Asp Ala Asp Tyr Tyr Ser Gly Asp Cys Pro Val
    50                  55                  60

Thr Ser Gly Lys Trp Tyr Ser Tyr Phe Asp Gly Val Thr Val Tyr Asp
65                  70                  75                  80

Pro Ser Asp Leu Asp Ile Asp His Met Val Pro Met Ala Glu Ala Trp
                85                  90                  95

Arg Ser Gly Ala Ser Ser Trp Ser Thr Gln Lys Arg Glu Asp Phe Ala
            100                 105                 110

Asn Asp Leu Ser Gly Pro His Leu Ile Ala Val Thr Ala Ser Ser Asn
        115                 120                 125

Arg Ser Lys Gly Asp Gln Asp Pro Ser Thr Trp Lys Pro Thr Arg Tyr
    130                 135                 140

Gly Ala His Cys Gly Tyr Ala Lys Trp Trp Ile Asn Thr Lys Tyr Val
145                 150                 155                 160

Tyr Asp Leu Thr Leu Gln Ser Ser Glu Lys Thr Glu Leu Gln Ser Met
                165                 170                 175

Leu Asn Thr Cys Ser Tyr
            180
```

<210> SEQ ID NO 17
<211> LENGTH: 182
<212> TYPE: PRT
<213> ORGANISM: Enviromental sample J

<400> SEQUENCE: 17

```
Leu Pro Pro Asn Ile Pro Ser Lys Ala Asp Ala Leu Thr Lys Leu Asn
1               5                   10                  15

Ala Leu Thr Val Gln Thr Glu Gly Pro Met Thr Gly Tyr Ser Arg Asp
            20                  25                  30

Leu Phe Pro His Trp Ser Ser Gln Gly Asn Gly Cys Asn Thr Arg His
        35                  40                  45

Val Val Leu Lys Arg Asp Ala Asp Ser Val Asp Thr Cys Pro Val
    50                  55                  60

Thr Thr Gly Arg Trp Tyr Ser Tyr Tyr Asp Gly Leu Val Phe Thr Ser
65                  70                  75                  80

Ala Ser Asp Ile Asp Ile Asp His Val Val Pro Leu Ala Glu Ala Trp
                85                  90                  95

Arg Ser Gly Ala Ser Ser Trp Thr Ser Thr Lys Arg Gln Ser Phe Ala
            100                 105                 110

Asn Asp Leu Asn Gly Pro Gln Leu Ile Ala Val Ser Ala Thr Ser Asn
        115                 120                 125

Arg Ser Lys Gly Asp Gln Asp Pro Ser Thr Trp Gln Pro Pro Arg Ala
```

Gly Ala Arg Cys Ala Tyr Ala Lys Met Trp Val Glu Thr Lys Ser Arg
145                 150                 155                 160

Trp Gly Leu Thr Leu Gln Ser Ser Glu Lys Ala Ala Leu Gln Thr Ala
                165                 170                 175

Ile Asn Ala Cys Ser Tyr
            180

<210> SEQ ID NO 18
<211> LENGTH: 182
<212> TYPE: PRT
<213> ORGANISM: Bacillus vietnamensis

<400> SEQUENCE: 18

Phe Pro Pro Gly Thr Pro Ser Lys Ser Thr Ala Gln Ser Gln Leu Asn
1               5                   10                  15

Ala Leu Thr Val Lys Ser Glu Ser Ser Met Thr Gly Tyr Ser Arg Asp
                20                  25                  30

Lys Phe Pro His Trp Ile Gly Gln Arg Asn Gly Cys Asp Thr Arg Gln
            35                  40                  45

Leu Val Leu Gln Arg Asp Ala Asp Ser Tyr Ser Gly Ser Cys Pro Val
        50                  55                  60

Thr Ser Gly Ser Trp Tyr Ser Tyr Tyr Asp Gly Val Thr Phe Thr Asp
65                  70                  75                  80

Pro Ser Asp Leu Asp Ile Asp His Val Val Pro Leu Ala Glu Ala Trp
                85                  90                  95

Arg Ser Gly Ala Ser Ser Trp Thr Thr Ala Lys Arg Glu Asp Phe Ala
            100                 105                 110

Asn Asp Leu Ser Gly Pro Gln Leu Ile Ala Val Ser Ala Ser Ser Asn
        115                 120                 125

Arg Ser Lys Gly Asp Gln Asp Pro Ser Thr Trp Gln Pro Pro Arg Ser
130                 135                 140

Gly Ala Ala Cys Gly Tyr Ser Lys Trp Trp Ile Ser Thr Lys Tyr Lys
145                 150                 155                 160

Trp Gly Leu Ser Leu Gln Ser Ser Glu Lys Thr Ala Leu Gln Gly Met
                165                 170                 175

Leu Asn Ser Cys Ile Tyr
            180

<210> SEQ ID NO 19
<211> LENGTH: 182
<212> TYPE: PRT
<213> ORGANISM: Bacillus hwajinpoensis

<400> SEQUENCE: 19

Ile Pro Pro Gly Thr Pro Ser Lys Ser Ala Ala Gln Ser Gln Leu Asp
1               5                   10                  15

Ser Leu Ala Val Gln Ser Glu Gly Ser Met Ser Gly Tyr Ser Arg Asp
                20                  25                  30

Lys Phe Pro His Trp Ile Gly Gln Gly Asn Gly Cys Asp Thr Arg Gln
            35                  40                  45

Leu Val Leu Gln Arg Asp Ala Asp Tyr Tyr Ser Gly Asp Cys Pro Val
        50                  55                  60

Thr Ser Gly Lys Trp Tyr Ser Tyr Phe Asp Gly Val Gln Val Tyr Asp
65                  70                  75                  80

Pro Ser Tyr Leu Asp Ile Asp His Met Val Pro Leu Ala Glu Ala Trp

```
                85                  90                  95

Arg Ser Gly Ala Ser Ser Trp Ser Thr Gln Lys Arg Glu Asp Phe Ala
            100                 105                 110

Asn Asp Leu Asp Gly Pro His Leu Ile Ala Val Thr Ala Ser Ser Asn
        115                 120                 125

Arg Ser Lys Gly Asp Gln Asp Pro Ser Thr Trp Lys Pro Thr Arg Tyr
    130                 135                 140

Ser Ala His Cys Gly Tyr Ala Lys Trp Trp Ile Asn Thr Lys Tyr Val
145                 150                 155                 160

Tyr Asp Leu Asn Leu Gln Ser Ser Glu Lys Ser Ala Leu Gln Ser Met
                165                 170                 175

Leu Asn Thr Cys Ser Tyr
            180

<210> SEQ ID NO 20
<211> LENGTH: 182
<212> TYPE: PRT
<213> ORGANISM: Paenibacillus mucilaginosus

<400> SEQUENCE: 20

Leu Pro Pro Gly Thr Pro Ser Lys Ser Thr Ala Gln Ser Gln Leu Asn
1               5                   10                  15

Ser Leu Thr Val Lys Ser Glu Ser Thr Met Thr Gly Tyr Ser Arg Asp
            20                  25                  30

Lys Phe Pro His Trp Thr Ser Gln Gly Gly Gly Cys Asp Thr Arg Gln
        35                  40                  45

Val Val Leu Lys Arg Asp Ala Asp Tyr Tyr Ser Gly Ser Cys Pro Val
    50                  55                  60

Thr Ser Gly Lys Trp Tyr Ser Tyr Tyr Asp Gly Ile Thr Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Gln Asn Phe Ala
            100                 105                 110

Asn Asp Leu Gly Gly Pro Gln Leu Ile Ala Val Thr Ala Ser Ser Asn
        115                 120                 125

Arg Ala Lys Gly Asp Gln Asp Pro Ser Thr Trp Lys Pro Thr Arg Ser
    130                 135                 140

Gly Ala His Cys Ala Tyr Ala Lys Trp Trp Ile Asn Thr Lys Tyr Arg
145                 150                 155                 160

Trp Gly Leu His Leu Gln Ser Ser Glu Lys Thr Ala Leu Gln Ser Met
                165                 170                 175

Leu Asn Thr Cys Ser Tyr
            180

<210> SEQ ID NO 21
<211> LENGTH: 182
<212> TYPE: PRT
<213> ORGANISM: Bacillus indicus

<400> SEQUENCE: 21

Thr Pro Pro Gly Thr Pro Ser Lys Ser Thr Ala Gln Thr Gln Leu Asn
1               5                   10                  15

Ala Leu Thr Val Lys Thr Glu Gly Ser Met Thr Gly Tyr Ser Arg Asp
            20                  25                  30

Leu Phe Pro His Trp Ile Ser Gln Gly Ser Gly Cys Asp Thr Arg Gln
```

```
                35                  40                  45
Val Val Leu Lys Arg Asp Ala Asp Tyr Tyr Ser Gly Ser Cys Pro Val
         50                  55                  60

Thr Ser Gly Lys Trp Tyr Ser Tyr Tyr Asp Gly Val Thr Phe Tyr Asp
 65                  70                  75                  80

Pro Ser Asp Leu Asp Ile Asp His Ile Val Pro Leu Ala Glu Ala Trp
                 85                  90                  95

Arg Ser Gly Ala Ser Ser Trp Thr Thr Ser Lys Arg Gln Asp Phe Ala
            100                 105                 110

Asn Asp Leu Ser Gly Pro Gln Leu Ile Ala Val Ser Ala Ser Thr Asn
            115                 120                 125

Arg Ser Lys Gly Asp Gln Asp Pro Ser Thr Trp Gln Pro Pro Arg Ala
        130                 135                 140

Gly Ala Ala Cys Gly Tyr Ser Lys Trp Trp Ile Ser Thr Lys Tyr Lys
145                 150                 155                 160

Trp Gly Leu Ser Leu Gln Ser Ser Glu Lys Thr Ala Leu Gln Gly Met
            165                 170                 175

Leu Asn Ser Cys Ser Tyr
            180

<210> SEQ ID NO 22
<211> LENGTH: 182
<212> TYPE: PRT
<213> ORGANISM: Bacillus marisflavi

<400> SEQUENCE: 22

Thr Pro Pro Val Thr Pro Ser Lys Ala Thr Ser Gln Ser Gln Leu Asn
 1               5                  10                  15

Gly Leu Thr Val Lys Thr Glu Gly Ala Met Thr Gly Tyr Ser Arg Asp
            20                  25                  30

Lys Phe Pro His Trp Ser Ser Gln Gly Gly Gly Cys Asp Thr Arg Gln
            35                  40                  45

Val Val Leu Lys Arg Asp Ala Asp Ser Tyr Ser Gly Asn Cys Pro Val
         50                  55                  60

Thr Ser Gly Ser Trp Tyr Ser Tyr Tyr Asp Gly Val Lys Phe Thr Asn
 65                  70                  75                  80

Pro Ser Asp Leu Asp Ile Asp His Ile Val Pro Leu Ala Glu Ala Trp
                 85                  90                  95

Arg Ser Gly Ala Ser Ser Trp Thr Thr Ala Gln Arg Glu Ala Phe Ala
            100                 105                 110

Asn Asp Leu Ser Gly Ser Gln Leu Ile Ala Val Ser Ala Ser Ser Asn
            115                 120                 125

Arg Ser Lys Gly Asp Gln Asp Pro Ser Thr Trp Gln Pro Pro Arg Ala
        130                 135                 140

Gly Ala Lys Cys Gly Tyr Ala Lys Trp Trp Ile Ser Thr Lys Ser Lys
145                 150                 155                 160

Trp Asn Leu Ser Leu Gln Ser Ser Glu Lys Thr Ala Leu Gln Gly Met
            165                 170                 175

Leu Asn Ser Cys Val Tyr
            180

<210> SEQ ID NO 23
<211> LENGTH: 184
<212> TYPE: PRT
<213> ORGANISM: Bacillus luciferensis
```

-continued

<400> SEQUENCE: 23

```
Ala Ser Leu Pro Pro Gly Ile Pro Ser Leu Ser Thr Ala Gln Ser Gln
1               5                   10                  15

Leu Asn Ser Leu Thr Val Lys Ser Glu Gly Ser Leu Thr Gly Tyr Ser
            20                  25                  30

Arg Asp Val Phe Pro His Trp Ile Ser Gln Gly Ser Gly Cys Asp Thr
        35                  40                  45

Arg Gln Val Val Leu Lys Arg Asp Ala Asp Tyr Tyr Ser Gly Asn Cys
    50                  55                  60

Pro Val Thr Ser Gly Lys Trp Tyr Ser Tyr Tyr Asp Gly Val Thr Val
65                  70                  75                  80

Tyr Ser Pro Ser Glu Ile Asp Ile Asp His Val Val Pro Leu Ala Glu
                85                  90                  95

Ala Trp Arg Ser Gly Ala Ser Ser Trp Thr Thr Glu Lys Arg Gln Asn
            100                 105                 110

Phe Ala Asn Asp Leu Asn Gly Pro Gln Leu Ile Ala Val Thr Ala Ser
        115                 120                 125

Ser Asn Arg Ser Lys Gly Asp Gln Asp Pro Ser Thr Trp Gln Pro Thr
    130                 135                 140

Arg Thr Gly Ala Arg Cys Ala Tyr Ala Lys Met Trp Ile Asn Thr Lys
145                 150                 155                 160

Tyr Arg Trp Gly Leu His Leu Gln Ser Ser Glu Lys Ser Ala Leu Gln
                165                 170                 175

Ser Met Leu Asn Thr Cys Ser Tyr
            180
```

<210> SEQ ID NO 24
<211> LENGTH: 182
<212> TYPE: PRT
<213> ORGANISM: Bacillus marisflavi

<400> SEQUENCE: 24

```
Thr Pro Pro Val Thr Pro Ser Lys Glu Thr Ser Gln Ser Gln Leu Asn
1               5                   10                  15

Gly Leu Thr Val Lys Thr Glu Gly Ala Met Thr Gly Tyr Ser Arg Asp
            20                  25                  30

Lys Phe Pro His Trp Ser Ser Gln Gly Gly Cys Asp Thr Arg Gln
        35                  40                  45

Val Val Leu Lys Arg Asp Ala Asp Ser Tyr Ser Gly Asn Cys Pro Val
    50                  55                  60

Thr Ser Gly Ser Trp Tyr Ser Tyr Tyr Asp Gly Val Lys Phe Thr His
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ala Gln Arg Glu Ala Phe Ala
            100                 105                 110

Asn Asp Leu Ser Gly Ser Gln Leu Ile Ala Val Ser Ala Ser Ser Asn
        115                 120                 125

Arg Ser Lys Gly Asp Gln Asp Pro Ser Thr Trp Gln Pro Pro Arg Ala
    130                 135                 140

Gly Ala Lys Cys Gly Tyr Ala Lys Trp Trp Ile Ser Thr Lys Ser Lys
145                 150                 155                 160

Trp Asn Leu Ser Leu Gln Ser Ser Glu Lys Thr Ala Leu Gln Gly Met
                165                 170                 175
```

Leu Asn Ser Cys Val Tyr
         180

<210> SEQ ID NO 25
<211> LENGTH: 182
<212> TYPE: PRT
<213> ORGANISM: Bacillus sp. SA2-6

<400> SEQUENCE: 25

Leu Pro Ser Gly Ile Pro Ser Lys Ser Thr Ala Gln Ser Gln Leu Asn
1               5                   10                  15

Ser Leu Thr Val Lys Ser Glu Gly Ser Met Thr Gly Tyr Ser Arg Asp
            20                  25                  30

Lys Phe Pro His Trp Ile Ser Gln Gly Gly Cys Asp Thr Arg Gln
        35                  40                  45

Val Val Leu Lys Arg Asp Ala Asp Tyr Tyr Ser Gly Asn Cys Pro Val
    50                  55                  60

Thr Ser Gly Lys Trp Tyr Ser Tyr Tyr Asp Gly Ile Ser Val Tyr Ser
65                  70                  75                  80

Pro Ser Glu Ile Asp Ile Asp His Val Val Pro Leu Ala Glu Ala Trp
                85                  90                  95

Arg Ser Gly Ala Ser Ser Trp Thr Thr Thr Lys Arg Gln Asn Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Tyr
    130                 135                 140

Gly Ala Arg Cys Ala Tyr Ala Lys Met Trp Ile Asn Thr Lys Tyr Arg
145                 150                 155                 160

Trp Asp Leu Asn Leu Gln Ser Ser Glu Lys Ser Ser Leu Gln Ser Met
                165                 170                 175

Leu Asp Thr Cys Ser Tyr
         180

<210> SEQ ID NO 26
<211> LENGTH: 191
<212> TYPE: PRT
<213> ORGANISM: Pyrenochaetopsis sp.

<400> SEQUENCE: 26

Leu Pro Ser Pro Leu Ile Ala Arg Ser Pro Asn Ile Pro Ser
1               5                   10                  15

Ala Thr Thr Ala Lys Thr Gln Leu Ala Gly Leu Thr Val Ala Pro Gln
            20                  25                  30

Gly Pro Gln Thr Gly Tyr Ser Arg Asp Leu Phe Pro His Trp Ile Thr
        35                  40                  45

Gln Ser Gly Thr Cys Asn Thr Arg Glu Val Val Leu Lys Arg Asp Gly
    50                  55                  60

Thr Asn Val Val Thr Asn Ser Ala Cys Ala Ser Thr Ser Gly Ser Trp
65                  70                  75                  80

Leu Ser Pro Tyr Asp Gly Lys Thr Trp Asp Ser Ala Ser Asp Ile Gln
                85                  90                  95

Ile Asp His Leu Val Pro Leu Ser Asn Ala Trp Lys Ser Gly Ala Ala
            100                 105                 110

Ala Trp Thr Thr Ala Gln Arg Gln Ala Phe Ala Asn Asp Leu Thr His
        115                 120                 125

```
Pro Gln Leu Val Ala Val Thr Gly Ser Val Asn Glu Ser Lys Gly Asp
        130                 135                 140

Asp Gly Pro Glu Asp Trp Lys Pro Pro Leu Ala Ser Tyr Tyr Cys Thr
145                 150                 155                 160

Tyr Ala Ser Met Trp Thr Ala Val Lys Ser Asn Tyr Lys Leu Thr Ile
                165                 170                 175

Thr Ser Ala Glu Lys Ser Ala Leu Thr Ser Met Leu Ala Thr Cys
            180                 185                 190
```

<210> SEQ ID NO 27
<211> LENGTH: 190
<212> TYPE: PRT
<213> ORGANISM: Vibrissea flavovirens

<400> SEQUENCE: 27

```
Thr Pro Leu Pro Ile Ile Ala Arg Thr Pro Asn Ile Pro Thr Thr
1               5                   10                  15

Ala Thr Ala Lys Ser Gln Leu Ala Ala Leu Thr Val Ala Ala Gly
            20                  25                  30

Pro Gln Thr Gly Tyr Ser Arg Asp Leu Phe Pro Thr Trp Ile Thr Ile
        35                  40                  45

Ser Gly Thr Cys Asn Thr Arg Glu Thr Val Leu Lys Arg Asp Gly Thr
50                  55                  60

Asn Val Val Asp Ser Ala Cys Val Ala Thr Ser Gly Ser Trp Tyr
65                  70                  75                  80

Ser Pro Tyr Asp Gly Ala Thr Trp Thr Ala Ser Asp Val Asp Ile
                85                  90                  95

Asp His Met Val Pro Leu Ser Asn Ala Trp Lys Ser Gly Ala Ser Ala
            100                 105                 110

Trp Thr Thr Ala Gln Arg Gln Thr Phe Ala Asn Asp Leu Thr Asn Pro
            115                 120                 125

Gln Leu Leu Ala Val Thr Asp Asn Val Asn Gln Ala Lys Gly Asp Ser
        130                 135                 140

Gly Pro Glu Asp Trp Lys Pro Ser Leu Thr Ser Tyr Trp Cys Thr Tyr
145                 150                 155                 160

Ala Lys Met Trp Val Lys Val Lys Thr Val Tyr Asp Leu Thr Ile Thr
                165                 170                 175

Ser Ala Glu Lys Thr Ala Leu Thr Thr Met Leu Asn Thr Cys
            180                 185                 190
```

<210> SEQ ID NO 28
<211> LENGTH: 192
<212> TYPE: PRT
<213> ORGANISM: Setosphaeria rostrata

<400> SEQUENCE: 28

```
Ala Pro Thr Ser Pro Leu Val Ala Arg Ala Pro Asn Val Pro
1               5                   10                  15

Ser Lys Ala Glu Ala Thr Ser Gln Leu

```
Trp Phe Ser Pro Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
            100                 105                 110

Ala Ser Trp Thr Thr Ala Arg Arg Gln Ala Phe Ala Asn Asp Leu Thr
        115                 120                 125

Asn Pro Gln Leu Leu Ala Val Thr Asp Asn Val Asn Gln Ala Lys Gly
    130                 135                 140

Asp Lys Gly Pro Glu Asp Trp Lys Pro Pro Leu Thr Ser Tyr Tyr Cys
145                 150                 155                 160

Thr Tyr Ser Lys Met Trp Ile Lys Val Lys Ser Val Trp Gly Leu Thr
                165                 170                 175

Ile Thr Ser Ala Glu Lys Ser Ala Leu Thr Ser Met Leu Ala Thr Cys
            180                 185                 190

<210> SEQ ID NO 29
<211> LENGTH: 192
<212> TYPE: PRT
<213> ORGANISM: Endophragmiella valdina

<400> SEQUENCE: 29

Ala Pro Val Pro Gly His Leu Met Pro Arg Ala Pro Asn Val Pro
1               5                   10                  15

Thr Thr Ala Ala Lys Thr Ala Leu Ala Gly Leu Thr Val Gln Ala
            20                  25                  30

Gln Gly Ser Gln Thr Gly Tyr Ser Arg Asp Leu Phe Pro His Trp Ile
        35                  40                  45

Thr Gln Ser Gly Thr Cys Asn Thr Arg Glu Val Val Leu Lys Arg Asp
    50                  55                  60

Gly Thr Asn Val Val Thr Asp Ser Ala Cys Ala Ala Thr Ser Gly Thr
65                  70                  75                  80

Trp Val Ser Pro Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
            100                 105                 110

Ala Ser Trp Thr Thr Ala Gln Arg Gln Ala Phe Ala Asn Asp Leu Thr
        115                 120                 125

Asn Pro Gln Leu Leu Ala Val Thr Asp Asn Val Asn Gln Ser Lys Gly
    130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ser Leu Thr
                165                 170                 175

Ile Thr Ser Ala Glu Lys Thr Ala Leu Thr Ser Met Leu Asn Thr Cys
            180                 185                 190

<210> SEQ ID NO 30
<211> LENGTH: 190
<212> TYPE: PRT
<213> ORGANISM: Corynespora cassiicola

<400> SEQUENCE: 30

Leu Pro Ala Pro Leu Val Pro Arg Ala Pro Pro Gly Ile Pro Thr Thr
1               5                   10                  15

Ser Ala Ala Arg Ser Gln Leu Ala Gly Leu Thr Val Ala Ala Gln Gly
            20                  25                  30
```

Pro Gln Thr Gly Tyr Ser Arg Asp Leu Phe Pro His Trp Ile Thr Gln
             35                  40                  45

Ser Gly Ser Cys Asn Thr Arg Glu Val Val Leu Ala Arg Asp Gly Thr
 50                  55                  60

Gly Val Val Gln Asp Ser Ser Cys Ala Ala Thr Ser Gly Thr Trp Arg
 65                  70                  75                  80

Ser Pro Phe Asp Gly Ala Thr Trp Thr Ala Ala Ser Asp Val Asp Ile
                 85                  90                  95

Asp His Met Val Pro Leu Ser Asn Ala Trp Lys Ser Gly Ala Ala Ser
                100                 105                 110

Trp Thr Thr Ser Arg Arg Gln Ala Phe Ala Asn Asp Leu Thr Asn Pro
            115                 120                 125

Gln Leu Ile Ala Val Thr Asp Asn Val Asn Gln Ser Lys Gly Asp Lys
130                 135                 140

Gly Pro Glu Asp Trp Lys Pro Pro Leu Thr Ser Tyr Tyr Cys Thr Tyr
145                 150                 155                 160

Ala Lys Met Trp Val Arg Val Lys Ser Val Tyr Ser Leu Thr Ile Thr
                165                 170                 175

Ser Ala Glu Lys Ser Ala Leu Thr Ser Met Leu Asp Thr Cys
            180                 185                 190

<210> SEQ ID NO 31
<211> LENGTH: 192
<212> TYPE: PRT
<213> ORGANISM: Paraphoma sp. XZ1965

<400> SEQUENCE: 31

Ala Pro Ala Pro Val His Leu Val Ala Arg Ala Pro Pro Asn Val Pro
 1               5                  10                  15

Thr Ala Ala Gln Ala Gln Thr Gln Leu Ala Gly Leu Thr Val Ala Ala
             20                  25                  30

Gln Gly Pro Gln Thr Gly Tyr Ser Arg Asp Leu Phe Pro His Trp Ile
             35                  40                  45

Thr Gln Ser Gly Ala Cys Asn Thr Arg Glu Thr Val Leu Lys Arg Asp
 50                  55                  60

Gly Thr Gly Val Val Gln Asp Ser Ala Cys Ala Ala Thr Ser Gly Thr
 65                  70                  75                  80

Trp Lys Ser Pro Tyr Asp Gly Ala Thr Trp Thr Ala Ala Ser Asp Val
                 85                  90                  95

Asp Ile Asp His Met Val Pro Leu Ser Asn Ala Trp Lys Ser Gly Ala
                100                 105                 110

Ala Ser Trp Thr Thr Ala Arg Arg Gln Ala Phe Ala Asn Asp Leu Thr
            115                 120                 125

Asn Pro Gln Leu Leu Ala Val Thr Asp Asn Val Asn Gln Ala Lys Gly
130                 135                 140

Asp Lys Gly Pro Glu Asp Trp Lys Pro Pro Leu Thr Ser Tyr Tyr Cys
145                 150                 155                 160

Ile Tyr Ala Arg Met Trp Ile Lys Val Lys Ser Val Tyr Ser Leu Thr
                165                 170                 175

Ile Thr Ser Ala Glu Lys Ser Ala Leu Thr Ser Met Leu Gly Thr Cys
            180                 185                 190

<210> SEQ ID NO 32
<211> LENGTH: 186
<212> TYPE: PRT
<213> ORGANISM: Monilinia fructicola

<400> SEQUENCE: 32

Thr Pro Val Pro Ala Pro Thr Gly Ile Pro Ser Thr Ser Val Ala Asn
1               5                   10                  15

Thr Gln Leu Ala Ala Leu Thr Val Ala Ala Ala Gly Ser Gln Asp Gly
            20                  25                  30

Tyr Ser Arg Asp Leu Phe Pro His Trp Ile Thr Ile Ser Gly Ala Cys
        35                  40                  45

Asn Thr Arg Glu Thr Val Leu Lys Arg Asp Gly Thr Asn Val Val Val
50                  55                  60

Asn Ser Ala Cys Ala Ala Thr Ser Gly Thr Trp Val Ser Pro Tyr Asp
65                  70                  75                  80

Gly Ala Thr Trp Thr Ala Ala Ser Asp Val Asp Ile Asp His Leu Val
                85                  90                  95

Pro Leu Ser Asn Ala Trp Lys Ala Gly Ala Ser Ser Trp Thr Thr Ala
            100                 105                 110

Gln Arg Gln Ala Phe Ala Asn Asp Leu Val Asn Pro Gln Leu Leu Ala
        115                 120                 125

Val Thr Asp Ser Val Asn Gln Gly Lys Ser Asp Ser Gly Pro Glu Ala
130                 135                 140

Trp Lys Pro Ser Leu Lys Ser Tyr Trp Cys Thr Tyr Ala Lys Met Trp
145                 150                 155                 160

Ile Lys Val Lys Tyr Val Tyr Asp Leu Thr Ile Thr Ser Ala Glu Lys
                165                 170                 175

Ser Ala Leu Val Thr Met Met Asp Thr Cys
            180                 185

<210> SEQ ID NO 33
<211> LENGTH: 190
<212> TYPE: PRT
<213> ORGANISM: Curvularia lunata

<400> SEQUENCE: 33

Ala Pro Ala Pro Leu Ser Ala Arg Ala Pro Asn Ile Pro Ser Lys
1               5                   10                  15

Ala Asp Ala Thr Ser Gln Leu Ala Gly Leu Thr Val Ala Ala Gln Gly
            20                  25                  30

Pro Gln Thr Gly Tyr Ser Arg Asp Leu Phe Pro His Trp Ile Thr Gln
        35                  40                  45

Ser Gly Thr Cys Asn Thr Arg Glu Thr Val Leu Lys Arg Asp Gly Thr
50                  55                  60

Asn Val Val Thr Ser Ser Cys Ala Ala Thr Ser Gly Thr Trp Phe
65                  70                  75                  80

Ser Pro Tyr Asp Gly Ala Thr Trp Thr Ala Ala Ser Asp Val Asp Ile
                85                  90                  95

Asp His Val Val Pro Leu Ser Asn Ala Trp Lys Ser Gly Ala Ala Ser
            100                 105                 110

Trp Thr Thr Ala Arg Arg Gln Ala Phe Ala Asn Asp Leu Thr Asn Pro
        115                 120                 125

Gln Leu Ile Ala Val Thr Asp Ser Val Asn Gln Ala Lys Gly Asp Lys
130                 135                 140

Gly Pro Glu Asp Trp Lys Pro Pro Leu Ser Ser Tyr Tyr Cys Thr Tyr
145                 150                 155                 160

Ser Lys Met Trp Ile Lys Val Lys Ser Val Tyr Gly Leu Thr Val Thr
                165                 170                 175

```
Ser Ala Glu Lys Ser Ala Leu Ser Ser Met Leu Ala Thr Cys
            180                 185                 190

<210> SEQ ID NO 34
<211> LENGTH: 191
<212> TYPE: PRT
<213> ORGANISM: Penicillium reticulisporum

<400> SEQUENCE: 34

Leu Pro Ala Pro Glu Ala Leu Pro Ala Pro Pro Gly Val Pro Ser Ala
1               5                   10                  15

Ser Thr Ala Gln Ser Glu Leu Ala Ala Leu Thr Val Ala Ala Gln Gly
            20                  25                  30

Ser Gln Asp Gly Tyr Ser Arg Ser Lys Phe Pro His Trp Ile Thr Gln
            35                  40                  45

Ser Gly Ser Cys Asp Thr Arg Asp Val Val Leu Lys Arg Asp Gly Thr
    50                  55                  60

Asn Val Val Gln Ser Ala Ser Gly Cys Thr Ile Thr Ser Gly Lys Trp
65                  70                  75                  80

Val Ser Pro Tyr Asp Gly Ala Thr Trp Thr Ala Ser Ser Asp Val Asp
                85                  90                  95

Ile Asp His Leu Val Pro Leu Ser Asn Ala Trp Lys Ser Gly Ala Ser
            100                 105                 110

Gly Trp Thr Thr Ala Ala Arg Gln Ala Phe Ala Asn Asp Leu Thr Asn
            115                 120                 125

Pro Gln Leu Leu Val Val Thr Asp Asn Val Asn Glu Ser Lys Gly Asp
            130                 135                 140

Lys Gly Pro Glu Glu Trp Lys Pro Pro Leu Thr Ser Tyr Tyr Cys Thr
145                 150                 155                 160

Tyr Ala Glu Met Trp Val Lys Val Lys Ser Val Tyr Lys Leu Thr Ile
                165                 170                 175

Thr Ser Ala Glu Lys Ser Ala Leu Thr Ser Met Leu Ser Thr Cys
            180                 185                 190

<210> SEQ ID NO 35
<211> LENGTH: 191
<212> TYPE: PRT
<213> ORGANISM: Penicillium quercetorum

<400> SEQUENCE: 35

Leu Pro Ala Pro Glu Pro Ala Pro Ser Pro Gly Ile Pro Ser Ala
1               5                   10                  15

Ser Thr Ala Arg Ser Glu Leu Ala Ser Leu Thr Val Ala Pro Gln Gly
            20                  25                  30

Ser Gln Asp Gly Tyr Ser Arg Ala Lys Phe Pro His Trp Ile Lys Gln
            35                  40                  45

Ser Gly Ser Cys Asp Thr Arg Asp Val Val Leu Glu Arg Asp Gly Thr
    50                  55                  60

Asn Val Val Gln Ser Ser Thr Gly Cys Thr Ile Thr Gly Gly Thr Trp
65                  70                  75                  80

Val Ser Pro Tyr Asp Gly Ala Thr Trp Thr Ala Ser Ser Asp Val Asp
                85                  90                  95

Ile Asp His Leu Val Pro Leu Ser Asn Ala Trp Lys Ser Gly Ala Ser
            100                 105                 110

Ala Trp Thr Thr Ala Gln Arg Gln Ala Phe Ala Asn Asp Leu Thr Asn
            115                 120                 125
```

```
Pro Gln Leu Val Ala Val Thr Asp Asn Val Asn Glu Ala Lys Gly Asp
    130                 135                 140

Lys Gly Pro Glu Glu Trp Lys Pro Pro Leu Thr Ser Tyr Tyr Cys Thr
145                 150                 155                 160

Tyr Ala Glu Met Trp Val Lys Val Lys Ser Val Tyr Lys Leu Thr Ile
                165                 170                 175

Thr Ser Ala Glu Lys Ser Ala Leu Ser Ser Met Leu Asn Thr Cys
            180                 185                 190

<210> SEQ ID NO 36
<211> LENGTH: 192
<212> TYPE: PRT
<213> ORGANISM: Setophaeosphaeria sp.

<400> SEQUENCE: 36

Leu Pro Ala Pro Val Thr Leu Glu Ala Arg Ala Pro Pro Asn Ile Pro
1               5                   10                  15

Ser Thr Ala Ser Ala Asn Thr Leu Leu Ala Gly Leu Thr Val Ala Ala
            20                  25                  30

Gln Gly Ser Gln Thr Gly Tyr Ser Arg Asp Leu Phe Pro His Trp Ile
        35                  40                  45

Thr Gln Ser Gly Thr Cys Asn Thr Arg Glu Thr Val Leu Lys Arg Asp
    50                  55                  60

Gly Thr Gly Val Val Thr Asp Ser Ala Cys Ala Ser Thr Ser Gly Ser
65                  70                  75                  80

Trp Tyr Ser Val Tyr Asp Gly Ala Thr Trp Thr Ala Ala Ser Asp Val
                85                  90                  95

Asp Ile Asp His Val Val Pro Leu Ser Asn Ala Trp Lys Ser Gly Ala
            100                 105                 110

Ala Ser Trp Thr Thr Ala Arg Arg Gln Ser Phe Ala Asn Asp Leu Thr
        115                 120                 125

Asn Pro Gln Leu Ile Ala Val Thr Asp Asn Val Asn Gln Ala Lys Gly
    130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ser Leu Thr
                165                 170                 175

Ile Thr Ser Ala Glu Lys Thr Ala Leu Thr Ser Met Leu Asn Thr Cys
            180                 185                 190

<210> SEQ ID NO 37
<211> LENGTH: 192
<212> TYPE: PRT
<213> ORGANISM: Alternaria sp. XZ2545

<400> SEQUENCE: 37

Leu Pro Ala Pro Val Thr Leu Glu Ala Arg Ala Pro Pro Asn Ile Pro
1               5                   10                  15

Thr Thr Ala Ala Ala Lys Thr Gln Leu Ala Gly Leu Thr Val Ala Ala
            20                  25                  30

Gln Gly Pro Gln Thr Gly Tyr Ser Arg Asp Leu Phe Pro His Trp Ile
        35                  40                  45

Thr Gln Ser Gly Thr Cys Asn Thr Arg Glu Thr Val Leu Lys Arg Asp
    50                  55                  60

Gly Thr Gly Val Val Thr Asp Ser Ala Cys Ala Ser Thr Ser Gly Ser
65                  70                  75                  80
```

```
Trp Phe Ser Val Tyr Asp Gly Ala Thr Trp Thr Ala Ala Ser Asp Val
                85                  90                  95

Asp Ile Asp His Val Val Pro Leu Ser Asn Ala Trp Lys Ser Gly Ala
            100                 105                 110

Ala Ser Trp Thr Thr Ala Arg Arg Gln Ser Phe Ala Asn Asp Leu Thr
        115                 120                 125

Asn Pro Gln Leu Ile Ala Val Thr Asp Asn Val Asn Gln Ala Lys Gly
    130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ala Leu Thr
                165                 170                 175

Ile Thr Ser Ala Glu Lys Thr Ala Leu Thr Ser Met Leu Asn Thr Cys
            180                 185                 190

<210> SEQ ID NO 38
<211> LENGTH: 192
<212> TYPE: PRT
<213> ORGANISM: Alternaria sp.

<400> SEQUENCE: 38

Leu Pro Ala Pro Val Thr Leu Glu Ala Arg Ala Pro Asn Ile Pro
1               5                   10                  15

Thr Thr Ala Ala Ala Lys Thr Gln Leu Ala Gly Leu Thr Val Ala Ala
                20                  25                  30

Gln Gly Pro Gln Thr Gly Tyr Ser Arg Asp Leu Phe Pro His Trp Ile
            35                  40                  45

Thr Gln Ser Gly Ser Cys Asn Thr Arg Glu Val Val Leu Gln Arg Asp
    50                  55                  60

Gly Thr Gly Val Val Thr Asp Ser Ala Cys Ala Ala Thr Ser Gly Ser
65                  70                  75                  80

Trp Tyr Ser Val Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
            100                 105                 110

Ala Ser Trp Thr Thr Ala Arg Arg Gln Ala Phe Ala Asn Asp Leu Thr
        115                 120                 125

Asn Pro Gln Leu Leu Ala Val Thr Asp Asn Val Asn Gln Ala Lys Gly
    130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ala Leu Thr
                165                 170                 175

Ile Thr Ser Ala Glu Lys Thr Ala Leu Thr Ser Met Leu Asn Thr Cys
            180                 185                 190

<210> SEQ ID NO 39
<211> LENGTH: 186
<212> TYPE: PRT
<213> ORGANISM: Trichoderma reesei

<400> SEQUENCE: 39

Ala Pro Leu Pro Ala Pro Pro Gly Ile Pro Ser Glu Asp Thr Ala Arg
1               5                   10                  15

Thr Gln Leu Ala Gly Leu Thr Val Ala Val Val Gly Ser Gly Thr Gly
                20                  25                  30
```

-continued

Tyr Ser Arg Asp Leu Phe Pro Thr Trp Asp Ala Ile Ser Gly Asn Cys
        35                  40                  45

Asn Ala Arg Glu Tyr Val Leu Lys Arg Asp Gly Glu Gly Val Gln Val
 50                  55                  60

Asn Asn Ala Cys Glu Ala Gln Ser Gly Ser Trp Ile Ser Pro Tyr Asp
 65                  70                  75                  80

Asn Ala Ser Phe Thr Asn Ala Ser Ser Leu Asp Ile Asp His Met Val
                 85                  90                  95

Pro Leu Lys Asn Ala Trp Ile Ser Gly Ala Ser Thr Trp Thr Thr Ala
                100                 105                 110

Gln Arg Glu Ala Leu Ala Asn Asp Val Ser Arg Pro Gln Leu Trp Ala
            115                 120                 125

Val Ser Ala Ser Ser Asn Arg Ser Lys Gly Asp Arg Ser Pro Asp Gln
130                 135                 140

Trp Lys Pro Pro Leu Thr Ser Phe Tyr Cys Thr Tyr Ala Lys Ser Trp
145                 150                 155                 160

Ile Asp Val Lys Ser Tyr Tyr Lys Leu Thr Ile Ser Ala Glu Lys
                165                 170                 175

Thr Ala Leu Ser Ser Met Leu Asp Thr Cys
            180                 185

<210> SEQ ID NO 40
<211> LENGTH: 188
<212> TYPE: PRT
<213> ORGANISM: Chaetomium thermophilum

<400> SEQUENCE: 40

Ala Pro Ala Pro Gln Pro Thr Pro Pro Gly Ile Pro Ser Arg Ser Thr
1               5                   10                  15

Ala Gln Ser Tyr Leu Asn Ser Leu Thr Val Ala Ala Ser Tyr Asp Asp
            20                  25                  30

Gly Asn Tyr Asn Arg Asp Leu Phe Pro His Trp Asn Thr Val Ser Gly
        35                  40                  45

Thr Cys Asn Thr Arg Glu Tyr Val Leu Lys Arg Asp Gly Ser Asn Val
 50                  55                  60

Val Thr Asn Ser Ala Cys Gln Ala Thr Ser Gly Thr Trp Tyr Ser Pro
 65                  70                  75                  80

Tyr Asp Gly Ala Thr Trp Thr Ala Ala Ser Asp Ile Asp Ile Asp His
                 85                  90                  95

Met Val Pro Leu Lys Asn Ala Trp Ile Ser Gly Ala Asn Thr Trp Ser
                100                 105                 110

Ser Ser Lys Arg Ser Ser Phe Ala Asn Asp Ile Asn Ser Pro Gln Leu
            115                 120                 125

Trp Ala Val Thr Asp Ser Val Asn Gln Ser Lys Gly Asp Lys Ser Pro
130                 135                 140

Asp Lys Trp Lys Pro Pro Leu Thr Thr Phe Tyr Cys Thr Tyr Ala Lys
145                 150                 155                 160

Ser Trp Ile Thr Val Lys Tyr Asn Tyr Asn Leu Thr Ile Thr Ser Ala
                165                 170                 175

Glu Lys Ser Ala Leu Gln Asn Met Ile Asn Thr Cys
            180                 185

<210> SEQ ID NO 41
<211> LENGTH: 190
<212> TYPE: PRT

<213> ORGANISM: Scytalidium thermophilum

<400> SEQUENCE: 41

| | | | | | | | | | | | | |
|---|---|---|---|---|---|---|---|---|---|---|---|---|
| Leu | Pro | Ala | Pro | Ala | Pro | Met | Pro | Thr | Pro | Gly | Ile | Pro | Ser | Lys |
| 1 | | | | 5 | | | | | 10 | | | | | 15 |

Ser Thr Ala Gln Ser Gln Leu Asn Ala Leu Thr Val Lys Ala Ser Tyr
            20               25               30

Asp Asp Gly Lys Tyr Lys Arg Asp Leu Phe Pro His Trp Asn Thr Val
            35               40               45

Ser Gly Thr Cys Asn Thr Arg Glu Tyr Val Leu Lys Arg Asp Gly Val
50               55               60

Asn Val Val Thr Asn Ser Ala Cys Ala Ala Thr Ser Gly Thr Trp Tyr
65               70               75               80

Ser Pro Phe Asp Gly Ala Thr Trp Thr Ala Ser Asp Val Asp Ile
            85               90               95

Asp His Met Val Pro Leu Lys Asn Ala Trp Ile Ser Gly Ala Asn Asn
            100           105           110

Trp Thr Ser Thr Lys Arg Thr Gln Phe Ala Asn Asp Ile Asn Leu Pro
            115           120           125

Gln Leu Trp Ala Val Thr Asp Asp Val Asn Gln Ala Lys Gly Asp Lys
    130              135           140

Ser Pro Asp Lys Trp Lys Pro Pro Leu Thr Ser Phe Tyr Cys Thr Tyr
145              150           155               160

Ala Lys Ser Trp Ile Thr Val Lys Tyr Asn Tyr Gly Leu Ser Ile Thr
            165           170           175

Ser Ala Glu Lys Ser Ala Leu Thr Ser Met Ile Asn Thr Cys
        180              185           190

<210> SEQ ID NO 42
<211> LENGTH: 186
<212> TYPE: PRT
<213> ORGANISM: Metapochonia suchlasporia

<400> SEQUENCE: 42

Val Pro Val Pro Ala Pro Gly Ile Pro Ser Thr Ser Thr Ala Lys
1               5               10               15

Thr Leu Leu Ala Gly Leu Lys Val Ala Val Pro Leu Ser Gly Asp Gly
            20               25               30

Tyr Ser Arg Glu Lys Phe Pro Leu Trp Glu Thr Ile Gln Gly Thr Cys
            35               40               45

Asn Ala Arg Glu Phe Val Leu Lys Arg Asp Gly Thr Asp Val Lys Thr
50               55               60

Asn Asn Ala Cys Val Ala Glu Ser Gly Asn Trp Val Ser Pro Tyr Asp
65               70               75               80

Gly Val Lys Phe Thr Ala Ala Arg Asp Leu Asp Ile Asp His Met Val
            85               90               95

Pro Leu Lys Asn Ala Trp Ile Ser Gly Ala Ser Gln Thr Thr Glu
            100           105           110

Arg Arg Lys Ala Leu Ala Asn Asp Ile Thr Arg Pro Gln Leu Trp Ala
            115           120           125

Val Ser Ala His Ala Asn Arg Gly Lys Ser Asp Asp Ser Pro Asp Glu
    130              135           140

Trp Lys Pro Pro Leu Lys Thr Phe Trp Cys Thr Tyr Ala Lys Ser Trp
145              150           155               160

Val Gln Val Lys Ser Phe Tyr Glu Leu Thr Ile Thr Asp Ala Glu Lys

```
                    165                 170                 175

Gly Ala Leu Ala Gly Met Leu Asp Ser Cys
            180                 185

<210> SEQ ID NO 43
<211> LENGTH: 198
<212> TYPE: PRT
<213> ORGANISM: Daldinia fissa

<400> SEQUENCE: 43

Ala Pro Ala Pro Ile Pro Val Ala Glu Pro Ala Pro Met Pro Met Pro
1               5                   10                  15

Thr Pro Pro Gly Ile Pro Ser Ala Ser Ala Lys Ser Gln Leu Ala
            20                  25                  30

Ser Leu Thr Val Lys Ala Ala Val Asp Asp Gly Gly Tyr Gln Arg Asp
            35                  40                  45

Leu Phe Pro Thr Trp Asp Thr Ile Thr Gly Thr Cys Asn Thr Arg Glu
        50                  55                  60

Tyr Val Leu Lys Arg Asp Gly Ala Asn Val Gln Val Gly Ser Asp Cys
65                  70                  75                  80

Tyr Pro Thr Ser Gly Thr Trp Thr Ser Pro Tyr Asp Gly Gly Lys Trp
                85                  90                  95

Thr Ser Pro Ser Asp Val Asp Ile Asp His Met Val Pro Leu Lys Asn
            100                 105                 110

Ala Trp Val Ser Gly Ala Asn Lys Trp Thr Thr Ala Lys Arg Glu Gln
        115                 120                 125

Phe Ala Asn Asp Val Asp Arg Pro Gln Leu Trp Ala Val Thr Asp Asn
130                 135                 140

Val Asn Ser Ser Lys Gly Asp Lys Ser Pro Asp Thr Trp Lys Pro Pro
145                 150                 155                 160

Leu Thr Ser Phe Tyr Cys Thr Tyr Ala Ser Ala Tyr Val Ala Val Lys
                165                 170                 175

Ser Tyr Trp Gly Leu Thr Ile Thr Ser Ala Glu Lys Ser Ala Leu Ser
            180                 185                 190

Asp Met Leu Gly Thr Cys
            195

<210> SEQ ID NO 44
<211> LENGTH: 188
<212> TYPE: PRT
<213> ORGANISM: Acremonium sp. XZ2007

<400> SEQUENCE: 44

Leu Pro Leu Gln Ser Arg Asp Pro Pro Gly Ile Pro Ser Thr Ala Thr
1               5                   10                  15

Ala Lys Ser Leu Leu Asn Gly Leu Thr Val Lys Ala Trp Ser Asn Glu
            20                  25                  30

Gly Thr Tyr Asp Arg Asp Leu Phe Pro His Trp Gln Thr Ile Glu Gly
            35                  40                  45

Thr Cys Asn Ala Arg Glu Tyr Val Leu Lys Arg Asp Gly Gln Asn Val
        50                  55                  60

Val Val Asn Ser Ala Cys Thr Ala Gln Ser Gly Thr Trp Lys Ser Val
65                  70                  75                  80

Tyr Asp Gly Glu Thr Thr Asn Ser Ala Ser Asp Leu Asp Ile Asp His
                85                  90                  95

Met Ile Pro Leu Lys Asn Ala Trp Ile Ser Gly Ala Ala Thr Trp Thr
```

```
                    100                 105                 110

Thr Ala Gln Arg Thr Ser Phe Ala Asn Asp Ile Ser Ser Pro Gln Leu
                115                 120                 125

Trp Ala Val Thr Ala Gly Val Asn Arg Ser Lys Ser Asp Arg Ser Pro
130                 135                 140

Asp Thr Trp Val Pro Pro Leu Ala Ser Phe His Cys Thr Tyr Gly Lys
145                 150                 155                 160

Ala Trp Val Gln Val Lys Ser Lys Trp Ala Leu Ser Ile Thr Ser Ala
                165                 170                 175

Glu Lys Ser Ala Leu Thr Gly Leu Leu Asn Lys Cys
                180                 185

<210> SEQ ID NO 45
<211> LENGTH: 182
<212> TYPE: PRT
<213> ORGANISM: Acremonium dichromosporum

<400> SEQUENCE: 45

Ile Pro Pro Gly Ile Pro Ser Glu Ala Thr Ala Arg Ser Leu Leu Ser
1               5                   10                  15

Ser Leu Thr Val Ala Pro Thr Val Asp Asp Gly Thr Tyr Asp Arg Asp
                20                  25                  30

Leu Phe Pro His Trp Ser Ser Val Glu Gly Asn Cys Asn Ala Arg Glu
            35                  40                  45

Phe Val Leu Arg Arg Asp Gly Asp Gly Val Ser Val Gly Asn Asp Cys
        50                  55                  60

Tyr Pro Thr Ala Gly Thr Trp Thr Cys Pro Tyr Asp Gly Lys Arg His
65                  70                  75                  80

Ser Val Pro Ser Asp Val Ser Ile Asp His Met Val Pro Leu His Asn
                85                  90                  95

Ala Trp Met Thr Gly Ala Ser Glu Trp Thr Thr Ala Glu Arg Glu Ala
                100                 105                 110

Phe Ala Asn Asp Ile Asp Gly Pro Gln Leu Trp Ala Val Thr Ser Thr
            115                 120                 125

Thr Asn Ser Gln Lys Gly Ser Asp Ala Pro Asp Glu Trp Gln Pro Pro
        130                 135                 140

Gln Thr Ser Ile His Cys Lys Tyr Ala Ala Trp Ile Gln Val Lys
145                 150                 155                 160

Ser Thr Tyr Asp Leu Thr Val Ser Ser Ala Glu Gln Ala Ala Leu Glu
                165                 170                 175

Glu Met Leu Gly Arg Cys
            180

<210> SEQ ID NO 46
<211> LENGTH: 188
<212> TYPE: PRT
<213> ORGANISM: Sarocladium sp. XZ2014

<400> SEQUENCE: 46

Val Pro Ile Pro Leu Pro Asp Pro Pro Gly Ile Pro Ser Ser Ser Thr
1               5                   10                  15

Ala Asn Thr Leu Leu Ala Gly Leu Thr Val Arg Ala Ser Ser Asn Glu
                20                  25                  30

Asp Thr Tyr Asn Arg Asp Leu Phe Pro His Trp Val Ala Ile Ser Gly
            35                  40                  45

Asn Cys Asn Ala Arg Glu Tyr Val Leu Arg Arg Asp Gly Thr Asn Val
```

```
            50                  55                  60
Val Val Asn Thr Ala Cys Val Pro Gln Ser Gly Thr Trp Arg Ser Pro
 65                  70                  75                  80

Tyr Asp Gly Glu Ser Thr Thr Asn Ala Ser Asp Leu Asp Ile Asp His
                     85                  90                  95

Met Val Pro Leu Lys Asn Ala Trp Ile Ser Gly Ala Ala Ser Trp Thr
                    100                 105                 110

Thr Ala Lys Arg Gln Asp Phe Ala Asn Asp Val Ser Gly Pro Gln Leu
                115                 120                 125

Trp Ala Val Thr Ala Gly Val Asn Arg Ser Lys Gly Asp Lys Ser Pro
            130                 135                 140

Asp Ser Trp Val Pro Pro Leu Ala Ser Phe His Cys Thr Tyr Ala Arg
145                 150                 155                 160

Ser Trp Ile Gln Val Lys Ser Ser Trp Ala Leu Ser Val Thr Ser Ala
                    165                 170                 175

Glu Lys Ala Ala Leu Thr Asp Leu Leu Ser Thr Cys
                180                 185

<210> SEQ ID NO 47
<211> LENGTH: 186
<212> TYPE: PRT
<213> ORGANISM: Metarhizium sp. HNA15-2

<400> SEQUENCE: 47

Val Pro Val Pro Ala Pro Pro Gly Ile Pro Thr Ala Ser Thr Ala Arg
 1               5                  10                  15

Thr Leu Leu Ala Gly Leu Lys Val Ala Thr Pro Leu Ser Gly Asp Gly
                 20                  25                  30

Tyr Ser Arg Thr Leu Phe Pro Thr Trp Glu Thr Ile Glu Gly Thr Cys
             35                  40                  45

Asn Ala Arg Glu Phe Val Leu Lys Arg Asp Gly Thr Asp Val Gln Thr
         50                  55                  60

Asn Thr Ala Cys Val Ala Gln Ser Gly Asn Trp Val Ser Pro Tyr Asp
 65                  70                  75                  80

Gly Val Ala Phe Thr Ala Ala Ser Asp Leu Asp Ile Asp His Met Val
                     85                  90                  95

Pro Leu Lys Asn Ala Trp Ile Ser Gly Ala Ser Gln Trp Thr Thr Asp
                    100                 105                 110

Lys Arg Lys Gly Leu Ala Asn Asp Ile Thr Arg Pro Gln Leu Trp Ala
                115                 120                 125

Val Ser Ala His Ala Asn Arg Ala Lys Gly Asp Ser Ser Pro Asp Glu
            130                 135                 140

Trp Lys Pro Pro Leu Lys Thr Phe Trp Cys Thr Tyr Ala Arg Ser Trp
145                 150                 155                 160

Val Gln Val Lys Ser Tyr Tyr Ala Leu Thr Ile Thr Asp Ala Glu Lys
                    165                 170                 175

Gly Ala Leu Ser Gly Met Leu Asp Ser Cys
                180                 185

<210> SEQ ID NO 48
<211> LENGTH: 188
<212> TYPE: PRT
<213> ORGANISM: Acremonium sp. XZ2414

<400> SEQUENCE: 48

Ala Pro Ile Ala Val Arg Asp Pro Pro Gly Ile Pro Ser Ala Ser Thr
```

```
  1               5                   10                  15
Ala Asn Thr Leu Leu Ala Gly Leu Thr Val Arg Ala Ser Ser Asn Glu
            20                  25                  30

Asp Ser Tyr Asp Arg Asn Leu Phe Pro His Trp Ser Ala Ile Ser Gly
            35                  40                  45

Asn Cys Asn Ala Arg Glu Phe Val Leu Glu Arg Asp Gly Thr Asn Val
 50                  55                  60

Val Val Asn Asn Ala Cys Val Ala Gln Ser Gly Thr Trp Arg Ser Pro
 65                  70                  75                  80

Tyr Asp Gly Glu Thr Thr Gly Asn Ala Ser Asp Leu Asp Ile Asp His
            85                  90                  95

Met Val Pro Leu Lys Asn Ala Trp Ile Ser Gly Ala Ser Ser Trp Ser
            100                 105                 110

Thr Thr Arg Arg Gln Glu Phe Ala Asn Asp Val Ser Gly Pro Gln Leu
            115                 120                 125

Trp Ala Val Thr Ala Gly Val Asn Arg Ser Lys Gly Asp Arg Ser Pro
130                 135                 140

Asp Ser Trp Val Pro Pro Leu Ala Ser Phe His Cys Thr Tyr Ala Lys
145                 150                 155                 160

Ser Trp Val Gln Val Lys Ser Ser Trp Ser Leu Ser Val Thr Ser Ala
            165                 170                 175

Glu Lys Ala Ala Leu Ser Asp Leu Leu Gly Thr Cys
            180                 185

<210> SEQ ID NO 49
<211> LENGTH: 186
<212> TYPE: PRT
<213> ORGANISM: Isaria tenuipes

<400> SEQUENCE: 49

Ala Pro Val Pro Glu Pro Pro Gly Ile Pro Ser Thr Ser Thr Ala Gln
 1               5                  10                  15

Ser Asp Leu Asn Ser Leu Gln Val Ala Ala Ser Gly Ser Gly Asp Gly
            20                  25                  30

Tyr Ser Arg Ala Glu Phe Pro His Trp Val Ser Val Glu Gly Ser Cys
            35                  40                  45

Asp Ser Arg Glu Tyr Val Leu Lys Arg Asp Gly Gln Asp Val Gln Ala
 50                  55                  60

Asp Ser Ser Cys Lys Ile Thr Ser Gly Thr Trp Val Ser Pro Tyr Asp
65                  70                  75                  80

Ala Thr Thr Trp Thr Asn Ser Ser Lys Val Asp Ile Asp His Leu Val
            85                  90                  95

Pro Leu Lys Asn Ala Trp Ile Ser Gly Ala Ser Ser Trp Thr Lys Ala
            100                 105                 110

Gln Arg Gln Asp Phe Ala Asn Asp Ile Lys Arg Pro Gln Leu Tyr Ala
            115                 120                 125

Val Ser Glu Asn Ala Asn Arg Ser Lys Gly Asp Arg Ser Pro Asp Gly
            130                 135                 140

Trp Lys Pro Pro Leu Lys Ser Phe Tyr Cys Thr Tyr Ala Lys Ser Trp
145                 150                 155                 160

Val Ala Val Lys Ser Tyr Tyr Lys Leu Thr Ile Thr Ser Ala Glu Lys
            165                 170                 175

Ser Ala Leu Gly Asp Met Leu Asp Thr Cys
            180                 185
```

<210> SEQ ID NO 50
<211> LENGTH: 184
<212> TYPE: PRT
<213> ORGANISM: Scytalidium circinatum

<400> SEQUENCE: 50

Ala Pro Pro Gly Ile Pro Ser Ala Ser Thr Ala Ser Ser Leu Leu Gly
1               5                   10                  15

Glu Leu Ala Val Ala Glu Pro Val Asp Asp Gly Ser Tyr Asp Arg Asp
            20                  25                  30

Leu Phe Pro His Trp Glu Pro Ile Pro Gly Glu Thr Ala Cys Ser Ala
        35                  40                  45

Arg Glu Tyr Val Leu Arg Arg Asp Gly Thr Gly Val Glu Thr Gly Ser
    50                  55                  60

Asp Cys Tyr Pro Thr Ser Gly Thr Trp Ser Ser Pro Tyr Asp Gly Gly
65                  70                  75                  80

Ser Trp Thr Ala Pro Ser Asp Val Asp Ile Asp His Met Val Pro Leu
                85                  90                  95

Lys Asn Ala Trp Ile Ser Gly Ala Ser Glu Trp Thr Thr Ala Glu Arg
            100                 105                 110

Glu Ala Phe Ala Asn Asp Ile Asp Gly Pro Gln Leu Trp Ala Val Thr
        115                 120                 125

Asp Glu Val Asn Gln Ser Lys Ser Asp Gln Ser Pro Asp Glu Trp Lys
    130                 135                 140

Pro Pro Leu Ser Ser Phe Tyr Cys Thr Tyr Ala Cys Ala Trp Ile Gln
145                 150                 155                 160

Val Lys Ser Thr Tyr Ser Leu Ser Ile Ser Ser Ala Glu Gln Ala Ala
                165                 170                 175

Leu Glu Asp Met Leu Gly Ser Cys
            180

<210> SEQ ID NO 51
<211> LENGTH: 186
<212> TYPE: PRT
<213> ORGANISM: Metarhizium lepidiotae

<400> SEQUENCE: 51

Val Pro Val Pro Ala Pro Pro Gly Ile Pro Thr Ala Ser Thr Ala Arg
1               5                   10                  15

Thr Leu Leu Ala Gly Leu Lys Val Ala Thr Pro Leu Ser Gly Asp Gly
            20                  25                  30

Tyr Ser Arg Thr Leu Phe Pro Thr Trp Glu Thr Ile Glu Gly Thr Cys
        35                  40                  45

Asn Ala Arg Glu Phe Val Leu Lys Arg Asp Gly Thr Asp Val Gln Thr
    50                  55                  60

Asn Thr Ala Cys Val Ala Glu Ser Gly Asn Trp Val Ser Pro Tyr Asp
65                  70                  75                  80

Gly Val Ser Phe Thr Ala Ala Ser Asp Leu Asp Ile Asp His Met Val
                85                  90                  95

Pro Leu Lys Asn Ala Trp Ile Ser Gly Ala Ser Gln Trp Thr Thr Asp
            100                 105                 110

Lys Arg Lys Asp Leu Ala Asn Asp Ile Thr Arg Pro Gln Leu Trp Ala
        115                 120                 125

Val Ser Ala His Ala Asn Arg Ser Lys Gly Asp Ser Pro Asp Glu
    130                 135                 140

```
Trp Lys Pro Pro Leu Gln Thr Phe Trp Cys Thr Tyr Ser Lys Ser Trp
145                 150                 155                 160

Ile Gln Val Lys Ser His Tyr Ser Leu Thr Ile Thr Asp Ala Glu Lys
                165                 170                 175

Gly Ala Leu Ser Gly Met Leu Asp Ser Cys
            180                 185
```

<210> SEQ ID NO 52
<211> LENGTH: 226
<212> TYPE: PRT
<213> ORGANISM: Thermobispora bispora

<400> SEQUENCE: 52

```
Leu Asp Ile Ala Asp Gly Arg Pro Ala Gly Gly Lys Ala Ala Glu Ala
1               5                   10                  15

Ala Thr Gly Thr Ser Pro Leu Ala Asn Pro Asp Gly Thr Arg Pro Gly
                20                  25                  30

Leu Ala Ala Ile Thr Ser Ala Asp Glu Arg Ala Glu Ala Arg Ala Leu
            35                  40                  45

Ile Glu Arg Leu Arg Thr Lys Gly Arg Gly Pro Lys Thr Gly Tyr Glu
50                  55                  60

Arg Glu Lys Phe Gly Tyr Ala Trp Ala Asp Ser Val Asp Gly Ile Pro
65                  70                  75                  80

Phe Gly Arg Asn Gly Cys Asp Thr Arg Asn Asp Val Leu Lys Arg Asp
                85                  90                  95

Gly Gln Arg Leu Gln Phe Arg Ser Gly Ser Asp Cys Val Val Ile Ser
            100                 105                 110

Met Thr Leu Phe Asp Pro Tyr Thr Gly Lys Thr Ile Glu Trp Thr Lys
        115                 120                 125

Gln Asn Ala Ala Glu Val Gln Ile Asp His Val Val Pro Leu Ser Tyr
    130                 135                 140

Ser Trp Gln Met Gly Ala Ser Arg Trp Ser Asp Glu Lys Arg Arg Gln
145                 150                 155                 160

Leu Ala Asn Asp Pro Leu Asn Leu Met Pro Val Asp Gly Ala Thr Asn
                165                 170                 175

Ser Arg Lys Gly Asp Ser Gly Pro Ala Ser Trp Leu Pro Pro Arg Arg
            180                 185                 190

Glu Ile Arg Cys Ala Tyr Val Val Arg Phe Ala Gln Val Ala Leu Lys
        195                 200                 205

Tyr Asp Leu Pro Val Thr Thr Ala Asp Lys Glu Thr Met Leu Gln Gln
    210                 215                 220

Cys Ser
225
```

<210> SEQ ID NO 53
<211> LENGTH: 191
<212> TYPE: PRT
<213> ORGANISM: Sporormia fimetaria

<400> SEQUENCE: 53

```
Leu Pro Ala Pro Val Leu Glu Lys Arg Thr Pro Pro Asn Ile Pro Ser
1               5                   10                  15

Thr Ser Thr Ala Gln Ser Leu Leu Ser Gly Leu Thr Val Ala Pro Gln
                20                  25                  30

Gly Ser Gln Thr Gly Tyr Ser Arg Asp Leu Phe Pro His Trp Ile Thr
            35                  40                  45
```

```
Val Ser Gly Thr Cys Asn Thr Arg Glu Thr Val Leu Lys Arg Asp Gly
     50                  55                  60

Ser Asn Val Val Thr Asp Ser Ala Cys Ala Ser Val Ser Gly Ser Trp
 65                  70                  75                  80

Tyr Ser Thr Tyr Asp Gly Ala Thr Trp Thr Ala Ala Ser Asp Val Asp
                 85                  90                  95

Ile Asp His Val Val Pro Leu Ser Asn Ala Trp Lys Ser Gly Ala Ala
                100                 105                 110

Ser Trp Thr Thr Ala Arg Arg Gln Ala Phe Ala Asn Asp Leu Thr Asn
                115                 120                 125

Pro Gln Leu Ile Ala Val Thr Asp Asn Val Asn Gln Ala Lys Gly Asp
130                 135                 140

Gln Gly Pro Glu Ser Trp Lys Pro Pro Leu Thr Ser Tyr Tyr Cys Thr
145                 150                 155                 160

Tyr Ala Lys Met Trp Val Lys Val Lys Ser Val Tyr Ser Leu Thr Val
                165                 170                 175

Thr Ser Ala Glu Lys Ser Ala Leu Ser Ser Met Leu Gly Thr Cys
                180                 185                 190
```

<210> SEQ ID NO 54
<211> LENGTH: 193
<212> TYPE: PRT
<213> ORGANISM: Pycnidiophora cf.dispera

<400> SEQUENCE: 54

```
Leu Pro Ala Pro Ala Pro Val Leu Val Ala Arg Glu Pro Pro Asn Ile
 1               5                  10                  15

Pro Ser Thr Ser Ser Ala Gln Ser Met Leu Ser Gly Leu Thr Val Lys
                20                  25                  30

Ala Gln Gly Pro Gln Asp Gly Tyr Ser Arg Asp Leu Phe Pro His Trp
             35                  40                  45

Ile Thr Ile Ser Gly Thr Cys Asn Thr Arg Glu Thr Val Leu Lys Arg
         50                  55                  60

Asp Gly Thr Asn Val Val Thr Asn Ser Ala Cys Ala Ser Thr Ser Gly
 65                  70                  75                  80

Ser Trp Tyr Ser Pro Tyr Asp Gly Ala Thr Trp Thr Ala Ala Ser Asp
                 85                  90                  95

Val Asp Ile Asp His Ile Val Pro Leu Ser Asn Ala Trp Lys Ser Gly
                100                 105                 110

Ala Ala Ser Trp Thr Thr Ser Arg Arg Gln Gln Phe Ala Asn Asp Leu
             115                 120                 125

Thr Asn Pro Gln Leu Ile Ala Val Thr Asp Ser Val Asn Gln Ala Lys
130                 135                 140

Gly Asp Lys Gly Pro Glu Asp Trp Lys Pro Ser Arg Thr Ser Tyr His
145                 150                 155                 160

Cys Thr Tyr Ala Lys Met Trp Ile Lys Val Lys Ser Val Tyr Ser Leu
                165                 170                 175

Thr Val Thr Ser Ala Glu Lys Ser Ala Leu Thr Thr Met Leu Asn Thr
                180                 185                 190

Cys
```

<210> SEQ ID NO 55
<211> LENGTH: 199
<212> TYPE: PRT
<213> ORGANISM: Enviromental sample D

<400> SEQUENCE: 55

```
Asp Thr Asp Pro Glu Pro Val Ala Gly Ser Ala Leu Glu Ala Leu Ala
1               5                   10                  15

Gly Leu Glu Val Lys Gly Pro Gly Pro Asp Thr Gly Tyr Glu Arg Ala
            20                  25                  30

Leu Phe Gly Pro Pro Trp Ala Asp Val Asp Gly Asn Gly Cys Asp Thr
        35                  40                  45

Arg Asn Asp Ile Leu Ala Arg Asp Leu Thr Asp Leu Thr Phe Ser Thr
    50                  55                  60

Arg Gly Asp Val Cys Glu Val Arg Thr Gly Thr Phe Asp Asp Pro Tyr
65                  70                  75                  80

Thr Gly Glu Thr Ile Asp Phe Arg Arg Gly Asn Ala Thr Ser Ala Ala
                85                  90                  95

Val Gln Ile Asp His Val Val Pro Leu Leu Asp Ala Trp Arg Lys Gly
            100                 105                 110

Ala Arg Ala Trp Asp Asp Glu Thr Arg Arg Gln Phe Ala Asn Asp Pro
        115                 120                 125

Leu Asn Leu Leu Ala Ser Asp Gly Pro Ala Asn Gln Ser Lys Gly Ala
    130                 135                 140

Arg Asp Ala Ser Ala Trp Leu Pro Pro Asn His Ala Phe Arg Cys Pro
145                 150                 155                 160

Tyr Val Ala Arg Gln Ile Ala Val Lys Ala Ala Tyr Glu Leu Ser Val
                165                 170                 175

Thr Pro Ser Glu Ser Glu Ala Met Ala Arg Val Leu Ala Asp Cys Pro
            180                 185                 190

Ala Glu Pro Leu Pro Ala Gly
        195
```

<210> SEQ ID NO 56
<211> LENGTH: 199
<212> TYPE: PRT
<213> ORGANISM: Enviromental sample O

<400> SEQUENCE: 56

```
Asp Asp Glu Pro Glu Pro Ala Arg Gly Ser Ala Leu Glu Ala Leu Ala
1               5                   10                  15

Arg Leu Glu Val Val Gly Pro Gly Pro Asp Thr Gly Tyr Glu Arg Glu
            20                  25                  30

Leu Phe Gly Pro Ala Trp Ala Asp Val Asp Gly Asn Gly Cys Asp Thr
        35                  40                  45

Arg Asn Asp Ile Leu Ala Arg Asp Leu Thr Asp Leu Thr Phe Ser Thr
    50                  55                  60

Arg Gly Glu Val Cys Glu Val Arg Thr Gly Thr Phe Gln Asp Pro Tyr
65                  70                  75                  80

Thr Gly Glu Thr Ile Asp Phe Arg Arg Gly Asn Ala Thr Ser Met Ala
                85                  90                  95

Val Gln Ile Asp His Val Val Pro Leu Met Asp Ala Trp Arg Lys Gly
            100                 105                 110

Ala Arg Ala Trp Asp Asp Glu Thr Arg Arg Gln Phe Ala Asn Asp Pro
        115                 120                 125

Leu Asn Leu Leu Ala Ser Asp Gly Pro Ala Asn Gln Ser Lys Gly Ala
    130                 135                 140

Arg Asp Ala Ser Ala Trp Leu Pro Pro Asn His Ala Phe Arg Cys Pro
145                 150                 155                 160
```

Tyr Val Ala Arg Gln Ile Ala Val Lys Thr Ala Tyr Glu Leu Ser Val
                165                 170                 175

Thr Pro Ser Glu Ser Glu Ala Met Ala Arg Val Leu Glu Asp Cys Pro
            180                 185                 190

Ala Glu Pro Val Pro Ala Gly
        195

<210> SEQ ID NO 57
<211> LENGTH: 186
<212> TYPE: PRT
<213> ORGANISM: Clavicipitaceae sp-70249

<400> SEQUENCE: 57

Val Pro Val Pro Ala Pro Gly Ile Pro Ser Thr Ser Thr Ala Lys
1               5                   10                  15

Thr Leu Leu Ala Gly Leu Lys Val Ala Thr Pro Leu Ser Gly Asp Gly
            20                  25                  30

Tyr Ser Arg Asp Lys Phe Pro Thr Trp Glu Thr Ile Gln Gly Thr Cys
        35                  40                  45

Asn Ala Arg Glu Phe Val Ile Lys Arg Asp Gly Thr Asp Val Lys Thr
50                  55                  60

Asn Ser Ala Cys Val Ala Glu Ser Gly Asn Trp Val Ser Pro Tyr Asp
65                  70                  75                  80

Gly Val Lys Phe Thr Ala Ala Arg Asp Leu Asp Ile Asp His Met Val
                85                  90                  95

Pro Leu Lys Asn Ala Trp Ile Ser Gly Ala Ser Gln Trp Thr Thr Glu
            100                 105                 110

Gln Arg Lys Ala Leu Ala Asn Asp Ile Thr Arg Pro Gln Leu Trp Ala
        115                 120                 125

Val Ser Ala His Ala Asn Arg Gly Lys Ser Asp Asp Ser Pro Asp Glu
130                 135                 140

Trp Lys Pro Pro Leu Lys Thr Phe Trp Cys Thr Tyr Ala Lys Ser Trp
145                 150                 155                 160

Val Gln Val Lys Ser Phe Tyr Lys Leu Thr Ile Thr Asp Thr Glu Lys
                165                 170                 175

Gly Ala Leu Ala Gly Met Leu Asp Thr Cys
            180                 185

<210> SEQ ID NO 58
<211> LENGTH: 187
<212> TYPE: PRT
<213> ORGANISM: Westerdykella sp. AS85-2

<400> SEQUENCE: 58

Phe Pro Ala Pro Ala Ser Val Leu Glu Ala Arg Ala Pro Pro Asn Ile
1               5                   10                  15

Pro Ser Ala Ser Thr Ala Gln Ser Leu Leu Val Gly Leu Thr Val Gln
            20                  25                  30

Pro Gln Gly Pro Gln Asp Gly Tyr Ser Arg Asp Leu Phe Pro His Trp
        35                  40                  45

Ile Thr Ile Ser Gly Thr Cys Asn Thr Arg Glu Thr Val Leu Lys Arg
50                  55                  60

Asp Gly Ser Asn Val Val Thr Asn Ser Ala Cys Ala Ala Thr Ser Gly
65                  70                  75                  80

Thr Trp Tyr Ser Pro Tyr Asp Gly Ala Thr Trp Thr Ser Ala Ser Asp
                85                  90                  95

```
Val Asp Ile Asp His Leu Val Pro Leu Ser Asn Ala Trp Lys Ser Gly
            100                 105                 110

Ala Ala Ser Trp Thr Thr Ala Lys Arg Gln Gln Phe Ala Asn Asp Leu
        115                 120                 125

Thr Asn Pro Gln Leu Leu Ala Val Thr Asp Arg Val Asn Gln Ala Lys
    130                 135                 140

Gly Asp Lys Gly Pro Glu Ala Trp Lys Pro Ser Leu Ala Ser Tyr His
145                 150                 155                 160

Cys Thr Tyr Ala Lys Met Trp Val Lys Val Lys Ser Lys Asp Val Arg
                165                 170                 175

Leu Thr Gly Asn Trp Thr Lys Asp Asp Gly Trp
                180                 185
```

<210> SEQ ID NO 59
<211> LENGTH: 194
<212> TYPE: PRT
<213> ORGANISM: Humicolopsis cephalosporioides

<400> SEQUENCE: 59

```
Ala Pro Thr Pro Ala Pro Val Glu Leu Glu Arg Arg Thr Pro Pro Asn
1               5                   10                  15

Ile Pro Thr Thr Ala Ser Ala Lys Ser Leu Leu Ala Gly Leu Thr Val
                20                  25                  30

Ala Ala Gln Gly Pro Gln Thr Gly Tyr Ser Arg Asp Leu Phe Pro His
            35                  40                  45

Trp Ile Thr Ile Ser Gly Ser Cys Asn Thr Arg Glu Thr Val Leu Lys
        50                  55                  60

Arg Asp Gly Thr Gly Val Val Thr Asp Ser Ala Cys Ala Ser Thr Ala
65                  70                  75                  80

Gly Ser Trp Tyr Ser Pro Tyr Asp Gly Ala Thr Trp Thr Ala Ala Ser
                85                  90                  95

Asp Val Asp Ile Asp His Met Val Pro Leu Ser Asn Ala Trp Lys Ser
            100                 105                 110

Gly Ala Ala Gln Trp Thr Thr Ala Arg Arg Gln Asp Phe Ala Asn Asp
        115                 120                 125

Leu Thr Asn Pro Gln Leu Phe Ala Val Thr Asp Asn Val Asn Gln Glu
    130                 135                 140

Lys Gly Asp Lys Gly Pro Glu Asp Trp Lys Pro Ser Leu Thr Ser Tyr
145                 150                 155                 160

Tyr Cys Thr Tyr Ala Lys Ala Trp Val Lys Val Lys Ser Val Trp Ala
                165                 170                 175

Leu Thr Ile Thr Ser Ala Glu Lys Ser Ala Leu Thr Thr Met Leu Asn
            180                 185                 190

Thr Cys
```

<210> SEQ ID NO 60
<211> LENGTH: 190
<212> TYPE: PRT
<213> ORGANISM: Neosartorya massa

<400> SEQUENCE: 60

```
Ile Pro Ala Pro Val Ala Leu Pro Thr Pro Gly Ile Pro Ser Ala
1               5                   10                  15

Ala Thr Ala Glu Ser Glu Leu Ala Ala Leu Thr Val Ala Ala Gln Gly
                20                  25                  30

Ser Ser Ser Gly Tyr Ser Arg Asp Leu Phe Pro His Trp Ile Ser Gln
```

```
                35                  40                  45
Gly Gly Ser Cys Asn Thr Arg Glu Val Val Leu Ala Arg Asp Gly Ser
 50                  55                  60

Gly Val Val Lys Asp Ser Asn Cys Tyr Pro Thr Ser Gly Ser Trp Tyr
 65                  70                  75                  80

Ser Pro Tyr Asp Gly Ala Thr Trp Thr Gln Ala Ser Asp Val Asp Ile
                 85                  90                  95

Asp His Val Val Pro Leu Ala Asn Ala Trp Arg Ser Gly Ala Ser Lys
            100                 105                 110

Trp Thr Thr Ser Gln Arg Gln Ala Phe Ala Asn Asp Leu Thr Asn Pro
        115                 120                 125

Gln Leu Met Ala Val Thr Asp Asn Val Asn Gln Ala Lys Gly Asp Asp
    130                 135                 140

Gly Pro Glu Ala Trp Lys Pro Pro Leu Thr Ser Tyr Tyr Cys Thr Tyr
145                 150                 155                 160

Ala Lys Met Trp Val Arg Val Lys Tyr Val Tyr Asp Leu Thr Ile Thr
                165                 170                 175

Ser Ala Glu Lys Ser Ala Leu Val Ser Met Leu Asp Thr Cys
            180                 185                 190

<210> SEQ ID NO 61
<211> LENGTH: 191
<212> TYPE: PRT
<213> ORGANISM: Roussoella intermedia

<400> SEQUENCE: 61

Ala Pro Thr Pro Ala Leu Leu Pro Arg Ala Pro Asn Ile Pro Ser
 1               5                  10                  15

Thr Ala Thr Ala Lys Ser Gln Leu Ala Ala Leu Thr Val Ala Ala Gln
                 20                  25                  30

Gly Pro Gln Asp Gly Tyr Ser Arg Asp Leu Phe Pro His Trp Ile Thr
             35                  40                  45

Gln Ser Gly Ser Cys Asn Thr Arg Glu Val Val Leu Lys Arg Asp Gly
 50                  55                  60

Thr Asn Val Val Gln Asp Ser Ser Cys Ala Ala Thr Ser Gly Thr Trp
 65                  70                  75                  80

Val Ser Pro Phe Asp Gly Ala Thr Trp Thr Ala Ala Ser Asp Val Asp
                 85                  90                  95

Ile Asp His Leu Val Pro Leu Ser Asn Ala Trp Lys Ser Gly Ala Ala
            100                 105                 110

Ser Trp Thr Thr Ala Arg Arg Gln Ser Phe Ala Asn Asp Leu Thr Asn
        115                 120                 125

Pro Gln Leu Leu Ala Val Thr Asp Glu Val Asn Gln Ala Lys Gly Asp
    130                 135                 140

Lys Gly Pro Glu Ala Trp Lys Pro Pro Leu Ala Ser Tyr His Cys Thr
145                 150                 155                 160

Tyr Ala Lys Met Trp Val Lys Val Lys Ser Thr Tyr Ser Leu Thr Ile
                165                 170                 175

Thr Ser Ala Glu Lys Ser Ala Leu Thr Thr Met Leu Asn Thr Cys
            180                 185                 190

<210> SEQ ID NO 62
<211> LENGTH: 191
<212> TYPE: PRT
<213> ORGANISM: Pleosporales
```

<400> SEQUENCE: 62

```
Leu Pro Thr Pro Ser Leu Val Lys Arg Thr Pro Asn Ile Pro Ser
1               5                   10                  15

Thr Thr Ser Ala Lys Ser Leu Leu Ala Gly Leu Thr Val Ala Ala Gln
            20                  25                  30

Gly Pro Gln Asp Gly Tyr Ser Arg Asp Leu Phe Pro His Trp Ile Thr
        35                  40                  45

Ile Ser Gly Thr Cys Asn Thr Arg Glu Thr Val Leu Lys Arg Asp Gly
    50                  55                  60

Thr Asn Val Val Thr Asp Ser Ala Cys Ala Ser Thr Ser Gly Ser Trp
65                  70                  75                  80

Tyr Ser Thr Tyr Asp Gly Ala Thr Trp Thr Ala Ala Ser Asp Val Asp
                85                  90                  95

Ile Asp His Val Val Pro Leu Ser Asn Ala Trp Lys Ser Gly Ala Ala
            100                 105                 110

Ser Trp Thr Thr Ala Arg Arg Gln Ser Phe Ala Asn Asp Leu Thr Asn
        115                 120                 125

Pro Gln Leu Ile Ala Val Thr Asp Ser Val Asn Gln Ser Lys Gly Asp
    130                 135                 140

Lys Gly Pro Glu Ser Trp Lys Pro Pro Leu Thr Ser Tyr His Cys Thr
145                 150                 155                 160

Tyr Ala Lys Met Trp Val Lys Val Lys Asp Val Tyr Ser Leu Thr Val
                165                 170                 175

Thr Ser Ala Glu Lys Ser Ala Leu Thr Thr Met Leu Asn Thr Cys
            180                 185                 190
```

<210> SEQ ID NO 63
<211> LENGTH: 192
<212> TYPE: PRT
<213> ORGANISM: Phaeosphaeria sp.

<400> SEQUENCE: 63

```
Leu Pro Ala Pro Ile His Leu Thr Ala Arg Ala Pro Asn Ile Pro
1               5                   10                  15

Ser Ala Ser Glu Ala Arg Thr Gln Leu Ala Gly Leu Thr Val Ala Ala
            20                  25                  30

Gln Gly Pro Gln Asp Gly Tyr Ser Arg Asp Leu Phe Pro His Trp Ile
        35                  40                  45

Thr Gln Ser Gly Thr Cys Asn Thr Arg Glu Thr Val Leu Lys Arg Asp
    50                  55                  60

Gly Thr Asn Val Val Thr Asn Ser Ala Cys Ala Ser Thr Ser Gly Ser
65                  70                  75                  80

Trp Phe Ser Pro Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
            100                 105                 110

Ala Ser Trp Thr Thr Ala Arg Arg Gln Ala Phe Ala Asn Asp Leu Thr
        115                 120                 125

Asn Pro Gln Leu Leu Ala Val Thr Asp Asn Val Asn Gln Ala Lys Gly
    130                 135                 140

Asp Lys Gly Pro Glu Asp Trp Lys Pro Pro Leu Thr Ser Tyr Tyr Cys
145                 150                 155                 160

Thr Tyr Ala Arg Met Trp Val Lys Val Lys Ser Val Tyr Ala Leu Thr
                165                 170                 175
```

Val Thr Ser Ala Glu Lys Ser Ala Leu Thr Ser Met Leu Gly Thr Cys
        180                 185                 190

<210> SEQ ID NO 64
<211> LENGTH: 189
<212> TYPE: PRT
<213> ORGANISM: Didymosphaeria futilis

<400> SEQUENCE: 64

Leu Pro Thr Pro Asn Thr Leu Glu Ala Arg Ala Pro Pro Asn Ile Pro
1               5                   10                  15

Ser Thr Ser Ala Ala Gln Ser Gln Leu Ser Ala Leu Thr Val Ala Ala
            20                  25                  30

Gln Gly Pro Gln Thr Gly Tyr Ser Arg Asp Leu Phe Pro His Trp Ile
        35                  40                  45

Thr Gln Ser Gly Thr Cys Asn Thr Arg Glu Thr Val Leu Lys Arg Asp
    50                  55                  60

Gly Thr Asn Val Leu Thr Asp Ser Ala Cys Ala Ser Thr Ser Gly Ser
65                  70                  75                  80

Trp Lys Ser Pro Tyr Asp Gly Ala Thr Trp Thr Ala Ala Ser Asp Val
                85                  90                  95

Asp Ile Asp His Val Val Pro Leu Ser Asn Ala Trp Lys Ser Gly Ala
            100                 105                 110

Ala Ser Trp Thr Thr Ala Arg Arg Gln Ser Phe Ala Asn Asp Leu Thr
        115                 120                 125

Asn Pro Gln Leu Ile Ala Val Thr Asp Asn Val Asn Gln Ala Lys Gly
    130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ser Leu Thr
                165                 170                 175

Ile Thr Ser Ala Glu Lys Ser Ala Leu Thr Met Leu Ala
            180                 185

<210> SEQ ID NO 65
<211> LENGTH: 109
<212> TYPE: PRT
<213> ORGANISM: Bacillus licheniformis

<400> SEQUENCE: 65

Ala Arg Tyr Asp Asp Ile Leu Tyr Phe Pro Ala Ser Arg Tyr Pro Glu
1               5                   10                  15

Thr Gly Ala His Ile Ser Asp Ala Ile Lys Ala Gly His Ser Asp Val
            20                  25                  30

Cys Thr Ile Glu Arg Ser Gly Ala Asp Lys Arg Gln Glu Ser Leu
        35                  40                  45

Lys Gly Ile Pro Thr Lys Pro Gly Phe Asp Arg Asp Glu Trp Pro Met
    50                  55                  60

Ala Met Cys Glu Glu Gly Gly Lys Gly Ala Ser Val Arg Tyr Val Ser
65                  70                  75                  80

Ser Ser Asp Asn Arg Gly Ala Gly Ser Trp Val Gly Asn Arg Leu Ser
                85                  90                  95

Gly Phe Ala Asp Gly Thr Arg Ile Leu Phe Ile Val Gln
            100                 105

<210> SEQ ID NO 66
<211> LENGTH: 110

<212> TYPE: PRT
<213> ORGANISM: Bacillus subtilis

<400> SEQUENCE: 66

```
Ala Ser Ser Tyr Asp Lys Val Leu Tyr Phe Pro Leu Ser Arg Tyr Pro
1               5                   10                  15
Glu Thr Gly Ser His Ile Arg Asp Ala Ile Ala Glu Gly His Pro Asp
            20                  25                  30
Ile Cys Thr Ile Asp Arg Asp Gly Ala Asp Lys Arg Arg Glu Glu Ser
        35                  40                  45
Leu Lys Gly Ile Pro Thr Lys Pro Gly Tyr Asp Arg Asp Glu Trp Pro
50                  55                  60
Met Ala Val Cys Glu Glu Gly Gly Ala Gly Asp Val Arg Tyr Val
65                  70                  75                  80
Thr Pro Ser Asp Asn Arg Gly Ala Gly Ser Trp Val Gly Asn Gln Met
                85                  90                  95
Ser Ser Tyr Pro Asp Gly Thr Arg Val Leu Phe Ile Val Gln
            100                 105                 110
```

<210> SEQ ID NO 67
<211> LENGTH: 221
<212> TYPE: PRT
<213> ORGANISM: Aspergillus oryzae

<400> SEQUENCE: 67

```
Val Pro Val Asn Pro Glu Pro Asp Ala Thr Ser Val Glu Asn Val Ala
1               5                   10                  15
Leu Lys Thr Gly Ser Gly Asp Ser Gln Ser Asp Pro Ile Lys Ala Asp
            20                  25                  30
Leu Glu Val Lys Gly Gln Ser Ala Leu Pro Phe Asp Val Asp Cys Trp
        35                  40                  45
Ala Ile Leu Cys Lys Gly Ala Pro Asn Val Leu Gln Arg Val Asn Glu
50                  55                  60
Lys Thr Lys Asn Ser Asn Arg Asp Arg Ser Gly Ala Asn Lys Gly Pro
65                  70                  75                  80
Phe Lys Asp Pro Gln Lys Trp Gly Ile Lys Ala Leu Pro Pro Lys Asn
                85                  90                  95
Pro Ser Trp Ser Ala Gln Asp Phe Lys Ser Pro Glu Glu Tyr Ala Phe
            100                 105                 110
Ala Ser Ser Leu Gln Gly Gly Thr Asn Ala Ile Leu Ala Pro Val Asn
            115                 120                 125
Leu Ala Ser Gln Asn Ser Gln Gly Val Leu Asn Gly Phe Tyr Ser
130                 135                 140
Ala Asn Lys Val Ala Gln Phe Asp Pro Ser Lys Pro Gln Gln Thr Lys
145                 150                 155                 160
Gly Thr Trp Phe Gln Ile Thr Lys Phe Thr Gly Ala Ala Gly Pro Tyr
                165                 170                 175
Cys Lys Ala Leu Gly Ser Asn Asp Lys Ser Val Cys Asp Lys Asn Lys
            180                 185                 190
Asn Ile Ala Gly Asp Trp Gly Phe Asp Pro Ala Lys Trp Ala Tyr Gln
        195                 200                 205
Tyr Asp Glu Lys Asn Asn Lys Phe Asn Tyr Val Gly Lys
    210                 215                 220
```

<210> SEQ ID NO 68
<211> LENGTH: 188

```
<212> TYPE: PRT
<213> ORGANISM: Trichoderma harzianum

<400> SEQUENCE: 68

Ala Pro Ala Pro Met Pro Thr Pro Pro Gly Ile Pro Thr Glu Ser Ser
1               5                   10                  15

Ala Arg Thr Gln Leu Ala Gly Leu Thr Val Ala Val Ala Gly Ser Gly
            20                  25                  30

Thr Gly Tyr Ser Arg Asp Leu Phe Pro Thr Trp Asp Ala Ile Ser Gly
        35                  40                  45

Asn Cys Asn Ala Arg Glu Tyr Val Leu Lys Arg Asp Gly Glu Gly Val
    50                  55                  60

Gln Val Asn Asn Ala Cys Glu Ser Gln Ser Gly Thr Trp Ile Ser Pro
65                  70                  75                  80

Tyr Asp Asn Ala Ser Phe Thr Asn Ala Ser Ser Leu Asp Ile Asp His
                85                  90                  95

Met Val Pro Leu Lys Asn Ala Trp Ile Ser Gly Ala Ser Ser Trp Thr
            100                 105                 110

Thr Ala Gln Arg Glu Ala Leu Ala Asn Asp Val Ser Arg Pro Gln Leu
        115                 120                 125

Trp Ala Val Ser Ala Ser Ala Asn Arg Ser Lys Gly Asp Arg Ser Pro
130                 135                 140

Asp Gln Trp Lys Pro Pro Leu Thr Ser Phe Tyr Cys Thr Tyr Ala Lys
145                 150                 155                 160

Ser Trp Ile Asp Val Lys Ser Phe Tyr Lys Leu Thr Ile Thr Ser Ala
                165                 170                 175

Glu Lys Thr Ala Leu Ser Ser Met Leu Asp Thr Cys
            180                 185

<210> SEQ ID NO 69
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = Thr (T) or Asp (D) or Ser (S)
<220> FEATURE:
<221> NAME/KEY: MISC_FEATURE
<222> LOCATION: (2)..(2)
<223> OTHER INFORMATION: Xaa = Gly (G) or Asn (N)

<400> SEQUENCE: 69

Xaa Xaa Pro Gln Leu
1               5

<210> SEQ ID NO 70
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = F (phe) or L (Leu) or Y (Tyr) or I (Ile)
<220> FEATURE:
<221> NAME/KEY: MISC_FEATURE
<222> LOCATION: (3)..(3)
<223> OTHER INFORMATION: Xaa = N (Asn) or R (Arg)
<220> FEATURE:
<221> NAME/KEY: MISC_FEATURE
```

```
<222> LOCATION: (5)..(5)
<223> OTHER INFORMATION: Xaa = L (Leu) or I (Ile) or P (Phe) or V (Val)

<400> SEQUENCE: 70

Xaa Ala Xaa Asp Xaa
1               5

<210> SEQ ID NO 71
<211> LENGTH: 4
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa= Asp (D) or Asn (N)
<220> FEATURE:
<221> NAME/KEY: MISC_FEATURE
<222> LOCATION: (4)..(4)
<223> OTHER INFORMATION: Xaa= Ala (A) or Arg (R)

<400> SEQUENCE: 71

Cys Xaa Thr Xaa
1

<210> SEQ ID NO 72
<211> LENGTH: 4
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = Asp (D) or Gln (Q)
<220> FEATURE:
<221> NAME/KEY: MISC_FEATURE
<222> LOCATION: (2)..(2)
<223> OTHER INFORMATION: Xaa = Ile (I) or Val (V)

<400> SEQUENCE: 72

Xaa Xaa Asp His
1

<210> SEQ ID NO 73
<211> LENGTH: 7
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = Asp (D) or Met (M) or Leu (L)
<220> FEATURE:
<221> NAME/KEY: MISC_FEATURE
<222> LOCATION: (2)..(2)
<223> OTHER INFORMATION: Xaa = Ser (S) or Thr (T)
<220> FEATURE:
<221> NAME/KEY: MISC_FEATURE
<222> LOCATION: (7)..(7)
<223> OTHER INFORMATION: Xaa = Asp (D) or Asn (N)

<400> SEQUENCE: 73

Xaa Xaa Gly Tyr Ser Arg Xaa
1               5

<210> SEQ ID NO 74
<211> LENGTH: 8
<212> TYPE: PRT
```

```
<213> ORGANISM: Artificial
<220> FEATURE:
<223> OTHER INFORMATION: Motif
<220> FEATURE:
<221> NAME/KEY: MISC_FEATURE
<222> LOCATION: (3)..(3)
<223> OTHER INFORMATION: Xaa = any amino acid

<400> SEQUENCE: 74

Ala Ser Xaa Asn Arg Ser Lys Gly
1               5

<210> SEQ ID NO 75
<211> LENGTH: 8
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa = Val (V) or Ile (I)
<220> FEATURE:
<221> NAME/KEY: MISC_FEATURE
<222> LOCATION: (4)..(4)
<223> OTHER INFORMATION: Xaa = Ser (S) or Ala (A)

<400> SEQUENCE: 75

Xaa Pro Leu Xaa Asn Ala Trp Lys
1               5

<210> SEQ ID NO 76
<211> LENGTH: 4
<212> TYPE: PRT
<213> ORGANISM: Artificial
<220> FEATURE:
<223> OTHER INFORMATION: Motif

<400> SEQUENCE: 76

Asn Pro Gln Leu
1

<210> SEQ ID NO 77
<211> LENGTH: 4
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa = Gln (Q) or Glu(E)
<220> FEATURE:
<221> NAME/KEY: MISC_FEATURE
<222> LOCATION: (4)..(4)
<223> OTHER INFORMATION: Xaa = Trp (W) or Tyr (Y)

<400> SEQUENCE: 77

Pro Xaa Leu Xaa
1

<210> SEQ ID NO 78
<211> LENGTH: 4
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa=Lys (K) or His (H) or Glu (E)
```

<400> SEQUENCE: 78

Xaa Asn Ala Trp
1

<210> SEQ ID NO 79
<211> LENGTH: 269
<212> TYPE: PRT
<213> ORGANISM: Bacillus lentus

<400> SEQUENCE: 79

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 80
<211> LENGTH: 275
<212> TYPE: PRT
<213> ORGANISM: Bacillus amyloliquefaciens

<400> SEQUENCE: 80

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

```
Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
 50                  55                  60

Gly Thr His Val Ala Gly Thr Val Ala Ala Leu Asn Asn Ser Ile Gly
 65                  70                  75                  80

Val Leu Gly Val Ala Pro Ser Ala Ser Leu Tyr Ala Val Lys Val Leu
                 85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
            195                 200                 205

Leu Pro Gly Asn Lys Tyr Gly Ala Tyr Asn Gly Thr Ser Met Ala Ser
            210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
                260                 265                 270

Ala Ala Gln
        275

<210> SEQ ID NO 81
<211> LENGTH: 311
<212> TYPE: PRT
<213> ORGANISM: Bacillus subtilis

<400> SEQUENCE: 81

Ala Val Pro Ser Thr Gln Thr Pro Trp Gly Ile Lys Ser Ile Tyr Asn
1               5                  10                  15

Asp Gln Ser Ile Thr Lys Thr Gly Gly Ser Gly Ile Lys Val Ala
            20                  25                  30

Val Leu Asp Thr Gly Val Tyr Thr Ser His Leu Asp Leu Ala Gly Ser
            35                  40                  45

Ala Glu Gln Cys Lys Asp Phe Thr Gln Ser Asn Pro Leu Val Asp Gly
        50                  55                  60

Ser Cys Thr Asp Arg Gln Gly His Gly Thr His Val Ala Gly Thr Val
65                  70                  75                  80

Leu Ala His Gly Gly Ser Asn Gly Gln Gly Val Tyr Gly Val Ala Pro
                85                  90                  95

Gln Ala Lys Leu Trp Ala Tyr Lys Val Leu Gly Asp Asn Gly Ser Gly
            100                 105                 110

Tyr Ser Asp Asp Ile Ala Ala Ile Arg His Val Ala Asp Glu Ala
            115                 120                 125
```

```
Ser Arg Thr Gly Ser Lys Val Val Ile Asn Met Ser Leu Gly Ser Ser
    130                 135                 140
Ala Lys Asp Ser Leu Ile Ala Ser Ala Val Asp Tyr Ala Tyr Gly Lys
145                 150                 155                 160
Gly Val Leu Ile Val Ala Ala Gly Asn Ser Gly Ser Gly Ser Asn
                165                 170                 175
Thr Ile Gly Phe Pro Gly Gly Leu Val Asn Ala Val Ala Val Ala Ala
            180                 185                 190
Leu Glu Asn Val Gln Gln Asn Gly Thr Tyr Arg Val Ala Asp Phe Ser
                195                 200                 205
Ser Arg Gly Asn Pro Ala Thr Ala Gly Asp Tyr Ile Ile Gln Glu Arg
    210                 215                 220
Asp Ile Glu Val Ser Ala Pro Gly Ala Ser Val Glu Ser Thr Trp Tyr
225                 230                 235                 240
Thr Gly Gly Tyr Asn Thr Ile Ser Gly Thr Ser Met Ala Thr Pro His
                245                 250                 255
Val Ala Gly Leu Ala Ala Lys Ile Trp Ser Ala Asn Thr Ser Leu Ser
            260                 265                 270
His Ser Gln Leu Arg Thr Glu Leu Gln Asn Arg Ala Lys Val Tyr Asp
    275                 280                 285
Ile Lys Gly Gly Ile Gly Ala Gly Thr Gly Asp Asp Tyr Ala Ser Gly
290                 295                 300
Phe Gly Tyr Pro Arg Val Lys
305                 310

<210> SEQ ID NO 82
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa= F (Phe) or Y (Tyr)
<220> FEATURE:
<221> NAME/KEY: MISC_FEATURE
<222> LOCATION: (4)..(4)
<223> OTHER INFORMATION: Xaa= L(Leu) or Y (Tyr) or F (Phe)

<400> SEQUENCE: 82

Gly Xaa Xaa Xaa Asp
1               5

<210> SEQ ID NO 83
<211> LENGTH: 7
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = S (Ser) or E (Glu) or T (Thr)
<220> FEATURE:
<221> NAME/KEY: MISC_FEATURE
```

```
<222> LOCATION: (5)..(5)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = E (Glu) or A (Ala) or S (Ser)

<400> SEQUENCE: 83

Ala Tyr Xaa Xaa Xaa Xaa Xaa
1               5

<210> SEQ ID NO 84
<211> LENGTH: 904
<212> TYPE: PRT
<213> ORGANISM: Pseudomonas sp-62208

<400> SEQUENCE: 84

Ala Ala Leu Thr Pro Pro Ser Ser Val Thr Phe Trp Tyr Ala Glu Glu
1               5                   10                  15

Pro Pro Leu Ala Glu Leu Ala Gln Phe Asp Trp Ala Val Val Glu Pro
            20                  25                  30

Gly His Met Thr Ala Gly Asp Val Thr Thr Leu Arg Lys Leu Gly Ser
        35                  40                  45

Glu Pro Phe Ala Tyr Leu Ser Val Gly Glu Phe Asp Gly Asn Lys Ala
    50                  55                  60

Asp Ile Thr Lys Ala Gly Leu Thr Ala Ala Val Ser Pro Val Arg Asn
65                  70                  75                  80

Asp Ser Trp Asn Ser Gln Val Met Asp Leu Thr Thr Gln Ala Trp Arg
                85                  90                  95

Glu Tyr Leu Leu Gly Arg Ala Lys Gln Leu Gln Ala Gln Gly Tyr Ala
            100                 105                 110

Gly Leu Phe Leu Asp Thr Leu Asp Ser Phe Gln Leu Leu Pro Glu Ala
        115                 120                 125

Ser Arg Glu Ala Gln Arg Lys Ala Leu Ala Ser Leu Leu Arg Glu Leu
    130                 135                 140

His Lys Arg Gln Pro Gly Leu Lys Leu Phe Phe Asn Arg Gly Phe Glu
145                 150                 155                 160

Val Leu Pro Glu Leu Asp Gly Val Ala Ser Ala Val Ala Phe Glu Ser
                165                 170                 175

Leu Tyr Ala Gly Trp Asp Ala Ala Lys Arg Tyr Arg Pro Val Pro
            180                 185                 190

Glu Ala Asp Arg Gln Trp Leu Leu Gly Glu Leu Ala Pro Leu Arg Ala
        195                 200                 205

Lys Gly Ile Pro Leu Val Ala Ile Asp Tyr Leu Pro Pro Glu Arg Arg
    210                 215                 220

Glu Glu Ala Arg Lys Leu Ala Lys Arg Leu Arg Asp Glu Gly Tyr Ile
225                 230                 235                 240

Pro Phe Ile Ser Thr Pro Glu Leu Asn Ser Met Gly Ile Ser Asn Val
                245                 250                 255

Glu Val Gln Pro Arg Arg Val Ala Leu Val Tyr Asp Pro Arg Glu Gly
            260                 265                 270

Asp Leu Thr Val Asn Ala Gly His Thr Met Leu Gly Gly Leu Leu Glu
        275                 280                 285

Tyr Leu Gly Tyr Arg Val Asp Tyr Leu Ala Val Asp Ser Leu Pro Glu
```

```
                290                 295                 300
His Arg Phe Ser Gly Leu Tyr Ala Gly Ile Ile Thr Trp Met Ala Ser
305                 310                 315                 320

Gly Pro Pro Gln Asp Gly Ala Thr Phe Asn Arg Trp Leu Gly Lys Arg
                325                 330                 335

Leu Asp Glu Gln Val Pro Val Val Phe Phe Ala Gly Leu Pro Thr Glu
                340                 345                 350

Asp Lys Val Leu Leu Lys Arg Leu Gly Leu Asn Leu Met Ala Pro Ala
                355                 360                 365

Gly Thr Gln Pro Leu Thr Ile Ser Tyr Gln Asp Lys Ala Leu Ile Gly
                370                 375                 380

Ala Phe Glu Ala Pro Val Gln Pro Arg Ser Arg Glu Leu Thr Ala Val
385                 390                 395                 400

Ser Leu Leu Pro Gln Gly Pro Lys Ala Ala Leu Leu Leu Thr Gly Lys
                405                 410                 415

Asp Gly Gln Thr Phe Ala Pro Val Ala Thr Ala Lys Trp Gly Gly Leu
                420                 425                 430

Ala Leu Ala Pro Tyr Val Leu Glu Thr Asn Asn Glu Arg Ser Arg Trp
                435                 440                 445

Ile Leu Asp Pro Phe Ala Phe Leu Gln Ala Ser Leu Gln Leu Pro Ala
                450                 455                 460

Gln Pro Arg Pro Asp Thr Thr Thr Glu Asn Gly Arg Arg Ile Ala Thr
465                 470                 475                 480

Val His Ile Asp Gly Asp Gly Phe Pro Ser Arg Ala Glu Val Arg Gly
                485                 490                 495

Ser Pro Tyr Ala Gly Lys Gln Val Leu Asn Asp Phe Ile Gln Pro Asn
                500                 505                 510

Pro Phe Leu Thr Ser Val Ser Ile Ile Glu Gly Glu Ile Ser Pro Arg
                515                 520                 525

Gly Met Tyr Pro His Leu Ala Arg Glu Leu Glu Pro Ile Ala Arg Glu
                530                 535                 540

Leu Phe Ala Asn Pro Lys Val Glu Val Ala Thr His Thr Phe Ser His
545                 550                 555                 560

Pro Phe Tyr Met Gln Pro Glu Leu Ala Glu Lys Asp Glu Asp Phe Ser
                565                 570                 575

Ala Glu Tyr Gly Leu Lys Met Ala Ile Pro Gly Tyr Asp Lys Ile Asp
                580                 585                 590

Phe Lys Arg Glu Ile Phe Gly Ser Arg Asp Tyr Ile Asn Gln Gln Leu
                595                 600                 605

Thr Thr Pro Glu Lys Pro Val Lys Met Val Phe Trp Pro Gly Asp Ala
610                 615                 620

Leu Pro Ser Ala Ala Thr Ile Lys Leu Ala Tyr Asp Ala Gly Leu Lys
625                 630                 635                 640

Asn Val Asn Gly Ala Ser Thr Met Leu Thr Lys Ala Arg Pro Ser Leu
                645                 650                 655

Thr Gly Leu Asn Pro Leu Leu Arg Pro Thr Glu Gly Gly Leu Gln Tyr
                660                 665                 670

Tyr Ala Pro Val Ile Asn Glu Asn Val Tyr Thr Asn Leu Trp Lys Gly
                675                 680                 685

Pro Tyr Tyr Gly Phe Arg Asp Val Ile Asp Thr Tyr Glu Leu Thr Asp
                690                 695                 700

Ser Pro Arg Arg Leu Arg Gly Ile His Leu Tyr Tyr His Phe Tyr Ser
705                 710                 715                 720
```

```
Ala Thr Lys Gln Ala Ser Ile Lys Ala Met Gly Glu Ile Tyr Gly Tyr
                725                 730                 735

Met Arg Glu Gln His Pro Met Ser Leu Trp Met Ser Asp Tyr Leu Asp
            740                 745                 750

Arg Leu His Gly Leu Tyr Gln Ala Ser Leu Ala Arg Thr Ala Asp Gly
        755                 760                 765

Ala Trp Gln Ile Arg Gly Met Asp Ala Leu Arg Thr Val Arg Leu Asp
770                 775                 780

Pro Gln Met Gly Trp Pro Asp Leu Leu Arg Ser Gln Gly Ile Ala Gly
785                 790                 795                 800

Val Arg Asp Leu Pro Gln Gly Arg Tyr Val His Leu Ser Ser Asp Arg
                805                 810                 815

Ala Leu Leu Val Leu Arg Pro Asp Arg Asp Asp Arg Pro Ala Leu Glu
            820                 825                 830

Glu Ala Asn Val Pro Leu Thr Asp Trp Arg Tyr Leu Asp Asp Arg Arg
        835                 840                 845

Val Ser Phe Ala Phe Ala Gly Gln Phe Asp Val Thr Phe Ser Val Arg
850                 855                 860

Ser Ala Ser Ala Cys Arg Val Glu Val Asp Gly Gln Arg Phe Ala Gly
865                 870                 875                 880

Lys Ser Ser Ala Gly Leu Trp Thr Phe Gln Leu Pro Met Lys Gln Val
                885                 890                 895

Ser Asn Gly Gln Leu Leu Cys Asn
                900

<210> SEQ ID NO 85
<211> LENGTH: 281
<212> TYPE: PRT
<213> ORGANISM: Environmental bacterial community A

<400> SEQUENCE: 85

Thr Pro Gly Met Gly Lys Gly Ile Leu Ser Asn Ala Lys Ser Trp Val
1               5                   10                  15

Tyr Gln Leu Gln His Ile Asp Leu Pro Thr Leu Gly Thr Thr Thr Ala
            20                  25                  30

Asp Leu Val Val Ile Asp Ala Ser Gln Asp Gly Ser Val Glu Gly Ser
        35                  40                  45

Phe Thr Pro Ala Asp Ile Ala Ala Leu Lys Thr Lys Pro Asp Gly Ser
50                  55                  60

Gln Arg Val Val Leu Ala Tyr Phe Ser Ile Gly Glu Ala Glu Asp Tyr
65                  70                  75                  80

Arg Phe Tyr Trp Asp Asp Glu Trp Tyr Asp Gln Ala Pro Asp Trp Leu
                85                  90                  95

His Glu Glu Asn Ser Asp Trp Ala Gly Asn Tyr Pro Val Lys Phe Trp
            100                 105                 110

His Pro Asp Trp Gln Ala Ile Leu Phe Gly Ser Pro Cys Tyr Leu
        115                 120                 125

Asp Arg Ile Ile Ala Ala Gly Phe Asp Gly Val Tyr Leu Asp Arg Val
130                 135                 140

Asp Ala Phe Glu Ile Asp Asp Pro Ala Leu Thr Arg Pro Gln Arg Ala
145                 150                 155                 160

Ala His Met Ile Ala Leu Val Arg Ser Leu Ala Ala Tyr Ala Arg Ala
                165                 170                 175

Arg Thr Pro Ser Phe Val Val Val Ala Gln Asn Gly Glu Glu Leu Leu
```

```
            180                 185                 190
Ala Asp Gly Ser Tyr Arg His Thr Val Asp Gly Val Gly Lys Glu Asp
        195                 200                 205

Leu Leu Tyr Gly Leu Glu Ser Asp Gly Lys Arg Asn Ala Asn Gly Asp
    210                 215                 220

Ile Arg Val Ser Leu Asp Tyr Leu Arg Arg Leu Ala Glu Ala Gly Lys
225                 230                 235                 240

Pro Val Phe Leu Val Glu Tyr Leu Thr Glu Pro Gln Thr Ile Ala Gln
                245                 250                 255

Ala His Ala Asp Ala Glu Thr Leu Gly Met Pro Ile Phe Ile Thr Asp
            260                 265                 270

Arg Asp Leu Asp Asn Ala Tyr Ser Arg
            275                 280

<210> SEQ ID NO 86
<211> LENGTH: 458
<212> TYPE: PRT
<213> ORGANISM: Thermus rehai

<400> SEQUENCE: 86

Gln Val Asp Pro Ser His Val Ala Gln Ala Val Arg Arg Thr Ile Gln
1               5                   10                  15

Ile Gly Gly Gly Leu Glu Gln Trp Ser Gly Leu Pro Gln Tyr Pro Val
                20                  25                  30

Val Leu Ser Asn Thr Phe Pro Ala Lys Pro Val Thr His Gly Gly Tyr
            35                  40                  45

Phe Ser Val Ala Trp Asp Asp Arg His Leu Tyr Ile Leu Gly Val Phe
    50                  55                  60

Glu Gln Lys Ala Glu Thr Val Lys Ala Ala Leu Pro Glu Glu His Pro
65                  70                  75                  80

Glu Trp Trp Asn Asp Asp Thr Met Glu Val Phe Leu Lys Pro Asp Pro
                85                  90                  95

Lys Gly Val Glu Val Ile His Leu Ala Ala Asn Pro Lys Gly Thr Arg
                100                 105                 110

Phe Lys Ala Tyr Thr Phe Thr Thr Asp Tyr Ala Thr Ser Gly Arg Val
            115                 120                 125

Glu Ala Ser Arg Trp Val Leu Glu Trp Ala Ile Pro Phe Ala Ser Leu
    130                 135                 140

Lys Thr Ser Pro Pro Glu Pro Gly Ala Ile Trp Ala Met Lys Val Gly
145                 150                 155                 160

Arg Glu His Gln Ala Ala Gln Glu Tyr Pro Leu Trp Pro Met Gly Gly
                165                 170                 175

Asp Tyr His Ala Pro Thr Asn Phe Gly Tyr Leu Val Phe Val Glu Lys
            180                 185                 190

Leu Glu Asp Pro Gln Ala Leu Ala Gln Arg Val Gln Ala Leu Leu Gly
        195                 200                 205

Val Glu Pro Pro Ile Arg Ser Arg Leu Gln Asp Ile Ala Thr Tyr Ala
    210                 215                 220

Val Tyr Tyr Gly Lys Asp Pro Gln Glu Ala Lys Leu Val Asp Phe
225                 230                 235                 240

Asp Leu Ala Ile Val Gln Pro Asn Leu Pro Lys Glu Ser Leu Ala Leu
                245                 250                 255

Leu Lys Ala Asn Gly Val Arg Val Ala Tyr Leu Ser Ile Gly Glu
            260                 265                 270
```

```
Ala Glu Pro Glu Arg Asp Tyr Gly Gln Pro Leu Pro Lys Glu Trp Leu
            275                 280                 285

Leu Gly Gln Asn Pro Asn Trp Gly Ser Tyr Phe Val Asp Ala Asn Gln
        290                 295                 300

Lys Gly Trp Gln Glu Leu Val Leu Arg Leu Ala Glu Gly Tyr Leu Lys
305                 310                 315                 320

Ala Gly Phe Asp Gly Leu Phe Leu Asp Thr Leu Asp Thr Ala Asp Leu
                325                 330                 335

Tyr Pro Gln Val Ala Pro Gly Leu Val Ala Ile Val Gln Ala Leu Arg
            340                 345                 350

Glu Arg Phe Pro Glu Ala Ile Leu Val Gln Asn Arg Gly Phe Arg Leu
        355                 360                 365

Leu Pro Lys Thr Ala Glu Leu Val Asp Ala Val Met Tyr Glu Asn Leu
370                 375                 380

Ser Ala Met Tyr Asn Phe Gln Glu Lys Arg Tyr Val Ala Val Asp Gly
385                 390                 395                 400

Asp Pro Thr Pro Val Leu Pro Tyr Ala Lys Arg Gly Leu Val Val Leu
                405                 410                 415

Ala Leu Asp Tyr Ala Leu Pro Glu Asp Val Asp Leu Val Arg Arg Ala
            420                 425                 430

Tyr Val Arg Ala Arg Glu Leu Gly Phe Val Pro Tyr Val Ser Val Ile
        435                 440                 445

Arg Leu Asp Arg Val Phe Leu His Asn Pro
    450                 455

<210> SEQ ID NO 87
<211> LENGTH: 468
<212> TYPE: PRT
<213> ORGANISM: Environmental bacterial community LE

<400> SEQUENCE: 87

Asp Asp Phe Asp Thr Gly Gln Asp Ala Ile Leu Pro Asp Ala Arg Thr
1               5                   10                  15

Leu Pro Cys Thr Thr Leu Gln Phe Glu Arg Gly Ala Leu Pro Ser Gly
            20                  25                  30

Gln Ser Val Gln Gly Leu Asn Thr Gln Thr Leu Ser Gly Thr Gln Asp
        35                  40                  45

Arg Trp Ala Glu Tyr Val Glu Phe Ala Pro Asn Ser Ser Ala Thr Cys
    50                  55                  60

Thr Tyr Pro Leu Pro Thr Gly Val Ser Ala Asp Ser Val Val Ala Ala
65                  70                  75                  80

Glu Val Gly Val Asn Tyr Arg Gly Pro Thr Lys Ala Gln Met Arg Trp
                85                  90                  95

Val Ile Glu Ala Trp Asp Tyr Ser Thr Asn Ser Trp Ala Leu Val Gly
            100                 105                 110

Asp Asn Thr Phe Ala Gln Ser Trp Arg Trp Thr Ala Thr Ser Leu Ala
        115                 120                 125

Leu Pro Thr Pro Ala Arg Phe Leu Ser Gly Gly Pro Val Lys Leu Arg
    130                 135                 140

Tyr Arg Thr Asp Ser Thr Ala Asp Ala Ser Leu Leu Asp Leu Leu Val
145                 150                 155                 160

Val Arg Val Gln Val Ala Ala Ser Asp Ala Gly Thr Pro Thr Asp Ala
                165                 170                 175

Gly Thr Pro Thr Asp Ala Gly Thr Pro Thr Asp Ala Gly Thr Pro Thr
            180                 185                 190
```

```
Asp Ala Gly Thr Gln Val Pro Trp Ser Asn Val Lys Ser Phe Thr Tyr
            195                 200                 205

Gln Leu Thr Asn Tyr Pro Gln Gly Lys Leu Asp Ala Ile Ala Ala Ser
            210                 215                 220

Lys Phe Asp Leu Ala Ile Val Glu Leu Val Arg Asp Gly Ser Ser Gly
225                 230                 235                 240

Tyr Phe Thr Ala Ala Glu Ile Ser Ala Leu Lys Ala Arg Gly Lys Gln
                245                 250                 255

Val Leu Ala Tyr Phe Glu Ile Gly Ala Ile Glu Glu Tyr Arg Pro Glu
            260                 265                 270

Trp Ser Gln Val Pro Ala Asp Leu Lys Leu Gly Pro Val Ser Gly Trp
            275                 280                 285

Pro Asp Glu Gln Tyr Val Lys Tyr Trp Asp Glu Arg Trp Pro Ile
            290                 295                 300

Val Gln Gly Arg Ile Asp Arg Ala Leu Ala Ala Gly Phe Asn Gly Cys
305                 310                 315                 320

Tyr Leu Asp Met Val Val Thr Tyr Glu Glu Ile Pro Ala Asn Ser Ala
                325                 330                 335

Gly Thr Asn Arg Ala Asp Leu Ala Arg Lys Met Val Ala Leu Ile Ala
            340                 345                 350

Arg Ile Asn Thr Tyr Ala Lys Ala Arg Asn Pro Asp Phe Lys Val Val
            355                 360                 365

Pro Gln Asn Ser Pro Glu Leu Val Asp Pro Ala Tyr Leu Pro Ala
            370                 375                 380

Ile Asp Gly Leu Gly Met Glu Asp Met Tyr Trp Ser Asp Val Ala
385                 390                 395                 400

Cys Asp Glu Gly Trp Cys Glu Glu Asn Arg Thr Asn Ala Ala Arg Val
                405                 410                 415

Arg Ala Ala Gly Lys Leu Val Leu Ser Thr Asp Tyr Ala Thr Gln Ser
            420                 425                 430

Ala His Val Ala Asp Ala Tyr Thr Arg Ser Arg Ala Ala Gly Phe Val
            435                 440                 445

Pro Tyr Val Thr Val Arg Ala Leu Asp Arg Val Thr Val Asn Ala Gly
            450                 455                 460

Trp Asp Pro Gln
465

<210> SEQ ID NO 88
<211> LENGTH: 266
<212> TYPE: PRT
<213> ORGANISM: Burkholderia sp-63093

<400> SEQUENCE: 88

Gln Gly Ala Ala Asp Met Pro Ala Gly Pro Ser Val Ala Leu Tyr Tyr
1               5                   10                  15

Gly Ala Asn Pro Pro Val Glu Glu Leu Ala Thr Phe Asp Val Val
            20                  25                  30

Val Asp Pro Asp Ala His Phe Asp Pro Arg Ala His Ala Lys Ala His
            35                  40                  45

Pro Val Trp Phe Ala Tyr Val Ser Val Gly Glu Val Asn Pro His Arg
            50                  55                  60

Ala Tyr Tyr Ser Ala Met Pro Ser Ala Trp Leu Pro Gly Val Asn Asp
65                  70                  75                  80

Ala Trp Ala Ser His Val Ile Asp Gln Thr Ala Ala Glu Trp Pro Ala
```

```
                    85                  90                  95
Phe Phe Val Asp Lys Val Ile Ala Pro Leu Trp Lys Lys Gly Tyr Arg
                100                 105                 110
Gly Phe Phe Leu Asp Thr Leu Asp Ser Tyr His Leu Ile Ala Lys Thr
            115                 120                 125
Asp Ala Ala Arg Ala Ala Gln Glu Ala Gly Leu Val Arg Val Ile Arg
        130                 135                 140
Ala Ile Lys Lys Arg Tyr Pro Lys Ala Lys Leu Ile Phe Asn Arg Gly
145                 150                 155                 160
Phe Glu Val Leu Pro Gln Ile His Asp Leu Ala Tyr Met Val Ala Phe
                165                 170                 175
Glu Ser Leu Tyr Arg Gly Trp Asp Ala Gly Lys Gln Arg Tyr Thr Glu
            180                 185                 190
Val Pro Gln Ala Asp Arg Asp Trp Leu Leu Met Gln Ala Ala Thr Ile
        195                 200                 205
Arg Asp Gln Tyr Lys Leu Pro Val Leu Ser Ile Asp Tyr Cys Pro Pro
    210                 215                 220
Ala Asp Asp Thr Cys Ala Ala Thr Ala Ala Arg Ile Thr Gln Ala
225                 230                 235                 240
Gly Phe Val Pro Tyr Val Thr Asp Gly Gly Leu Ala Thr Val Gly Val
                245                 250                 255
Gly Ala Ala Gly Thr Gly Asn Glu Arg Pro
            260                 265

<210> SEQ ID NO 89
<211> LENGTH: 467
<212> TYPE: PRT
<213> ORGANISM: Myxococcus macrosporus

<400> SEQUENCE: 89

Ala Glu Arg Ser Gly Asp Ala Ala Val Leu Ala Asp Ala Arg Thr Leu
1               5                   10                  15
Thr Cys Ala Ser Leu Gln Val Ala Ser Gly Tyr Ile Gly Ser Gly Gln
                20                  25                  30
Thr Val Gln Gly Leu His Thr Gln Thr Leu Ser Gly Thr Gln Asp Arg
            35                  40                  45
Trp Ala Glu Tyr Val Glu Phe Ser Pro Gly Thr Ser Ala Thr Cys Thr
        50                  55                  60
Tyr Ala Leu Pro Ala Asp Val Gly Ala Asp Val Val Ala Ala Glu
65                  70                  75                  80
Val Gly Ile Asn Tyr Arg Gly Pro His Lys Ser Gln Met Arg Trp Leu
                85                  90                  95
Phe Glu Ala Trp Asp Tyr Glu Gly Gly Ala Trp Val Leu Val Gly Asp
                100                 105                 110
Asn Thr Phe Ala Gln Ser Trp Thr Trp Thr Ala Thr Ser Leu Ala Leu
            115                 120                 125
Thr Ser Pro Gln Arg Phe Val Ser Gly Gly Pro Val Lys Leu Arg Tyr
        130                 135                 140
Arg Thr Thr Ser Thr Ala Asp Ala Ser Leu Leu Asp Leu Leu Val Val
145                 150                 155                 160
Arg Ile Gln Val Ala Ala Ser Asp Ala Gly Thr Pro Gly Asp Ala Gly
                165                 170                 175
Thr Pro Gly Asp Ala Gly Thr Pro Gly Asp Ala Gly Thr Glu Thr Asp
            180                 185                 190
```

```
Ala Gly Thr Pro Val Gln Trp Glu Gly Val Asn Ser Phe Thr Tyr Gln
            195                 200                 205

Leu Thr Asn Tyr Pro Gln Gly Lys Leu Asp Thr Ile Ala Ala Ser Lys
        210                 215                 220

Phe Asp Leu Ala Ile Val Asp Leu Ala Arg Asp Gly Tyr Asp Asp Trp
225                 230                 235                 240

Phe Thr Ala Ala Glu Ile Ala Ala Leu Lys Ala Gln Gly Lys Gln Val
                245                 250                 255

Leu Ala Tyr Phe Glu Ile Gly Ala Ile Glu Asn Tyr Arg Pro Glu Trp
            260                 265                 270

Ser Gln Val Pro Asp Asp Leu Lys Leu Gly Pro Val Gly Gly Trp Pro
        275                 280                 285

Asn Glu Gln Tyr Val Lys Tyr Trp Asp Glu Arg Trp Trp Pro Ile Val
290                 295                 300

Gln Gly Arg Ile Asp Gln Ala Leu Ala Ala Gly Phe Thr Gly Cys Tyr
305                 310                 315                 320

Leu Asp Met Val Val Thr Tyr Glu Glu Ile Pro Ala Asn Ser Ala Gly
                325                 330                 335

Thr Asn Arg Ala Asp Leu Ala Arg Lys Met Val Ala Leu Ile Glu Arg
            340                 345                 350

Ile Ser Gln Tyr Ala Lys Ala His Asn Pro Ala Phe Lys Val Met Pro
        355                 360                 365

Gln Asn Ser Pro Glu Leu Val Asp Pro Ala Tyr Leu Pro Ala Ile
        370                 375                 380

Asp Gly Leu Gly Met Glu Asp Met Tyr Trp Ser Asp Asp Asn Pro Cys
385                 390                 395                 400

Asp Glu Gly Trp Cys Glu Glu Asn Arg Thr Asn Ala Ala Arg Val Arg
                405                 410                 415

Ala Ala Gly Lys Leu Val Leu Ser Thr Asp Tyr Ala Thr Gln Ala Ala
            420                 425                 430

His Val Ala Asp Ala Tyr Thr Arg Ser Arg Ala Ala Gly Phe Val Pro
        435                 440                 445

Tyr Val Thr Val Arg Ala Leu Asp Gln Met Thr Val Asn Ala Gly Trp
450                 455                 460

Asp Pro Gln
465

<210> SEQ ID NO 90
<211> LENGTH: 882
<212> TYPE: PRT
<213> ORGANISM: Gallaecimonas pentaromativorans

<400> SEQUENCE: 90

Ser Thr Ser Asp Ser Val Ala Phe Phe Tyr Gly Gln His Gln Pro Leu
1               5                   10                  15

Ala Glu Met Thr Phe Tyr Pro Gly Val Val Gln Pro Asp His Ile
            20                  25                  30

Ser Ala Glu Glu Leu Lys Trp Leu Asn Glu Arg Gly Ile Lys Thr Tyr
        35                  40                  45

Ala Tyr Leu Ser Val Gly Glu Ser Asp Ala Lys Asp Ala Lys Gly Leu
    50                  55                  60

Lys Val Asn Ala Ser Trp Gln Ser Gln Ile Met Asp Gln Thr Ser Thr
65                  70                  75                  80

Arg Trp Lys Asn His Leu Asn Thr Arg Ala Lys Glu Leu Lys Ala Arg
                85                  90                  95
```

```
Gly Phe Tyr Gly Leu Phe Leu Asp Thr Leu Asp Ser Tyr Gln Leu Leu
                100                 105                 110

Pro Gln Asp Gln Gln Pro Val Gln Arg Gln Ala Leu Leu Ala Ala Val
            115                 120                 125

Gln Ser Leu Ser Gly Gln Phe Gln His His Leu Ile Leu Asn Arg Gly
        130                 135                 140

Phe Glu Leu Leu Pro Trp Leu Lys Gly Gln Ala Glu Arg Val Val Ala
145                 150                 155                 160

Glu Gly Leu Leu Ser His Phe Asn Pro Glu Asp Asn Ser Tyr Lys Gly
                165                 170                 175

Thr Ser Gln Ala Asp Gln Gln Trp Leu Ser Ala Gln Leu Asn Thr Ala
            180                 185                 190

Lys Ala Leu Gly Phe Ala Val Gln Val Ile Asp Tyr Ala Pro Phe Ala
        195                 200                 205

Lys Arg Ala Ala Met Ala Gln Gln Ile Ala Lys Ala Gly Phe Ala Pro
210                 215                 220

Trp Val Thr Asp Gly His Leu Leu Thr Trp Gly Ser Glu Leu Thr
225                 230                 235                 240

Pro Val Pro Arg Arg Val Ile Val Pro Phe Asp Ser Thr Leu Lys Pro
            245                 250                 255

Leu Ile Asn Thr Gln Val His Gln Arg Leu Ser Thr Leu Ile Glu Tyr
        260                 265                 270

Leu Gly Tyr Leu Pro Asp Tyr Ile Asp Ile Ser Lys Glu Pro Leu Pro
        275                 280                 285

Pro Ala Asp Lys Ala Leu Phe Ala Gly Val Val Trp Ala Glu Ser
290                 295                 300

Ala Ala Phe Tyr Arg Pro Glu Leu Val Ser Trp Leu Glu Lys Val Gln
305                 310                 315                 320

Gly Lys Leu Pro Glu Leu Leu Gly Glu Ile Pro Gln Ser Pro Ala
            325                 330                 335

Leu Leu Ala Gly Leu Gly Leu Asn Leu Gln Ser Leu Ser Pro Lys Gly
        340                 345                 350

Pro Phe Ser Gln Thr Glu Met Ala Ser Trp Lys Gly Glu Thr Ala
        355                 360                 365

Leu Ser Leu Lys Asn Leu Glu Pro Tyr Ser Ala Thr Leu Ala Glu Gly
370                 375                 380

Ala Glu Ala Leu Ile Ser Ile Lys Ala Gly Asn Gly Glu Pro Val Leu
385                 390                 395                 400

Gln Gly Ala Arg Thr Asp Lys Gly Ala Val Val Leu Ser Pro Trp Leu
            405                 410                 415

Ile Asp Ala Leu Pro Leu Glu Glu Asn Arg Trp Leu Ile Asn Pro Val
        420                 425                 430

Ala Leu Leu Gln Lys Gly Leu Gly Leu Pro Pro Ile Pro Ala Pro Asp
        435                 440                 445

Val Thr Thr Glu Ser Gly Arg Arg Leu Phe Thr Leu His Ile Asp Gly
        450                 455                 460

Asp Ala Phe Pro Ser Arg Ala Arg Phe Pro Gly Gln Pro Phe Ala Gly
465                 470                 475                 480

Glu Val Met Glu Lys Gln Ile Ile Glu His Tyr Gln Leu Pro Ile Thr
            485                 490                 495

Val Ser Val Ile Gln Gly Glu Val Gly Pro Thr Gly Met Tyr Pro Lys
            500                 505                 510
```

Gln Ser Pro Gln Leu Glu Ala Ile Ala Arg Asp Ile Phe Thr Lys Pro
            515                 520                 525

Tyr Val Glu Ile Ala Ser His Thr Tyr Ser His Pro Phe Phe Trp Ser
530                 535                 540

Gln Ile Ala Gly Arg Glu Lys Leu Thr Glu Gln Asp Thr Glu Tyr Gly
545                 550                 555                 560

Phe His Leu Asn Ile Pro Gly Tyr Asn Lys Ile Asp Leu Thr Lys Glu
                565                 570                 575

Ile Asp Gly Ser Ile Asp Tyr Ile Asn Glu Arg Leu Ala Pro Lys Asp
            580                 585                 590

Lys Lys Val Val Met Met Leu Trp Ser Gly Asp Ala Ala Pro Gly Pro
        595                 600                 605

Val Ala Leu Ala His Ala Arg Lys Met Gly Val Leu Asn Val Asn Gly
    610                 615                 620

Gly Asn Thr Val Met Thr Arg Asp Asn Pro Ser Leu Ser Glu Ile Trp
625                 630                 635                 640

Pro Ile Gly Arg Pro Glu Gly Asp Leu Leu Tyr Gln Val Tyr Ala Pro
                645                 650                 655

Ile Met Asn Glu Asn Val Tyr Thr Asp Leu Trp His Gly Pro Tyr Phe
            660                 665                 670

Gly Phe Arg Arg Val Arg Glu Thr Phe Asp Ile Thr Gly His Pro Tyr
        675                 680                 685

Arg Leu Lys Pro Phe Gly Leu Tyr Phe His Phe Tyr Ser Ala Thr Asn
    690                 695                 700

Pro Ala Gly Leu Gln Ala Leu Arg Asp Asp Ile Gly Tyr Val Leu Gly
705                 710                 715                 720

Arg Pro Asn Thr Pro Ala His Leu Ser His Tyr Ala Arg Met Ala Lys
                725                 730                 735

Asp Phe Tyr Phe Ser Ala Leu Ala Arg Asp Ala Lys Gly Asp Trp Leu
            740                 745                 750

Leu Ser Ser Lys Tyr Leu Arg Thr Leu Arg Leu Pro Lys Ala Leu Gly
        755                 760                 765

Tyr Ala Gln Leu Asp Ala Ser Gln Gly Leu Ala Gly Ala Thr Glu Asp
    770                 775                 780

Gly Arg Tyr Leu His Val Val Asn Gly Asp Ala Arg Phe Ala Leu Ala
785                 790                 795                 800

Ala Ser Ala Ser Pro Arg Lys Pro Tyr Leu Val Ser Ala Asn Val Leu
                805                 810                 815

Leu Lys Ser Trp Gln Leu Pro Gly Lys Val Ala Phe Lys Ala Trp Gln
            820                 825                 830

Lys Ala Asp Leu Ile Leu Ala Asn Ala Glu Gly Cys Arg Phe Val Ser
        835                 840                 845

Asp Gln Gly Pro Ser Tyr Gly Gly Gln Gln Lys Gly Arg Leu Thr Glu
    850                 855                 860

Phe Ser Leu Pro Glu Gly Asp Phe Ala Gly His Leu Ala Cys Gly Thr
865                 870                 875                 880

Gln Gln

<210> SEQ ID NO 91
<211> LENGTH: 279
<212> TYPE: PRT
<213> ORGANISM: Nonomuraea coxensis

<400> SEQUENCE: 91

Pro Arg Val Pro Leu Thr Glu Val Arg Ser Phe Thr Tyr Val Leu Gln
1               5                   10                  15

Asn Tyr Pro Gly Gly Arg Leu Asp Thr Val Ala Arg Ala Pro His Gln
            20                  25                  30

Leu Ala Ile Val Asp Leu Ser Arg Asp Gly Thr Thr Ala Gly Tyr Phe
        35                  40                  45

Ser Ala Lys Glu Val Ala Lys Val Arg Asp Ser Gly Lys Thr Val Leu
50                  55                  60

Ala Tyr Phe Glu Ile Gly Ser Ile Glu Arg Phe Arg Thr Glu Ala Arg
65                  70                  75                  80

Thr Leu Pro Ala Asp Leu Arg Leu Asn Arg Trp Leu Asp Trp Pro Glu
                85                  90                  95

Glu His Phe Val Arg Tyr Trp Asp Ser Arg Trp Trp Asp Leu Val Leu
                100                 105                 110

Arg Pro Arg Val Asp Gln Ala Leu Arg Ala Gly Phe Asp Gly Val Tyr
            115                 120                 125

Leu Asp Thr Pro Leu Ala Tyr Glu Glu Ile His Leu Asp Arg Val Pro
        130                 135                 140

Gly Glu Thr Arg Ala Ser Leu Ala Arg Arg Met Asn Glu Leu Ile Val
145                 150                 155                 160

Arg Ile Ser Arg Tyr Ala Lys Lys Val Arg Pro Gly Phe Leu Ile Val
                165                 170                 175

Pro Gln Asn Ser Pro Glu Leu Arg Leu Gln Pro Gly Tyr Val Glu Ala
            180                 185                 190

Ile Asp Gly Ile Gly Met Glu Glu Leu Phe Phe Arg Ala Thr Gly Arg
        195                 200                 205

Pro Cys Thr Thr Gly Trp Cys Ala Glu Asn Leu Ala His Ala Leu Ala
210                 215                 220

Leu Arg Lys Leu Gly Lys Ala Val Leu Ala Thr Asp Tyr Ala Thr Arg
225                 230                 235                 240

Pro Ala Asp Val Ala Ala Ala Cys Ala Arg Tyr Arg Arg His Gly Ile
                245                 250                 255

Ala Gly Asn Val Thr Val Val Asp Leu Asp Arg Val Ser Pro Leu Cys
            260                 265                 270

Thr Val Ala Lys Glu Gly Ala
        275

<210> SEQ ID NO 92
<211> LENGTH: 276
<212> TYPE: PRT
<213> ORGANISM: Glycomyces rutgersensis

<400> SEQUENCE: 92

Asp Ser Gly Glu Thr Ala Thr Ala Ala Pro Ala Asp Gln Pro Ala Asn
1               5                   10                  15

Trp Ile Tyr Gln Leu Ser Gly Tyr Ala Asp Gly Lys Leu Asp Ala Leu
            20                  25                  30

Val Ala Ala Pro His Glu Ala Ala Val Ile Asp Leu Ala Arg Asp Gly
        35                  40                  45

Gly Glu Gly Tyr Phe Ser Ala Asp Glu Ile Thr Ser Leu Glu Asn Ser
    50                  55                  60

Gly Lys Ser Val Tyr Ala Tyr Phe Thr Met Gly Ser Ile Glu Thr Tyr
65                  70                  75                  80

Arg Pro Glu Tyr Asp Ala Val Ala Ala Thr Asp Met Ile Leu Asn Gln
                85                  90                  95

Trp Gly Asp Trp Pro Asp Glu Tyr Phe Val Gln Tyr Trp Asp Gln Glu
                100                 105                 110

Trp Trp Asp Leu Val Met Gln Pro Arg Leu Asp Gln Ala Ala Ala Ala
            115                 120                 125

Gly Phe Asp Gly Val Tyr Leu Asp Val Pro Asn Ala Tyr Glu Glu Ile
        130                 135                 140

Asp Leu Ala Leu Val Pro Gly Glu Thr Arg Glu Ser Leu Ala Gln Lys
145                 150                 155                 160

Met Val Asp Leu Val Ile Arg Ala Gln Glu Tyr Ala Gly Asp Asp Leu
                165                 170                 175

Gln Ile Leu Val Gln Asn Ser Pro Glu Leu Arg Glu Tyr Pro Gly Tyr
            180                 185                 190

Leu Asp Ala Ile Asp Gly Ile Gly Ile Glu Glu Leu Phe Phe Leu Asn
        195                 200                 205

Ala Asp Glu Pro Cys Thr Glu Asp Trp Cys Ala Glu Asn Leu Asp Asn
210                 215                 220

Thr Arg Ala Ile Arg Asp Ala Gly Lys Leu Val Leu Ala Val Asp Tyr
225                 230                 235                 240

Ala Ser Glu Pro Ala Asn Thr Ala Ala Ala Cys Glu His Tyr Ala Glu
                245                 250                 255

Glu Gly Phe Ala Gly Ala Val Ala Gly Val Asp Leu Asp Ala Ile Tyr
            260                 265                 270

Glu Pro Cys Pro
        275

<210> SEQ ID NO 93
<211> LENGTH: 277
<212> TYPE: PRT
<213> ORGANISM: Environmental bacterial community XE

<400> SEQUENCE: 93

Ala Ser Pro Ala Leu Ser Ser Val Gly Ser Trp Ile Tyr Gln Leu Gln
1               5                   10                  15

Gly Ala Lys Pro Asp Val Leu Ala Ala Ser Pro Tyr Asp Met Ala Val
            20                  25                  30

Ile Asp Tyr Ser Arg Asp Gly Ser Gly Gly Arg Ala Tyr Ser Arg Ala
        35                  40                  45

Asp Ile Ala Ala Leu Lys Val Lys Pro Asp Gly Gln Arg Ile Val
50                  55                  60

Leu Ala Tyr Leu Ser Ile Gly Glu Ala Glu Asp Tyr Arg Phe Tyr Trp
65                  70                  75                  80

Gly Gln Asp Trp Ser Arg Thr Pro Pro Ser Trp Leu Leu Gly Glu Asn
                85                  90                  95

Pro Asp Trp Glu Gly Asn Tyr Asp Ile Arg Phe Trp Asp Pro Glu Trp
            100                 105                 110

Gln Lys Ile Ile Leu Gly Thr Pro Gln Ser Tyr Leu Asp Arg Ile Leu
        115                 120                 125

Ala Ala Gly Phe Asp Gly Val Tyr Leu Asp Arg Val Asp Ala Tyr Glu
130                 135                 140

Arg Asn Asp Arg Glu Met Asn Ala Pro Gly Arg Ala Ala Met Ile
145                 150                 155                 160

Ala Phe Val Gln Asp Ile Ala Arg Tyr Gly Arg Ala Gln Asn Pro Gln
                165                 170                 175

Phe Leu Val Val Pro Gln Asn Gly Glu Glu Leu Leu Ser Asp Ala Gly

```
                   180                 185                 190
Tyr Arg Gln Val Val Ser Gly Leu Ala Lys Glu Asp Leu Leu Tyr Gly
                195                 200                 205

Leu Asp Gly Asp Glu Ser Arg Asn Arg Asn Gly Glu Ile Arg Ala Ser
            210                 215                 220

Leu Ser Phe Leu Asn Arg Leu Val Ala Glu Gly Lys Pro Val Phe Leu
225                 230                 235                 240

Ala Glu Tyr Leu Ser Ser Pro Glu Leu Ile Asp Thr Ala His Ala Glu
                245                 250                 255

Ala Ser Glu Leu Glu Met Val Leu Phe Ile Gly Asp Arg Glu Leu Asp
            260                 265                 270

Asn Ala Asn Ser Lys
                275

<210> SEQ ID NO 94
<211> LENGTH: 271
<212> TYPE: PRT
<213> ORGANISM: Paraburkholderia phenazinium

<400> SEQUENCE: 94

Gln Thr Ala Ala Asp Ala Ala Asp Asn Ala Ala Ser Ala Thr Asn Ala
1               5                   10                  15

Ser Ala Gln Pro Ser Val Ala Phe Phe Tyr Gly Gly Gln Val Pro Ala
                20                  25                  30

Ala Ala Leu Ser Glu Phe Asp Ala Val Val Glu Pro Asp Ser Gly
            35                  40                  45

Phe Asp Pro Glu Ala Gln His Gly Gly His Thr Ala Trp Phe Ala Tyr
    50                  55                  60

Val Ser Val Gly Glu Val Thr Pro Gln Arg Pro Tyr Tyr Ala Ala Met
65                  70                  75                  80

Pro Lys Glu Trp Leu Val Gly His Asn Ala Ala Trp Glu Ser Lys Val
                85                  90                  95

Val Asp Gln Asp Ala Pro Gly Trp Pro Ala Phe Tyr Leu Lys Gln Val
                100                 105                 110

Ile Ala Pro Leu Trp Arg Lys Gly Tyr Arg Gly Phe Phe Leu Asp Thr
            115                 120                 125

Leu Asp Ser Tyr Gln Leu Ile Ala Lys Thr Asp Ala Asp Arg Gln Arg
130                 135                 140

Gln Gln Ala Gly Leu Val Ala Val Ile Arg Ala Ile Lys Ala Arg Tyr
145                 150                 155                 160

Pro Arg Ala Met Leu Met Phe Asn Arg Gly Phe Glu Ile Leu Pro Gln
                165                 170                 175

Val His Glu Leu Val Tyr Ala Val Ala Phe Glu Ser Leu Tyr Ser Gly
            180                 185                 190

Trp Asp Gln Thr Lys Gln Ser Tyr Thr Gln Val Pro Leu Ala Asp Arg
        195                 200                 205

Asp Trp Leu Leu Gly Gln Ala Arg Ile Ile Arg Glu Gln Tyr Arg Leu
    210                 215                 220

Pro Val Ile Ser Ile Asp Tyr Cys Ala Pro Gly Asp Glu Gln Cys Ala
225                 230                 235                 240

Arg Asp Thr Val Gln Lys Ile Cys Lys Asp Gly Leu Val Pro Tyr Val
                245                 250                 255

Thr Asp Gly Ala Leu Gln Thr Val Gly Val Gly Arg Ala Gly Arg
            260                 265                 270
```

<210> SEQ ID NO 95
<211> LENGTH: 905
<212> TYPE: PRT
<213> ORGANISM: Microbial community

<400> SEQUENCE: 95

```
Ala Ala Leu Pro Gln Pro Ala Ser Val Val Phe Trp Tyr Ala Asp Gln
1               5                   10                  15

Pro Pro Ile Ser Glu Leu Ala Gln Phe Asp Trp Ser Val Val Glu Pro
            20                  25                  30

Gly His Leu Thr Ala Gly Asp Val Lys Thr Leu Arg Lys Leu Gly Ser
        35                  40                  45

Gln Pro Phe Ala Tyr Leu Ser Val Gly Glu Phe His Gly Gly Lys Ala
    50                  55                  60

Glu Leu Glu Lys Ala Ser Leu Thr Gly Ala Val Ser Pro Val Arg Asn
65                  70                  75                  80

Gly Ala Trp Asp Ser Gln Val Met Asp Leu Ala Ala Pro Ala Trp Arg
                85                  90                  95

Glu His Leu Phe Gly Arg Ala Lys Ala Leu Gln Ala Glu Gly Tyr Ala
            100                 105                 110

Gly Leu Phe Leu Asp Thr Leu Asp Ser Phe Gln Leu Leu Pro Glu Ser
        115                 120                 125

Ala Arg Glu Thr Gln Arg Val Ala Leu Ala Gly Phe Leu Arg Glu Leu
    130                 135                 140

His Gln Arg Gln Pro Asn Leu Lys Leu Phe Phe Asn Arg Gly Phe Glu
145                 150                 155                 160

Val Leu Pro Asp Leu Asp Gly Val Ala Ala Val Ala Ile Glu Ser
                165                 170                 175

Ile His Ala Gly Trp Asp Ala Ser Ala Lys Arg Tyr Arg Pro Val Pro
            180                 185                 190

Glu Ala Asp Arg Glu Trp Leu Glu Thr Gln Ile Gln Pro Leu Arg Ala
        195                 200                 205

Lys Gly Ile Pro Leu Val Ala Ile Asp Tyr Leu Pro Pro Glu Arg Arg
    210                 215                 220

Asp Glu Ala Arg Lys Leu Ala Lys Arg Leu Arg Asp Glu Gly Phe Ile
225                 230                 235                 240

Pro Tyr Ile Gly Thr Pro Glu Leu Asp Ser Met Gly Ile Ser Ser Ile
                245                 250                 255

Glu Ile Gln Pro Arg Arg Ile Ala Leu Leu Tyr Asp Pro Arg Glu Gly
            260                 265                 270

Asp Leu Val Arg Asn Ala Gly His Thr Leu Gly Gly Leu Leu Glu
        275                 280                 285

Tyr Leu Gly Tyr Arg Val Asp Tyr Leu Pro Val Asp Gly Ser Leu Pro
    290                 295                 300

Glu His Arg Phe Ser Gly Leu Tyr Ala Gly Ile Val Thr Trp Met Thr
305                 310                 315                 320

Ser Gly Pro Pro Gln Asp Ala Ser Ala Phe Asn Ser Trp Ile Gly Lys
                325                 330                 335

Arg Leu Asp Glu Gln Val Pro Val Phe Phe Ser Gly Leu Pro Ile
            340                 345                 350

Gln Asp Pro Leu Leu Leu Lys Arg Leu Gly Leu Asn Arg Ser Ala Pro
        355                 360                 365

Ile Gly Thr Gln Ala Leu Thr Ile Ser Tyr Gln Asp Lys Ala Leu Ile
    370                 375                 380
```

-continued

```
Gly Ala Phe Glu Ala Pro Val Gln Pro Arg Ser Arg Asp Leu Thr Ala
385                 390                 395                 400

Ile Ser Leu Leu Pro Lys Gly Pro Lys Ala Leu Leu Leu Thr Ala
            405                 410                 415

Ala Asp Gly Gln Thr Phe Ala Pro Val Ala Thr Ala Glu Trp Gly Gly
        420                 425                 430

Val Ala Leu Ala Pro Tyr Ile Leu Glu Thr Asn Asn Glu Arg Ser Arg
        435                 440                 445

Trp Ile Leu Asp Pro Phe Ala Phe Leu Gln Ala Ser Leu Arg Leu Pro
        450                 455                 460

Val Gln Pro Arg Pro Asp Thr Thr Thr Glu Asn Gly Arg Arg Ile Ala
465                 470                 475                 480

Thr Val His Ile Asp Gly Asp Gly Phe Pro Ser Arg Ala Glu Val Arg
                485                 490                 495

Gly Thr Pro Tyr Ala Gly Lys Gln Val Leu Asp Asp Phe Ile Arg Pro
            500                 505                 510

Asn Pro Phe Leu Thr Ser Val Ser Ile Val Glu Gly Glu Ile Ser Pro
        515                 520                 525

Arg Gly Met Phe Pro Phe Leu Ala Arg Glu Leu Glu Pro Ile Ala Arg
        530                 535                 540

Glu Leu Phe Ala Asn Pro Lys Val Glu Val Ala Thr His Thr Phe Ser
545                 550                 555                 560

His Pro Phe Phe Met Gln Pro Glu Val Ala Gln Lys Arg Glu Asn Phe
                565                 570                 575

Asn Pro Glu Tyr Gly Leu Lys Met Ala Ile Pro Gly Tyr Asp Lys Ile
            580                 585                 590

Asp Phe Arg Arg Glu Ile Phe Gly Ser Arg Asp Tyr Ile Asn Gln Gln
        595                 600                 605

Leu Thr Thr Pro Glu Lys Pro Val Lys Leu Val Phe Trp Pro Gly Asp
        610                 615                 620

Ala Leu Pro Ser Ala Ala Thr Leu Lys Leu Ala Tyr Asp Ala Gly Leu
625                 630                 635                 640

Lys Asn Val Asn Gly Ala Glu Thr Met Leu Thr Lys Ala Asn Pro Ser
                645                 650                 655

Leu Thr Gly Leu Asn Pro Leu Leu Arg Pro Thr Glu Gly Gly Leu Gln
            660                 665                 670

Tyr Tyr Ala Pro Ile Ile Asn Glu Asn Leu Tyr Thr Asn Leu Trp Lys
        675                 680                 685

Gly Pro Tyr Tyr Gly Phe Arg Asp Val Ile Asp Thr Phe Glu Leu Thr
        690                 695                 700

Asp Ser Pro Arg Arg Leu Arg Gly Leu His Leu Tyr Tyr His Phe Tyr
705                 710                 715                 720

Ser Ser Thr Lys Gln Ala Ser Ile Lys Ala Met Asn Glu Ile Tyr Gly
                725                 730                 735

Tyr Met Lys Asp Gln Gln Pro Met Ser Leu Trp Met Ser Asp Tyr Leu
            740                 745                 750

Asp Arg Val His Gly Leu Tyr Gln Ala Ser Leu Ala Arg Thr Ala Glu
        755                 760                 765

Gly Asp Trp Gln Val Arg Gly Met Asp Ala Leu Arg Thr Leu Arg Leu
        770                 775                 780

Asp Pro Gln Met Gly Trp Pro Asp Leu Leu Arg Ser Lys Gly Val Ala
785                 790                 795                 800
```

Gly Val Arg Asp Leu Pro Gln Gly Arg Tyr Val Ala Leu Ser Ser Asp
                805                 810                 815

Gln Ala Leu Leu Val Leu Arg Pro Asp Arg Asp Glu Arg Pro Ala Leu
                820                 825                 830

Glu Glu Ala Asn Leu Pro Leu Val Asp Trp Lys Tyr Val Asp Glu Lys
                835                 840                 845

His Val Ser Phe Ser Phe Ala Gly Gln Val Asp Leu Ser Phe Ser Val
                850                 855                 860

Arg Ser Ala Ser Ser Cys Arg Val Glu Val Asp Gly Gln Thr Phe Ala
865                 870                 875                 880

Ala Lys Ala Ser Ala Gly Leu Trp Thr Phe Gln Leu Pro Met Lys Gln
                885                 890                 895

Val Ser His Gly Gln Leu Tyr Cys Ile
                900                 905

<210> SEQ ID NO 96
<211> LENGTH: 467
<212> TYPE: PRT
<213> ORGANISM: Myxococcus virescens

<400> SEQUENCE: 96

Ala Glu Arg Ser Glu Asp Thr Ala Gly Leu Ala Asp Ala Arg Thr Leu
1               5                   10                  15

Thr Cys Ala Ser Leu Gln Val Ala Ser Gly Ala Ile Gly Ser Gly Gln
                20                  25                  30

Ser Val Gln Gly Leu His Thr Gln Thr Leu Ser Gly Thr Gln Asp Arg
                35                  40                  45

Trp Thr Glu Tyr Val Glu Phe Phe Pro Gly Thr Ser Ala Thr Cys Thr
            50                  55                  60

Tyr Ala Leu Pro Ala Asp Val Gly Ala Ala Asp Val Ile Ala Ala Glu
65                  70                  75                  80

Val Gly Ile Asn Tyr Arg Gly Pro Ala Arg Ser Gln Met Arg Trp Leu
                85                  90                  95

Phe Glu Ala Trp Asp Tyr Ala Ala Gly Ala Trp Val Leu Val Gly Asp
                100                 105                 110

Asn Thr Phe Ala Gln Ser Trp Arg Trp Thr Ala Thr Ser Leu Ala Leu
                115                 120                 125

Thr Ser Pro Gln Arg Phe Val Ser Gly Gly Pro Val Lys Leu Arg Tyr
            130                 135                 140

Arg Thr Thr Ser Thr Ala Asp Ala Ser Leu Leu Asp Leu Leu Val Val
145                 150                 155                 160

Arg Ile Gln Val Ala Ala Ser Asp Ala Gly Thr Pro Gly Asp Ala Gly
                165                 170                 175

Thr Pro Thr Asp Ala Gly Thr Pro Gly Asp Ala Gly Thr Gly Thr Asp
                180                 185                 190

Ala Gly Thr Pro Val Ser Trp Glu Gly Val His Ser Phe Thr Tyr Gln
            195                 200                 205

Leu Thr Asn Tyr Pro Gln Gly Lys Leu Asp Thr Ile Ala Asn Ser Lys
        210                 215                 220

Phe Asp Leu Ala Ile Val Asp Leu Ser Arg Asp Gly Tyr Asp Asp Trp
225                 230                 235                 240

Phe Thr Ala Ala Glu Ile Thr Ala Leu Lys Ala Lys Gly Lys Gln Val
                245                 250                 255

Leu Ala Tyr Phe Glu Ile Gly Ala Ile Glu Glu Tyr Arg Pro Glu Trp
                260                 265                 270

```
Ser Gln Val Pro Glu Asp Leu Lys Leu Gly Pro Val Gly Gly Trp Pro
        275                 280                 285

Asp Glu Gln Tyr Val Lys Tyr Trp Asp Glu Arg Trp Trp Pro Ile Val
    290                 295                 300

Gln Gly Arg Leu Asp Gln Ala Leu Ala Ala Gly Phe Thr Gly Cys Tyr
305                 310                 315                 320

Leu Asp Met Val Val Thr Tyr Glu Glu Ile Pro Ala Asn Ala Ala Gly
                325                 330                 335

Thr Asn Arg Ala Asp Leu Ala Arg Lys Met Val Ala Leu Leu Ala Arg
                340                 345                 350

Ile Asn Gln Tyr Ala Lys Ala Arg Asp Pro Gly Phe Lys Val Met Pro
                355                 360                 365

Gln Asn Ser Pro Glu Leu Val Asp Asp Pro Ala Tyr Leu Pro Ala Ile
        370                 375                 380

Asp Gly Leu Gly Met Glu Asp Leu Tyr Trp Ser Asp Asn Ala Cys
385                 390                 395                 400

Asp Glu Gly Trp Cys Glu Glu Asn Arg Ala Asn Ala Ala Arg Val Arg
                405                 410                 415

Ala Ala Gly Lys Leu Val Leu Ser Thr Asp Tyr Ala Val Gln Ala Ala
                420                 425                 430

Asn Val Ala Asp Ala Tyr Thr Arg Ser Arg Ala Gly Phe Val Pro
                435                 440                 445

Tyr Val Ser Val Arg Ala Leu Asp Arg Met Thr Val Asn Ala Gly Trp
        450                 455                 460

Asp Pro Gln
465

<210> SEQ ID NO 97
<211> LENGTH: 464
<212> TYPE: PRT
<213> ORGANISM: Myxococcus fulvus

<400> SEQUENCE: 97

Ala Cys Gly Asp Lys Ala Pro His Asp Asp Phe Asp Thr Gly Gln Asp
1               5                   10                  15

Ala Ile Leu Pro Asp Ala Arg Thr Leu Pro Cys Thr Thr Leu Gln Phe
                20                  25                  30

Glu Arg Gly Ala Leu Pro Ser Gly Gln Ser Val Gln Gly Leu Asn Thr
            35                  40                  45

Gln Thr Leu Ser Gly Thr Gln Asp Arg Trp Ala Glu Tyr Val Glu Phe
        50                  55                  60

Ala Pro Asn Ser Ser Ala Thr Cys Thr His Pro Leu Pro Thr Gly Val
65                  70                  75                  80

Ser Ala Asp Ser Val Val Ala Glu Val Gly Val Asn Tyr Arg Gly
                85                  90                  95

Pro Thr Lys Ala Gln Met Arg Trp Val Ile Glu Ala Trp Asp Tyr Ser
                100                 105                 110

Thr Asn Ser Trp Ala Leu Val Gly Asp Asn Thr Phe Ala Gln Ser Trp
            115                 120                 125

Arg Trp Thr Ala Thr Ser Leu Ala Leu Pro Thr Pro Ala Arg Phe Leu
        130                 135                 140

Ser Gly Gly Pro Val Lys Leu Arg Tyr Arg Thr Asp Ser Thr Ala Asp
145                 150                 155                 160

Ala Ser Leu Leu Asp Leu Leu Val Val Arg Val Gln Val Ala Ala Ser
```

Asp Ala Gly Thr Pro Thr Asp Ala Gly Thr Pro Thr Asp Ala Gly Thr
            165                 170                 175

Gln Val Pro Trp Ser Asn Val Lys Ser Phe Thr Tyr Gln Leu Thr Asn
        180                 185                 190

Tyr Pro Gln Gly Lys Leu Asp Ala Ile Ala Ala Ser Lys Phe Asp Leu
    195                 200                 205

Ala Ile Val Glu Leu Val Arg Asp Gly Ser Ser Gly Tyr Phe Thr Ala
210                 215                 220

Ala Glu Ile Ser Ala Leu Lys Ala Arg Gly Lys Gln Val Leu Ala Tyr
225                 230                 235                 240

Phe Glu Ile Gly Ala Ile Glu Glu Tyr Arg Pro Glu Trp Ser Gln Val
            245                 250                 255

Pro Ala Asp Leu Lys Leu Gly Pro Val Ser Gly Trp Pro Asp Glu Gln
        260                 265                 270

Tyr Val Lys Tyr Trp Asp Glu Arg Trp Trp Pro Ile Val Gln Gly Arg
    275                 280                 285

Ile Asp Arg Ala Leu Ala Ala Gly Phe Asn Gly Cys Tyr Leu Asp Met
290                 295                 300

Val Val Thr Tyr Glu Glu Ile Pro Ala Asn Ser Ala Gly Thr Asn Arg
305                 310                 315                 320

Ala Asp Leu Ala Arg Lys Met Val Ala Leu Ile Ala Arg Ile Asn Thr
            325                 330                 335

Tyr Ala Lys Ala Arg Asn Pro Asp Phe Lys Val Val Pro Gln Asn Ser
        340                 345                 350

Pro Glu Leu Val Asp Asp Pro Ala Tyr Leu Pro Ala Ile Asp Gly Leu
    355                 360                 365

Gly Met Glu Asp Met Tyr Trp Ser Asp Val Ala Cys Asp Glu Gly
370                 375                 380

Trp Cys Glu Glu Asn Arg Thr Asn Ala Ala Arg Val Arg Ala Ala Gly
385                 390                 395                 400

Lys Leu Val Leu Ser Thr Asp Tyr Ala Thr Gln Ser Ala His Val Ala
            405                 410                 415

Asp Ala Tyr Thr Arg Ser Arg Ala Ala Gly Phe Val Pro Tyr Val Thr
        420                 425                 430

Val Arg Ala Leu Asp Arg Val Thr Val Asn Ala Gly Trp Asp Pro Gln
    435                 440                 445

450                 455                 460

<210> SEQ ID NO 98
<211> LENGTH: 475
<212> TYPE: PRT
<213> ORGANISM: Myxococcus macrosporus

<400> SEQUENCE: 98

Arg Asp Ser Leu Asp Asp Glu Arg Gly Ala Ile Leu Pro Asp Ala Gln
1               5                   10                  15

Thr Leu Thr Cys Ala Thr Leu Gln Leu Ala Arg Gly Ser Ile Gly Ser
            20                  25                  30

Gly Gln Gly Val Gln Gly Leu His Thr Gln Thr Leu Ser Gly Thr Gln
        35                  40                  45

Asp Arg Trp Ala Glu Tyr Val Glu Phe Ala Pro Asn Ser Ser Ala Thr
    50                  55                  60

Cys Thr Tyr Pro Leu Pro Ala Gly Val Ser Ala Asp Thr Val Val Ala
65                  70                  75                  80

-continued

```
Ala Glu Ile Gly Val Asn Phe Arg Gly Pro Thr Lys Ser Ala Met Arg
             85                  90                  95

Trp Leu Phe Glu Ala Trp Asp Tyr Ser Thr Gly Ala Trp Val Val Val
        100                 105                 110

Gly Asp Asn Val Phe Ala Gln Ser Trp Lys Trp Ser Ala Thr Ser Leu
        115                 120                 125

Ala Leu Thr Ser Pro Ser Arg Phe Phe Ser Gly Pro Val Lys Leu
130                 135                 140

Arg Tyr Arg Thr Glu Ser Ser Ala Asp Ala Ser Leu Leu Asp Leu Leu
145                 150                 155                 160

Val Val Arg Val Gln Val Ala Ala Thr Asp Ala Gly Thr Pro Thr Asp
                165                 170                 175

Ala Gly Thr Pro Thr Asp Ala Gly Thr Pro Thr Asp Ala Gly Thr Pro
                180                 185                 190

Thr Asp Ala Gly Thr Ser Thr Asp Ala Gly Thr Pro Val Pro Trp Glu
                195                 200                 205

Gly Val Ser Ser Phe Thr Tyr Gln Leu Thr Asn Tyr Pro Gln Gly Lys
        210                 215                 220

Leu Asp Ala Ile Ala Ala Ser Lys Phe Asp Leu Ala Ile Val Glu Leu
225                 230                 235                 240

Val Arg Asp Gly Ser Ser Gly Tyr Phe Thr Ala Ala Glu Ile Ser Ala
                245                 250                 255

Leu Lys Ala Arg Gly Lys Gln Val Leu Ala Tyr Phe Glu Ile Gly Ala
                260                 265                 270

Ile Glu Glu Tyr Arg Pro Glu Trp Ser Gln Val Pro Ala Asp Leu Lys
        275                 280                 285

Leu Gly Pro Val Asp Gly Trp Pro Asp Glu Gln Tyr Val Lys Tyr Trp
        290                 295                 300

Asp Glu Arg Trp Trp Pro Ile Val Gln Gly Arg Ile Asp Arg Ala Leu
305                 310                 315                 320

Ala Ala Gly Phe Thr Gly Cys Tyr Leu Asp Met Val Val Thr Tyr Glu
                325                 330                 335

Glu Ile Pro Ala Asn Ala Ala Gly Thr Asn Arg Ala Asp Leu Ala Arg
                340                 345                 350

Lys Met Val Ala Leu Ile Ala Arg Ile Ser Gln Tyr Ala Lys Ala Arg
        355                 360                 365

Asn Pro Ala Phe Lys Val Met Pro Gln Asn Ser Pro Glu Leu Val Asp
        370                 375                 380

Asp Pro Ala Tyr Leu Pro Val Ile Asp Gly Leu Gly Met Glu Asp Met
385                 390                 395                 400

Tyr Trp Ser Asp Asp Val Ala Cys Asp Ala Ser Trp Cys Ala Glu Asn
                405                 410                 415

Arg Ala Asn Ala Ala Arg Val Arg Ala Ala Gly Lys Leu Val Leu Ser
                420                 425                 430

Thr Asp Tyr Ala Val Gln Ser Ala His Val Ala Asp Ala Tyr Thr Arg
        435                 440                 445

Ser Arg Ala Ala Gly Phe Val Pro Tyr Val Thr Val Arg Ala Leu Asp
450                 455                 460

Arg Val Thr Val Asn Ala Gly Trp Asp Pro Gln
465                 470                 475
```

<210> SEQ ID NO 99
<211> LENGTH: 469
<212> TYPE: PRT

<213> ORGANISM: Myxococcus stipitatus

<400> SEQUENCE: 99

```
Arg Asp Thr Leu Asp Asp Glu Arg Gly Ala Ile Leu Pro Asp Ala Gln
1               5                   10                  15

Thr Leu Thr Cys Thr Thr Leu Gln Leu Ala Arg Gly Ser Ile Gly Ser
            20                  25                  30

Gly Gln Gly Val Gln Gly Leu His Thr Gln Thr Leu Ser Gly Thr Gln
        35                  40                  45

Asp Arg Trp Ala Glu Tyr Val Glu Phe Thr Ala Asn Ser Ser Ala Thr
    50                  55                  60

Cys Thr Tyr Pro Leu Pro Ala Gly Val Ser Ala Asp Thr Val Val Ala
65                  70                  75                  80

Ala Glu Ile Gly Val Asn Phe Arg Gly Pro Thr Lys Ser Ala Met Arg
                85                  90                  95

Trp Leu Phe Glu Ala Trp Asp Tyr Ser Thr Gly Thr Trp Val Val Val
            100                 105                 110

Gly Asp Asn Ala Phe Ala Gln Ser Trp Lys Trp Ser Ala Thr Ser Leu
        115                 120                 125

Ala Leu Thr Ser Pro Ala Arg Phe Phe Ser Gly Gly Pro Val Lys Leu
130                 135                 140

Arg Tyr Arg Thr Glu Ser Ser Ala Asp Ala Ser Leu Leu Asp Leu Leu
145                 150                 155                 160

Val Val Arg Val Gln Val Ala Ala Ser Asp Ala Gly Thr Ser Thr Asp
                165                 170                 175

Ala Gly Thr Pro Thr Asp Ala Gly Thr Pro Thr Asp Ala Gly Thr Ser
            180                 185                 190

Thr Asp Ala Gly Thr Pro Val Pro Trp Glu Gly Val Ser Ser Phe Thr
        195                 200                 205

Tyr Gln Leu Thr Asp Tyr Pro Gln Gly Lys Leu Asp Thr Ile Ala Ala
    210                 215                 220

Ser Lys Phe Asp Leu Ala Ile Ile Glu Leu Val Arg Asp Gly Ser Ser
225                 230                 235                 240

Gly Tyr Phe Thr Ala Ala Glu Ile Ser Ala Leu Lys Ala Gly Gly Lys
                245                 250                 255

Gln Val Leu Ala Tyr Phe Glu Ile Gly Ala Ile Glu Glu Tyr Arg Pro
            260                 265                 270

Glu Trp Ser Gln Val Pro Ser Asp Met Lys Leu Gly Pro Val Asp Gly
        275                 280                 285

Trp Pro Asp Glu Gln Tyr Val Lys Tyr Trp Asp Glu Arg Trp Trp Pro
    290                 295                 300

Ile Val Gln Gly Arg Leu Asp Arg Ala Leu Ala Ala Gly Phe Thr Gly
305                 310                 315                 320

Cys Tyr Leu Asp Met Val Val Thr Tyr Glu Glu Ile Pro Ala Asn Ser
                325                 330                 335

Ala Gly Thr Asn Arg Ala Asp Leu Ala Arg Lys Met Val Ala Leu Ile
            340                 345                 350

Ala Arg Ile Ser Gln Tyr Ala Lys Ala Arg Asn Pro Ala Phe Lys Val
        355                 360                 365

Met Pro Gln Asn Ser Pro Glu Leu Val Asp Asp Pro Ile Tyr Leu Pro
    370                 375                 380

Ala Ile Asp Gly Leu Gly Met Glu Asp Met Tyr Trp Ser Asp Asp Val
385                 390                 395                 400
```

```
Ala Cys Asp Ala Gly Trp Cys Ala Glu Asn Arg Ala Asn Ala Ala Arg
            405                 410                 415

Val Arg Ala Ala Gly Lys Leu Val Leu Ser Thr Asp Tyr Ala Val Gln
        420                 425                 430

Ser Ala His Val Ala Asp Ala Tyr Thr Arg Ser Arg Ala Ala Gly Phe
            435                 440                 445

Ile Pro Tyr Val Thr Val Arg Ala Leu Asp Arg Val Thr Val Asn Ala
        450                 455                 460

Gly Trp Asp Pro Gln
465

<210> SEQ ID NO 100
<211> LENGTH: 475
<212> TYPE: PRT
<213> ORGANISM: Myxococcus macrosporus

<400> SEQUENCE: 100

Arg Asp Pro Leu Asp Asp Glu Arg Gly Ala Ile Leu Pro Asp Ala Gln
1               5                   10                  15

Thr Leu Thr Cys Ala Thr Leu Gln Leu Ala Arg Gly Ser Ile Gly Ser
            20                  25                  30

Gly Gln Gly Val Gln Gly Leu His Thr Gln Thr Leu Ser Gly Thr Gln
        35                  40                  45

Asp Arg Trp Ala Glu Tyr Val Glu Phe Thr Ala Asn Ser Ser Ala Thr
    50                  55                  60

Cys Thr Tyr Pro Leu Pro Ser Gly Val Ser Ala Asp Thr Val Val Ala
65                  70                  75                  80

Ala Glu Ile Gly Val Asn Phe Arg Gly Pro Thr Lys Ser Ala Met Arg
                85                  90                  95

Trp Leu Phe Glu Ala Trp Asp Tyr Ser Thr Gly Ala Trp Val Ile Val
            100                 105                 110

Gly Asp Asn Ala Phe Ala Gln Ser Trp Lys Trp Ser Ala Thr Ser Leu
        115                 120                 125

Ala Leu Thr Ser Pro Ala Arg Phe Phe Ser Gly Gly Pro Val Lys Leu
    130                 135                 140

Arg Tyr Arg Thr Glu Ser Ser Ala Asp Ala Ser Leu Leu Asp Leu Leu
145                 150                 155                 160

Val Val Arg Val Gln Val Ala Ser Asp Ala Gly Thr Leu Thr Asp
                165                 170                 175

Ala Gly Thr Pro Asn Asp Ala Gly Thr Pro Thr Asp Ala Gly Thr Pro
            180                 185                 190

Thr Asp Ala Gly Thr Ser Thr Asp Ala Gly Thr Pro Val Pro Trp Glu
        195                 200                 205

Gly Val Ser Ser Phe Thr Tyr Gln Leu Thr Asn Tyr Pro Gln Gly Lys
    210                 215                 220

Leu Asp Ala Ile Ala Ala Ser Lys Phe Asp Leu Ala Ile Val Glu Leu
225                 230                 235                 240

Val Arg Asp Gly Ser Ser Gly Tyr Phe Thr Ala Ala Glu Ile Ser Ala
                245                 250                 255

Leu Lys Thr Arg Gly Lys Gln Val Leu Ala Tyr Phe Glu Ile Gly Ala
            260                 265                 270

Ile Glu Glu Tyr Arg Pro Glu Trp Asn Gln Val Pro Ala Asp Leu Lys
        275                 280                 285

Leu Gly Pro Val Asp Gly Trp Pro Asp Glu Gln Tyr Val Lys Tyr Trp
    290                 295                 300
```

```
Asp Glu Arg Trp Trp Pro Ile Val Gln Gly Arg Ile Asp Arg Ala Leu
305                 310                 315                 320

Ala Ala Gly Phe Thr Gly Cys Tyr Leu Asp Met Val Val Thr Tyr Glu
                325                 330                 335

Glu Ile Pro Ala Ser Ser Ala Gly Thr Asn Arg Ala Asp Leu Ala Arg
            340                 345                 350

Lys Met Val Ala Leu Ile Ala Arg Ile Ser Gln Tyr Ala Lys Ala Arg
                355                 360                 365

Asn Pro Ala Phe Lys Val Val Pro Gln Asn Ser Pro Glu Leu Val Asp
            370                 375                 380

Asp Pro Ile Tyr Leu Pro Ala Ile Asp Gly Leu Gly Met Glu Asp Met
385                 390                 395                 400

Tyr Trp Ser Asp Asp Val Ala Cys Asp Ala Gly Trp Cys Ala Glu Asn
                405                 410                 415

Arg Ala Asn Ala Ala Arg Val Arg Ala Ala Gly Lys Leu Val Leu Ser
            420                 425                 430

Thr Asp Tyr Ala Val Gln Ser Ala His Val Ala Asp Ala Tyr Thr Arg
                435                 440                 445

Ser Arg Ala Ala Gly Phe Val Pro Tyr Val Thr Val Arg Ala Leu Asp
450                 455                 460

Arg Val Thr Val Asn Ala Gly Trp Asp Pro Gln
465                 470                 475

<210> SEQ ID NO 101
<211> LENGTH: 906
<212> TYPE: PRT
<213> ORGANISM: Pseudomonas seleniipraecipitans

<400> SEQUENCE: 101

Ala Gly Leu Ser Pro Ala Gly Pro Gln Ser Val Ala Phe Trp Tyr Ala
1               5                   10                  15

Pro Asn Pro Tyr Ser Glu Leu Ala Gln Phe Asp Trp Ser Val Leu
            20                  25                  30

Glu Pro Ser His Val Gln Ala Lys Asp Val Ala Phe Leu Arg Ala Gln
            35                  40                  45

Gly Asn Gln Pro Phe Ala Tyr Leu Ser Ile Gly Glu Phe Asp Gly Asp
        50                  55                  60

Leu Ala Val Val Thr Gly Ser Ala Ser Asn Ser Gly Ala Ser Ala Val
65                  70                  75                  80

Gln Asn Lys Ala Trp Gly Ser Gln Val Met His Leu Ser Ser Pro Glu
                85                  90                  95

Trp Arg Ala Tyr Leu Leu Arg Arg Ala Ser Glu Leu Arg Glu Ala Gly
            100                 105                 110

Tyr Ala Gly Leu Phe Leu Asp Thr Leu Asp Ser Phe Gln Leu Leu Pro
        115                 120                 125

Ala Ala Glu His Glu Thr Gln Arg Ala Leu Arg Asp Phe Leu Ser
    130                 135                 140

Glu Leu Lys Arg Gln Glu Pro Gly Leu Lys Leu Phe Asn Arg Gly
145                 150                 155                 160

Phe Glu Val Leu Pro Glu Leu Pro Gly Val Ala Ala Val Ala Val
                165                 170                 175

Glu Ser Ile His Ala Gly Trp Asp Ala Gln Arg Arg Thr Tyr Arg Ile
            180                 185                 190

Val Pro Gln Ala Asp Arg Asp Trp Leu Asp Gly His Leu Gln Pro Leu
```

-continued

```
            195                 200                 205
Arg Asp Lys Gly Ile Pro Leu Val Ala Ile Glu Tyr Leu Pro Pro Asp
    210                 215                 220
Arg Arg Asn Glu Ala Pro Ala Leu Val Ala Arg Leu Val Ser Glu Gly
225                 230                 235                 240
Phe Val Pro Tyr Val Thr Val Pro Asn Leu Asp Tyr Leu Gly Val Ser
                245                 250                 255
Thr Val Asp Val Gln Pro Arg Arg Ile Ala Met Ile Phe Asp Pro Arg
                260                 265                 270
Glu Gly Thr Leu Tyr Gln Asn Pro Gly His Met Tyr Val Gly Gly Leu
                275                 280                 285
Leu Glu Tyr Leu Gly Tyr Arg Val Asp Tyr Phe Glu Ala Asp Gln Leu
    290                 295                 300
Pro Asn Arg Pro Met Ser Gly Leu Tyr Ala Gly Val Val Val Trp Met
305                 310                 315                 320
Thr Ser Gly Pro Pro Glu Asn Ala Leu Val Phe Asn Gln Trp Leu Ser
                325                 330                 335
Ala Arg Ala Asp Glu His Val Pro Leu Ala Phe Leu Ala Gly Leu Pro
                340                 345                 350
Val Glu Asn Asp Gly Val Leu Arg Arg Phe Gly Leu Arg Arg Thr Phe
                355                 360                 365
Thr Pro Leu Thr Ala Pro Ala Glu Val Ala Gln Asp Asp Ala Leu
    370                 375                 380
Ile Gly His Phe Glu Ala Pro Val Val Arg Thr Arg Asp Leu Pro
385                 390                 395                 400
Ser Leu Thr Thr Leu Asp Gly Gly Pro Thr Pro Val Leu Gly Leu Arg
                405                 410                 415
Asp Ser Gln Gln Arg Ile Phe Thr Pro Val Ala Ile Gly Asp Trp Gly
                420                 425                 430
Gly Ile Ala Leu Ser Pro Tyr Val Val Glu Glu Gly Ala Asp Gln Arg
                435                 440                 445
Arg Trp Ile Ile Asp Pro Phe Ala Phe Leu Gln Lys Ala Leu Arg Leu
    450                 455                 460
Pro Ala Met Pro Arg Pro Asp Thr Thr Thr Glu Asn Gly Arg Arg Val
465                 470                 475                 480
Ala Thr Val His Ile Asp Gly Asp Gly Phe Val Ser Arg Ala Glu Ala
                485                 490                 495
Val Gly Thr Pro Tyr Ser Gly Asp Leu Val Leu Arg Asp Phe Ile Lys
                500                 505                 510
Pro Tyr Pro Phe Leu Thr Ser Val Ser Val Ile Glu Gly Glu Val Gly
                515                 520                 525
Pro Arg Gly Ala Phe Pro His Leu Ala Arg Glu Leu Glu Pro Ile Ala
                530                 535                 540
Arg Lys Ile Phe Ala Glu Pro Lys Val Glu Val Ala Thr His Thr Phe
545                 550                 555                 560
Ser His Pro Phe Phe Trp Gln Pro Glu Val Ala Glu Lys Arg Glu Gly
                565                 570                 575
Phe Asn Pro Glu Tyr Gly Tyr Met Met Lys Ile Pro Gly Tyr Asp Lys
                580                 585                 590
Leu Asp Phe Asn Arg Glu Ile Ala Gly Ser Thr Ala Tyr Ile Asn Gln
                595                 600                 605
Asn Leu Thr Thr Pro Gln Lys Pro Val Lys Met Val Phe Trp Ser Gly
    610                 615                 620
```

```
Asp Ala Met Pro Asp Glu Ala Thr Ile Lys Leu Ala Tyr Asp Asn Gly
625                 630                 635                 640

Leu Thr Asn Val Asn Gly Gly Asn Thr Ala Leu Thr Asn Ala Tyr Pro
            645                 650                 655

Ser Leu Thr Gly Leu Tyr Pro Leu Ile Arg Pro Thr Ser Gly Gly Ile
        660                 665                 670

His Tyr Tyr Ala Pro Val Ile Asn Glu Asn Val Tyr Thr Asn Leu Trp
    675                 680                 685

Thr Gly Pro Tyr Tyr Gly Phe Arg Gly Val Met Glu Thr Phe Ala Leu
690                 695                 700

Thr Asp Lys Pro Arg Arg Leu Arg Gly Leu His Leu Tyr His Phe
705                 710                 715                 720

Tyr Ser Gly Thr Lys Gln Ala Ser Ile Arg Val Met Asn Asp Ile Tyr
                725                 730                 735

Lys Ser Met Ala Ala Glu His Pro Ile Ser Leu Trp Met Ser Asp Tyr
            740                 745                 750

Val Pro Arg Met His Gly Leu Tyr Gln Ala Ser Leu Ala Arg Arg Ala
        755                 760                 765

Asp Gly Ala Trp Gln Ile Arg Gly Leu Asp Gly Leu Arg Thr Val Arg
    770                 775                 780

Leu Asp Ala Ala Met Gly Trp Pro Asp Leu Ser Arg Ser Ser Gly Val
785                 790                 795                 800

Ala Gly Val Arg Asp Leu Pro Gln Gly Arg Tyr Val His Leu Ala Ser
                805                 810                 815

Gly Gln Ala Val Leu Ala Leu Arg Asp Thr Arg Asp Pro Arg Pro Ala
            820                 825                 830

Leu Glu Glu Ala Asn Leu Pro Leu Leu Ala Trp Thr Tyr Leu Asp Asp
        835                 840                 845

His Arg Val Lys Leu Ser Phe Ala Gly Ser Met Pro Leu Gln Phe Ser
    850                 855                 860

Val Arg Ala Gln Gly Thr Cys Arg Leu Glu Val Ala Gly Lys Ser Tyr
865                 870                 875                 880

Ser Gly Thr Arg Gln Gln Asp Leu Trp Arg Phe Ser Leu Pro Met Glu
                885                 890                 895

Arg Val Leu Asp Ala Gln Leu Thr Cys Arg
            900                 905

<210> SEQ ID NO 102
<211> LENGTH: 905
<212> TYPE: PRT
<213> ORGANISM: Pseudomonas migulae

<400> SEQUENCE: 102

Ala Ala Leu Pro Gln Pro Ser Ser Val Thr Phe Trp Tyr Ala Ala Gln
1               5                   10                  15

Pro Pro Ile Pro Glu Leu Ala Gln Phe Asp Trp Ser Val Val Glu Pro
                20                  25                  30

Gly His Leu Thr Lys Asp Asp Val Lys Thr Leu Arg Asp Leu Gly Ser
            35                  40                  45

Gln Pro Phe Ala Tyr Val Ser Ile Gly Glu Phe Ala Gly Ser Lys Ala
        50                  55                  60

Asp Ile Glu Lys Ala His Leu Ser Asp Ala Ile Ser Pro Val Arg Asn
65                  70                  75                  80

Gly Ala Trp Asp Ser Gln Val Met Asn Leu Ser Ala Pro Ala Trp Arg
```

```
                85                  90                  95
Glu His Leu Phe Gly Arg Ala Lys Thr Leu Gln Ala Glu Gly Tyr Ala
                100                 105                 110
Gly Leu Phe Leu Asp Thr Leu Asp Ser Phe Gln Leu Gln Pro Glu Ala
                115                 120                 125
Asp Arg Glu Lys Gln Arg Leu Ala Leu Ala Ser Phe Leu Arg Glu Leu
                130                 135                 140
His Gln Arg Gln Pro Thr Leu Lys Leu Phe Phe Asn Arg Gly Phe Glu
145                 150                 155                 160
Val Leu Pro Glu Leu Asp Gly Val Ala Ala Val Ala Val Glu Ser
                165                 170                 175
Ile His Ala Gly Trp Asp Ala Thr Ala Lys Arg Tyr Arg Pro Val Pro
                180                 185                 190
Glu Ala Asp Arg Ala Trp Leu Glu Thr Gln Leu Gln Pro Leu Arg Ala
                195                 200                 205
Lys Gly Ile Pro Leu Val Ala Ile Asp Tyr Leu Pro Pro Glu Arg Arg
                210                 215                 220
Asp Glu Ala Arg Lys Leu Ala Lys Arg Leu Arg Glu Glu Gly Phe Ile
225                 230                 235                 240
Pro Tyr Ile Gly Thr Pro Glu Leu Asp Ser Met Gly Ile Ser Asn Ile
                245                 250                 255
Glu Val Gln Pro Arg Arg Val Ala Leu Leu Tyr Asp Leu Arg Glu Asp
                260                 265                 270
Asp Leu Thr Gln Asn Asp Gly His Thr Leu Leu Gly Gly Leu Leu Glu
                275                 280                 285
Tyr Leu Gly Tyr Arg Val Asp Tyr Leu Pro Val Asp Asp Thr Leu Ser
                290                 295                 300
Glu Arg Arg Phe Ser Gly Leu Tyr Ala Gly Val Ile Thr Trp Met Thr
305                 310                 315                 320
Ser Gly Pro Pro Gln Asn Ala Ala Ala Phe Asn Thr Trp Ile Gly Lys
                325                 330                 335
Arg Leu Asp Glu Lys Val Pro Val Val Phe Phe Ala Gly Leu Pro Ile
                340                 345                 350
Gln Asp Thr Ser Leu Leu Lys Arg Leu Gly Leu Asn Arg Thr Ala Pro
                355                 360                 365
Ile Gly Thr Gln Thr Leu Ser Ile Thr Ser Gln Asp Lys Ala Leu Ile
                370                 375                 380
Gly Ala Phe Glu Ala Pro Val Gln Pro Arg Ser Arg Asp Leu Thr Ala
385                 390                 395                 400
Ile Ser Leu Leu Pro Lys Gly Pro Lys Ala Ala Leu Leu Thr Ala
                405                 410                 415
Ala Asp Gly Gln Thr Phe Ala Pro Val Ala Val Ala Asp Trp Gly Gly
                420                 425                 430
Leu Ala Leu Ala Pro Tyr Ile Leu Glu Thr Asn Asn Glu Arg Ser Arg
                435                 440                 445
Trp Ile Leu Asp Pro Phe Ala Phe Leu Gln Ala Ser Leu Arg Leu Pro
                450                 455                 460
Val Gln Pro Arg Pro Asp Thr Thr Thr Glu Asn Gly Arg Arg Ile Ala
465                 470                 475                 480
Thr Val His Ile Asp Gly Asp Gly Phe Pro Ser Arg Ala Glu Val Arg
                485                 490                 495
Gly Thr Pro Tyr Ala Gly Arg Gln Val Tyr Asp Asp Phe Ile Arg Pro
                500                 505                 510
```

```
Asn Pro Phe Leu Thr Ser Val Ser Val Ile Glu Gly Glu Ile Ser Pro
            515                 520                 525

Arg Gly Met Phe Pro Phe Leu Ala Gly Glu Leu Glu Pro Ile Ala Arg
        530                 535                 540

Glu Ile Phe Ala Asp Pro Lys Val Glu Val Ala Thr His Thr Phe Ser
545                 550                 555                 560

His Pro Phe Phe Trp Gln Pro Glu Leu Ala Lys Lys Gln Glu Asn Phe
                565                 570                 575

Ser Pro Glu Tyr Gly Leu Asn Met Ala Ile Pro Asn Tyr Asp Lys Ile
            580                 585                 590

Asp Phe Arg Arg Glu Ile Phe Gly Ser Arg Asp Tyr Ile Asn Gln Gln
        595                 600                 605

Leu Thr Thr Pro Glu Lys Pro Val Lys Met Val Phe Trp Pro Gly Asp
    610                 615                 620

Ala Leu Pro Ser Ala Ser Ser Ile Lys Leu Ala Tyr Asp Ala Gly Leu
625                 630                 635                 640

Lys Asn Val Asn Gly Ala Ala Thr Met Leu Thr Lys Ala Asn Pro Ser
                645                 650                 655

Met Thr Gly Leu Gln Pro Leu Leu Arg Pro Thr Glu Gly Gly Leu Gln
            660                 665                 670

Tyr Tyr Ala Pro Ile Ile Asn Glu Asn Leu Tyr Thr Asn Leu Trp Lys
        675                 680                 685

Gly Pro Tyr Tyr Gly Phe Arg Asp Val Ile Asp Thr Phe Glu Leu Thr
    690                 695                 700

Asp Ser Pro Arg Arg Met Arg Gly Leu His Leu Tyr Tyr His Phe Tyr
705                 710                 715                 720

Ser Ser Thr Lys Gln Ala Ser Ile Lys Val Met Gly Glu Ile Tyr Gly
                725                 730                 735

Tyr Met Lys Thr Gln Gln Pro Met Ser Leu Trp Met Ser Asp Tyr Leu
            740                 745                 750

Asp Arg Leu His Gly Leu Tyr Gln Val Ser Leu Ala Arg Thr Ala Glu
        755                 760                 765

Gly Asp Trp Gln Val Arg Gly Leu Asp Ala Leu Arg Thr Leu Arg Leu
    770                 775                 780

Asp Pro Gln Met Gly Trp Pro Asp Leu Met Arg Ser Gln Gly Val Ala
785                 790                 795                 800

Gly Val Arg Asp Leu Pro Gln Gly Arg Tyr Val Ala Leu Ser Ser Asp
                805                 810                 815

Arg Ala Leu Leu Val Leu Arg Pro Asp Arg Asp Asn His Pro Ala Leu
            820                 825                 830

Glu Glu Ala Asn Leu Pro Leu Val Asp Trp Arg Tyr Val Asn Glu Arg
        835                 840                 845

Gln Val Asp Phe Ser Phe Ala Gly Gln Val Asp Leu Thr Phe Ser Val
    850                 855                 860

Arg Leu Pro Gly Thr Cys Arg Val Glu Val Asp Gly Gln His Phe Ala
865                 870                 875                 880

Gly Lys Ala Ser Ala Gly Leu Trp Thr Phe Gln Leu Pro Met Lys Gln
                885                 890                 895

Val Ser His Gly Gln Leu Phe Cys Ser
            900                 905

<210> SEQ ID NO 103
<211> LENGTH: 905
```

<212> TYPE: PRT
<213> ORGANISM: Pseudomonas corrugata

<400> SEQUENCE: 103

```
Ser Ala Leu Pro Gln Pro Ala Ser Val Ala Phe Trp Tyr Ala Asp Gln
1               5                   10                  15

Pro Pro Leu Ser Glu Leu Ala Gln Phe Glu Trp Ser Val Val Glu Pro
                20                  25                  30

Gly His Met Thr Pro Gly Asp Val Lys Thr Leu Arg Glu Leu Gly Ser
            35                  40                  45

His Pro Phe Ala Tyr Val Ser Val Gly Glu Phe Asp Gly Asn Lys Ala
        50                  55                  60

Glu Ile Asp Lys Ala Gly Leu Arg Gln Ala Val Ser Pro Val Arg Asn
65                  70                  75                  80

Asp Ser Trp Asn Ser Gln Val Met Asp Leu Thr Ala Pro Ala Trp Arg
                85                  90                  95

Glu His Leu Leu Gly Arg Ala Lys Ala Leu Gln Ala Gln Gly Tyr Asp
                100                 105                 110

Gly Leu Phe Leu Asp Thr Leu Asp Ser Phe Gln Leu Leu Pro Glu Gly
            115                 120                 125

Ala Arg Glu Ala Gln Arg Val Ala Leu Ala Ser Leu Leu Arg Glu Met
        130                 135                 140

His Lys Arg Gln Pro Thr Leu Lys Leu Phe Phe Asn Arg Gly Phe Glu
145                 150                 155                 160

Val Leu Pro Glu Leu Asp Gly Val Ala Ala Val Ala Phe Glu Ser
                165                 170                 175

Leu Tyr Ala Gly Trp Asp Ala Ala Lys Arg Tyr Arg Pro Val Pro
                180                 185                 190

Glu Ala Asp Arg Gln Trp Leu Leu Gly Glu Leu Gln Pro Leu Arg Ala
                195                 200                 205

Lys Gly Ile Pro Leu Val Ala Ile Asp Tyr Leu Pro Pro Glu Arg Arg
        210                 215                 220

Asp Glu Ala Arg Lys Leu Ala Lys Arg Leu Arg Asp Glu Gly Phe Ile
225                 230                 235                 240

Pro Phe Ile Ser Thr Pro Glu Leu Asp Ser Ile Gly Leu Ser Asn Ile
                245                 250                 255

Glu Val Gln Pro Arg Arg Ile Ala Phe Val Tyr Asp Glu Arg Glu Gly
                260                 265                 270

Ala Leu Glu Asp Asn Gly Gly His Thr Val Leu Gly Leu Leu Glu
        275                 280                 285

Tyr Leu Gly Tyr Arg Val Asp Tyr Ile Pro Ala Ser Ser Ala Met Pro
        290                 295                 300

Gly Tyr Arg Phe Ser Gly Leu Tyr Ala Gly Val Val Thr Trp Met Thr
305                 310                 315                 320

Ser Gly Pro Pro Gln Asp Ala Pro Ala Phe Asn Arg Trp Ile Thr Ala
                325                 330                 335

Arg Leu Asp Glu Gln Val Pro Val Val Phe Phe Ser Gly Leu Pro Val
                340                 345                 350

Glu Asp Lys Leu Leu Leu Lys Arg Met Gly Leu Lys Arg Glu Ala Pro
                355                 360                 365

Pro Gly Val Gln Pro Leu Thr Ile Thr His Gln Asp Lys Ala Leu Ile
        370                 375                 380

Gly Ala Phe Glu Ala Pro Val Gln Pro Arg Ser Arg Asp Leu Thr Ala
385                 390                 395                 400
```

```
Val Ser Val Leu Pro Asn Gly Pro Lys Pro Val Leu Ser Leu Thr Asn
            405                 410                 415

Ala Ser Gly Glu Val Phe Thr Pro Val Thr Ala Lys Trp Gly Gly
            420                 425                 430

Leu Ala Leu Ala Pro Tyr Leu Leu Glu Ala Asn Asn Glu Arg Ser Arg
            435                 440                 445

Trp Ile Ile Asp Pro Phe Ala Phe Leu Gln Thr Ser Leu Gln Leu Pro
            450                 455                 460

Glu Gln Pro Arg Pro Asp Ser Thr Thr Glu Asn Gly Arg Arg Val Ala
465                 470                 475                 480

Thr Val His Ile Asp Gly Asp Gly Phe Pro Ser Arg Ala Glu Val Arg
            485                 490                 495

Gly Thr Pro Tyr Ala Gly Arg His Thr Leu Asp Asp Tyr Ile Lys Pro
            500                 505                 510

Asn Pro Phe Leu Thr Ser Val Ser Ile Val Glu Gly Glu Ile Ser Pro
            515                 520                 525

Arg Gly Met Phe Pro His Leu Ala Arg Glu Leu Glu Pro Ile Ala Arg
            530                 535                 540

Glu Ile Phe Ala Asn Pro Lys Val Glu Val Ala Thr His Thr Phe Ser
545                 550                 555                 560

His Pro Phe Phe Met Gln Pro Asp Lys Ala Leu Lys Arg Glu Asn Phe
                    565                 570                 575

His Pro Glu Tyr Gly Met Asn Met Ala Ile Pro Gly Tyr Gly Lys Ile
                    580                 585                 590

Asp Phe Arg Arg Glu Ile Phe Gly Ser Arg Asp Tyr Ile Asn Gln Asn
            595                 600                 605

Leu Thr Thr Pro Glu Lys Pro Val Lys Met Val Phe Trp Pro Gly Asp
            610                 615                 620

Ala Leu Pro Ser Ala Ser Thr Leu Lys Leu Ala Tyr Asp Ala Gly Leu
625                 630                 635                 640

Lys Asn Val Asn Gly Ala Glu Thr Met Met Thr Lys Ala Asn Pro Ser
                    645                 650                 655

Val Thr Gly Leu Asn Pro Leu Leu Arg Pro Thr Glu Gly Gly Leu Gln
            660                 665                 670

Tyr Tyr Ala Pro Val Ile Asn Glu Asn Leu Phe Thr Asn Leu Trp Lys
            675                 680                 685

Gly Pro Tyr Tyr Gly Phe Arg Glu Val Ile Asp Thr Phe Glu Leu Thr
            690                 695                 700

Asp Ser Pro Arg Arg Leu Arg Gly Leu His Leu Tyr Tyr His Phe Tyr
705                 710                 715                 720

Ser Ser Thr Lys Gln Ala Ser Ile Lys Ala Met His Glu Ile Tyr Gly
                    725                 730                 735

Phe Met Arg Glu Gln His Pro Leu Ser Leu Trp Met Ser Asp Tyr Ile
                    740                 745                 750

Asp Arg Leu His Gly Leu Tyr Gln Ala Ser Leu Ala Arg Thr Ser Asp
            755                 760                 765

Gly Ala Trp Gln Ile Arg Gly Met Asp Ala Leu Arg Thr Val Arg Leu
            770                 775                 780

Asp Pro Gly Met Gly Trp Pro Asp Leu Leu Arg Ser Gln Gly Ile Ala
785                 790                 795                 800

Gly Val Arg Asp Leu Pro Gln Gly Arg Tyr Val His Leu Ser Ser Asp
            805                 810                 815
```

Arg Ala Leu Leu Val Leu Arg Pro Asp Arg Asp Arg Pro Ala Leu
            820                 825                 830

Glu Glu Ala Asn Leu Pro Leu Val Glu Trp Arg Tyr Leu Asp Asp Arg
            835                 840                 845

Arg Val Ser Phe Gly Phe Ser Gly Gln Phe Asp Leu Thr Phe Ser Val
            850                 855                 860

Arg Ser Ala Asn Pro Cys Arg Val Glu Val Asp Gly Gln Arg Phe Ala
865                 870                 875                 880

Gly Lys Ala Ala Ala Gly Leu Trp Thr Phe Gln Leu Pro Met Lys Gln
                    885                 890                 895

Val Ser His Ala Gln Leu Val Cys Asn
            900                 905

<210> SEQ ID NO 104
<211> LENGTH: 906
<212> TYPE: PRT
<213> ORGANISM: Pseudomonas pelagia

<400> SEQUENCE: 104

Gly Pro Val Lys Ser Gly Pro Ala Ser Val Ala Phe Trp Tyr Ala Glu
1               5                   10                  15

Gln Pro Pro Leu Gly Glu Leu Ala Gln Phe Asp Trp Val Val Phe Glu
                20                  25                  30

Pro Ala His Leu Thr Pro Lys Asp Val Ser Phe Val Ala Gln Gly
            35                  40                  45

Ser Leu Pro Phe Ala Tyr Leu Ser Ile Gly Glu Leu Asn Asp His Leu
    50                  55                  60

Ala Gln Ser Ser Pro Gly Leu Leu Asp Asn Ser Ala Asp Gln Ile Arg
65                  70                  75                  80

Asn Pro Gly Trp Asn Ser His Val Met Asp Leu Thr Ser Ala Gly Trp
                85                  90                  95

Gln Glu His Ile Leu Gly Gln Val Gly Glu Phe Ala Lys Gln Gly Tyr
            100                 105                 110

Ala Gly Val Phe Leu Asp Thr Leu Asp Ser Phe Thr Leu Leu Pro Glu
        115                 120                 125

Asp Gln Arg Pro Ala Gln Arg Asp Ala Leu Ala Ala Leu Leu Arg Asp
    130                 135                 140

Met His Lys Arg Tyr Pro Asp Met Lys Leu Phe Phe Asn Arg Gly Phe
145                 150                 155                 160

Glu Val Leu Ala Asp Val Gln Gln Gly Val Ala Ala Val Ala Val Glu
                165                 170                 175

Ser Ile Tyr Ala Ser Trp Asp Ala Ala Ala Gln Val Tyr Arg Pro Val
            180                 185                 190

Ser Glu Asn Asp Arg Thr Trp Leu Ala Gly Gln Val Gln Pro Leu Arg
        195                 200                 205

Ala Arg Asn Ile Pro Ile Val Ala Ile Asp Tyr Leu Pro Val Glu Arg
    210                 215                 220

Arg Ala Glu Ala Arg Glu Leu Ala Ala Arg Leu Ile Glu Glu Gly Phe
225                 230                 235                 240

Leu Pro Tyr Val Gly Thr Pro Glu Leu Asp Thr Leu Gly Val Ser Ser
                245                 250                 255

Ile Glu Val Gln Pro Arg Arg Ile Ala Val Met Tyr Asp Pro Arg Glu
            260                 265                 270

Gly Glu Leu Thr Arg Thr Gly Gly Phe Arg Ser Leu Gly Gly Leu Leu
        275                 280                 285

```
Glu Tyr Met Gly Tyr Arg Val Asp Tyr Leu Pro Val Glu Gly Ser Leu
    290                 295                 300
Pro Ser Ala Pro Met Thr Gly Leu Tyr Ala Gly Val Ile Val Trp Met
305                 310                 315                 320
Thr Ser Gly Pro Pro Asp Ser Ser Ala Phe Asn Arg Trp Ile Gly
                325                 330                 335
Arg Arg Leu Asp Glu Gly Thr Pro Leu Ala Phe Phe Gln Gly Met Pro
            340                 345                 350
Ile Asp Asp Ala Ala Ile Leu Arg Arg Leu Gly Leu Gln Arg Thr Gly
                355                 360                 365
Val Gln Pro Val Ser Gly Leu Gln Leu Val Asn His Asp Ala Gln Leu
    370                 375                 380
Val Gly Ser Phe Glu Ala Pro Leu Val Val Arg Ser Arg Gly Leu Thr
385                 390                 395                 400
Gly Ile Gly Thr Gln Ser Arg Tyr Asn Lys Val Ala Leu Ala Leu Val
                405                 410                 415
Asp Asp Ala Gly Arg Glu His Thr Pro Val Val Thr Gly Asp Trp Gly
            420                 425                 430
Gly Val Ala Leu Ala Pro Tyr Val Phe Glu Gly Glu Asp Asp Thr Arg
            435                 440                 445
Arg Trp Ile Ile Asp Pro Phe Ala Phe Leu Gln Gln Ala Leu Gln Leu
    450                 455                 460
Pro Ala Gln Pro Ala Pro Asp Val Thr Thr Glu Asn Gly Arg Arg Ile
465                 470                 475                 480
Ala Thr Val His Ile Asp Gly Asp Gly Phe Pro Ser Arg Ala Glu Ile
                485                 490                 495
Pro Gly Thr Pro Tyr Ser Gly Ser Ala Val Leu Asn Gln Phe Ile Lys
            500                 505                 510
Pro Tyr Pro Leu Leu Thr Ser Val Ser Phe Ile Glu Gly Glu Val Gly
    515                 520                 525
Pro Ala Gly Met Tyr Pro Tyr Leu Ser Arg Glu Leu Glu Pro Leu Ala
530                 535                 540
Arg Gln Ile Leu Ala His Glu Arg Val Glu Pro Ala Thr His Thr Tyr
545                 550                 555                 560
Ser His Pro Tyr Phe Trp Gln Ala Glu Arg Asp Ser Gln Arg Glu Gly
                565                 570                 575
Phe Arg Ala Asp Tyr Gly Leu Lys Met Pro Ile Pro Gly Tyr Asp Thr
            580                 585                 590
Ile Asp Phe Arg Arg Glu Val Phe Gly Ser Arg Asp Tyr Val Ala Ser
                595                 600                 605
Arg Leu Ala Pro Ala Asp Lys Pro Val Lys Met Ile Phe Trp Ser Gly
    610                 615                 620
Asp Ala Ile Pro Asp Ala Ala Thr Ile Lys Leu Ser Tyr Asp Ala Gly
625                 630                 635                 640
Met Leu Asn Val Asn Gly Gly Glu Thr Arg Leu Thr Arg Ala Asp Pro
                645                 650                 655
Ser Leu Thr Gly Leu Tyr Pro Leu Leu Arg Pro Thr Ala Gly Gly Leu
            660                 665                 670
Gln Val Tyr Ala Pro Ile Ile Asn Glu Asn Val Tyr Thr Asn Leu Trp
    675                 680                 685
Gln Gly Pro Tyr Tyr Gly Phe Arg Glu Val Val Glu Thr Phe Glu Leu
690                 695                 700
```

Thr Asp Ser Pro Arg Arg Met Arg Gly Leu His Leu Tyr Tyr His Phe
705                 710                 715                 720

Tyr Ser Gly Thr Lys Pro Ala Ala Ile Lys Val Met Gly Asp Ile Tyr
            725                 730                 735

Arg His Met Leu Glu Gln Gln Pro Leu Ser Leu Trp Met Ser Asp Tyr
            740                 745                 750

Leu Leu Arg Ala His Gly Leu His Thr Ala Ser Leu Ala Arg Thr Ser
            755                 760                 765

Ser Gly Ala Trp Gln Ile Arg Ala Leu Gln Gly Leu Arg Thr Val Arg
        770                 775                 780

Leu Asp Pro Ser Leu Gly Trp Pro Asp Leu Met Ala Ser Glu Gly Ile
785                 790                 795                 800

Ala Gly Val Leu Asp Leu Pro Gln Gly Arg Tyr Val His Leu Ser Ala
            805                 810                 815

Asp Arg Ala Val Leu Ala Leu Gln Ala Asn Arg Asp Thr Thr Pro Ala
            820                 825                 830

Leu Glu Gln Ala Asn Val Pro Leu Thr Ala Trp Arg Tyr Leu Asp Glu
            835                 840                 845

Arg Arg Ile Gln Leu Ser Phe Ala Gly Glu Phe Pro Ile Ala Phe Ser
850                 855                 860

Val Arg Ser Ala Ser Pro Cys Arg Leu Asp Val Ala Gly Arg Glu Val
865                 870                 875                 880

Lys Gly Arg Gly Ala Asn Gly Leu Trp His Phe Ser Leu Ser Thr Lys
            885                 890                 895

Gln Val Ser Asp Ala Gln Leu Val Cys Glu
            900                 905

<210> SEQ ID NO 105
<211> LENGTH: 257
<212> TYPE: PRT
<213> ORGANISM: Pseudomonas aeruginosa

<400> SEQUENCE: 105

Gly Gly Pro Ser Ser Val Ala Phe Trp Tyr Ala Glu Arg Pro Pro Leu
1               5                   10                  15

Ala Glu Leu Ser Gln Phe Asp Trp Val Val Leu Glu Ala Ala His Leu
            20                  25                  30

Lys Pro Ala Asp Val Gly Tyr Leu Lys Glu Gln Gly Ser Thr Pro Phe
        35                  40                  45

Ala Tyr Leu Ser Val Gly Glu Phe Asp Gly Asp Ala Ala Ala Ile Ala
    50                  55                  60

Asp Ser Gly Leu Ala Arg Gly Lys Ser Ala Val Arg Asn Gln Ala Trp
65                  70                  75                  80

Asn Ser Gln Val Met Asp Leu Ala Ala Pro Ser Trp Arg Ala His Leu
            85                  90                  95

Leu Lys Arg Ala Ala Glu Leu Arg Lys Gln Gly Tyr Ala Gly Leu Phe
            100                 105                 110

Leu Asp Thr Leu Asp Ser Phe Gln Leu Gln Ala Glu Glu Arg Arg Glu
        115                 120                 125

Gly Gln Arg Arg Ala Leu Ala Ser Phe Leu Ala Gln Leu His Arg Gln
    130                 135                 140

Glu Pro Gly Leu Lys Leu Phe Phe Asn Arg Gly Phe Glu Val Leu Pro
145                 150                 155                 160

Glu Leu Pro Gly Val Ala Ser Ala Val Ala Val Glu Ser Ile His Ala
            165                 170                 175

Gly Trp Asp Ala Ala Gly Gln Tyr Arg Glu Val Pro Gln Asp Asp
                180                 185                 190

Arg Asp Trp Leu Lys Gly His Leu Asp Ala Leu Arg Ala Gln Gly Met
    195                 200                 205

Pro Ile Val Ala Ile Asp Tyr Leu Pro Pro Glu Arg Arg Asp Glu Ala
210                 215                 220

Arg Ala Leu Ala Ala Arg Leu Arg Ser Glu Gly Tyr Val Pro Phe Val
225                 230                 235                 240

Ser Thr Pro Ala Leu Asp Tyr Leu Gly Val Ser Asp Val Glu Val Gln
                245                 250                 255

Pro

<210> SEQ ID NO 106
<211> LENGTH: 269
<212> TYPE: PRT
<213> ORGANISM: Streptomyces griseofuscus

<400> SEQUENCE: 106

Ala Ala Gly Ile Lys Gln Gln Val Ala Pro Ala Tyr Phe Tyr Pro
1               5                   10                  15

Gly Asp Ser Gly Asp Ser Gly Ala Gly Asn Leu Trp Ala Gln Leu Ser
                20                  25                  30

Thr Pro Ala Pro Gly Ala Gly Leu Ala Val Ala Asn Pro Ala Ser Gly
            35                  40                  45

Pro Gly Asp Ser Glu Asp Gly Thr Tyr Ala Asn Ala Ile Arg Thr Ala
        50                  55                  60

His Asn Ala Gly Thr Lys Val Ile Gly Tyr Val Asp Ser Gly Tyr Leu
65                  70                  75                  80

Gly Thr Lys Gly Gly Ala Pro Asp Gly Thr Ser Ile Asp Asp
                85                  90                  95

Trp Val Glu Gly Ala Glu Arg Asn Val Asp Lys Trp Tyr Ser Tyr Tyr
                100                 105                 110

Gly Gly Ser Gly Leu Asp Gly Ile Phe Phe Asp Asp Gly Leu Thr Ala
            115                 120                 125

Cys Gly Thr Pro Ser Asp Ala Asn Ala Phe Val Asp Ala Tyr Lys Arg
130                 135                 140

Leu Gln Ser Tyr Val Lys Gly Lys Asp Ala Asp Ala Lys Val Val Ile
145                 150                 155                 160

Asn Pro Gly Ala Ser Pro Glu Gln Cys Tyr Thr Gly Ala Ala Asp Thr
                165                 170                 175

Leu Val Thr Phe Glu Gly Thr Tyr Asp Asp Tyr Val Asn His Tyr Gly
            180                 185                 190

Asp Asp Arg Glu Ser Trp Glu Ala Ser Asp Pro Ser Lys Ile Trp
        195                 200                 205

His Leu Ile His Thr Thr Gly Ser Gln Ala Arg Met Gln Asn Ala Ile
210                 215                 220

Ala Leu Ser Lys Gln Arg Asn Ala Gly Tyr Val Tyr Ala Thr Asp Asp
225                 230                 235                 240

Asp Asn Ser Arg Pro Ser Gly Gln Asp Trp Gly Asn Pro Trp Asp Thr
                245                 250                 255

Leu Pro Ser Tyr Trp Ser Ala Glu Val Asn Thr Val Asn
            260                 265

<210> SEQ ID NO 107

```
<211> LENGTH: 260
<212> TYPE: PRT
<213> ORGANISM: Lysinibacillus xylanilyticus

<400> SEQUENCE: 107

Thr Glu Ser Thr Thr Ser Ile Gln Ala Lys Leu Ala Asp Ile Lys Glu
1               5                   10                  15

Tyr Lys Tyr Tyr Leu Asp Gln Gly Asn Asp Lys Ile Gly Lys Glu Met
            20                  25                  30

Ala Asn Met Asp Leu Val Ile Val Glu Pro Ile Glu Met Gln Gln Lys
        35                  40                  45

Tyr Ile Asp His Ala Gln Lys Asn Gly Thr Leu Val Tyr Gly Tyr Ile
    50                  55                  60

Asn Ala Met Glu Ala Asp Lys Trp Asn Ser Ala Leu Tyr Ser Gln Leu
65                  70                  75                  80

Asn Lys Ala Asp Phe Tyr Lys Asp Ala His Gly Lys Met Tyr Phe
                85                  90                  95

Thr Glu Trp Asp Ser Tyr Leu Met Asp Met Thr Ser Gln His Tyr Gln
            100                 105                 110

Lys Leu Leu Glu Glu Ile Gln Lys Gln Ile Val Gln Lys Gly Leu
        115                 120                 125

Asp Gly Val Phe Leu Asp Thr Val Gly Asn Ile Asn Ser Tyr Leu Pro
    130                 135                 140

Glu Lys Glu Gln Glu Ala Gln Asn Glu Ala Met Leu Ser Phe Ile Lys
145                 150                 155                 160

Lys Ile Lys Gln Gln Tyr Asn Gly Leu Ser Val Ala Gln Asn Trp Gly
                165                 170                 175

Phe Gln Thr Leu Ala Asp Tyr Thr Ala Pro Tyr Ile Asp Phe Ile Met
            180                 185                 190

Trp Glu Asn Phe Ser Tyr Asp Val Val Gly Glu Asp Trp Ala Leu
        195                 200                 205

Asp Arg Met Lys Gln Leu Val His Ile Arg Asp Lys Phe Gly Thr Gln
    210                 215                 220

Val Met Ala Ile Gly Phe Glu Asp Glu Lys Ser Arg Ala Leu Ala
225                 230                 235                 240

Glu Lys Tyr Gln Phe Lys Phe Phe Tyr Ser Pro Ala Gly Ser His Tyr
                245                 250                 255

Asn Thr Trp Gln
            260

<210> SEQ ID NO 108
<211> LENGTH: 275
<212> TYPE: PRT
<213> ORGANISM: Tumebacillus ginsengisoli

<400> SEQUENCE: 108

Gln Val Lys Trp Gln Val Asn Tyr Ala Leu Ser Thr Glu Lys Ala Val
1               5                   10                  15

Lys Ser Val Ser His Lys Ala Ser Ser Leu Ser Ala Val Lys Ser Phe
            20                  25                  30

Met Ile Tyr Tyr Gly Asp Ala Ser Asp Ser Ala Ile Lys Lys Leu Ser
        35                  40                  45

Gln Tyr Gln Leu Val Ile Ile Glu Pro Arg Asn Trp Asn Gly Thr Glu
    50                  55                  60

Leu Ala Gln Leu Lys Lys Ser Gly Val Lys Val Leu Gly Tyr Leu Ser
65                  70                  75                  80
```

Val Leu Glu Gln Asn Ser Asn Ser Ser Leu Leu Gly Gln Val Gln Asn
            85                  90                  95

Ala Asp Tyr Leu Leu Ile Asn Gly Lys Arg Asp Pro Arg Ser Asp Trp
            100                 105                 110

Asp Ser Trp Ser Met Asn Ile Asn Ser Gly His Tyr Arg Asp Leu Leu
            115                 120                 125

Phe Ala Asp Tyr Gln Lys Glu Ile Val Asn Lys Gly Leu Asp Gly Val
            130                 135                 140

Phe Leu Asp Thr Met Gly Asp Ala Asp Gly Ile Trp Asn Thr Ser
145                 150                 155                 160

Ile Ser Asp Ser Gln Arg Asp Gly Ala Val Lys Phe Val Ala Asp Leu
            165                 170                 175

Arg Asn Lys Tyr Pro Ser Leu Ser Ile Met Gln Asn Trp Gly Leu Gln
            180                 185                 190

Gln Leu Lys Asp Arg Thr Ala Pro Tyr Ile Asp Gly Ile Leu Trp Glu
            195                 200                 205

Asp Phe Thr Pro Lys Thr Val Val Lys Asn Ala Trp Ser Lys Ser Arg
            210                 215                 220

Met Gln Glu Leu Asp Lys Leu His Ala Ala Asn Gly Leu Ser Val Phe
225                 230                 235                 240

Thr Ser His Val Gly Leu Ser Gly Ala Gln Lys Ser Lys Phe Asp Ser
            245                 250                 255

Leu Asn Val Glu His Gly Tyr Val Gly Gln Val Ile Lys Lys Ser Tyr
            260                 265                 270

Asp Val Ile
        275

<210> SEQ ID NO 109
<211> LENGTH: 268
<212> TYPE: PRT
<213> ORGANISM: Lysinibacillus boronitolerans

<400> SEQUENCE: 109

Ser Thr Ser Ile Gln Ala Lys Leu Ala Asp Val Lys Asp Tyr Thr Tyr
1               5                   10                  15

Tyr Leu Asp Lys Gly Asn Asp Ala Ile Gly Lys Ser Met Thr Lys Leu
            20                  25                  30

Asp Leu Val Ile Val Glu Pro Ile Glu Met Gln Gln Lys Tyr Ile Ile
            35                  40                  45

Asn Ala Gln Lys Ser Gly Thr Leu Val Tyr Gly Tyr Ile Asn Ala Met
        50                  55                  60

Glu Ala Asp Lys Trp Asn Thr Ala Leu Tyr His Gln Leu Lys Glu Glu
65                  70                  75                  80

Asp Phe Tyr Arg Asp Lys Gln Gly Glu Arg Met Tyr Phe Ala Lys Trp
            85                  90                  95

Asp Ser Phe Leu Met Asp Leu Ser Thr His Tyr Gln Asp Ile Leu
            100                 105                 110

Leu Ala Glu Ile Gln Gln Gln Ile Val Glu Lys Gly Leu Asp Gly Val
            115                 120                 125

Phe Leu Asp Thr Val Gly Asn Ile Asn Ser Tyr Leu Pro Glu Asp Glu
            130                 135                 140

Gln Lys Trp Gln Asn Glu Ala Ile Leu Ser Phe Ile Gln Gln Ile Lys
145                 150                 155                 160

Lys Arg His Pro Asp Leu Ser Val Ala Gln Asn Trp Gly Phe Gln Thr

```
                    165                 170                 175
Leu Ala Asp Tyr Thr Ala Pro Tyr Val Asp Phe Ile Met Trp Glu Asp
                180                 185                 190

Phe Ser Tyr Pro Val Val Gly Lys Asp Glu Trp Ser Leu Asp Met Met
            195                 200                 205

Gln Gln Leu Ile His Ile Arg Asn Lys Phe Gly Thr Gln Val Met Thr
        210                 215                 220

Ile Gly Phe Glu Glu Ser Lys Ser Arg Ala Leu Ala Glu Lys His
225                 230                 235                 240

His Phe Lys Phe Phe Tyr Ser Pro Ala Gly Ser Tyr Tyr Asn Ser Trp
                245                 250                 255

Gln Ser Ser Leu Leu Pro Ser Asp Lys Gln Leu Phe
            260                 265

<210> SEQ ID NO 110
<211> LENGTH: 313
<212> TYPE: PRT
<213> ORGANISM: Microbulbifer hydrolyticus

<400> SEQUENCE: 110

Cys Asn Leu Glu Asp Val Pro Asn Leu Tyr Pro Glu Gln Gly His Thr
1               5                   10                  15

Asp His Pro Gln Glu Met Arg Asp Phe Val Thr Gly Ile Arg Gly Tyr
            20                  25                  30

Ala Arg Gly Leu Lys Ser Gly Phe Val Val Gly His Gly Ala Leu
        35                  40                  45

Pro Leu Val Ser Ser Asn Glu Arg Thr Ser Gly Asp Pro Asp Ser Val
50                  55                  60

Tyr Ile Gly Asn Leu Asp Ala Leu Ala Gln Asp Ser Leu Phe Tyr Gly
65                  70                  75                  80

His Glu Gly Ile Asp Gln Pro Thr Thr Asp Ser Arg Arg Thr Ser Leu
                85                  90                  95

Arg Ser Tyr Leu Asp Met Ala Arg Asp Thr Gly Asn Thr Thr Ile Leu
            100                 105                 110

Ile Thr Asp Phe Ala Val Ser Glu Gln Lys Ile Asp Asn Ala Tyr Gln
        115                 120                 125

Leu Asn Asp Asp Ala Gly Tyr Leu Gly Phe Val Ala Asp His Thr Glu
130                 135                 140

Leu Asp Asn Ile Pro Ile Tyr Pro Ala Glu Pro Phe Ser Val Asn Arg
145                 150                 155                 160

Arg Asp Ile Phe Asp Leu Asp Ala Ser Asn Phe Leu Val Leu Thr
                165                 170                 175

Asn Thr Gln Leu Tyr Ser Thr Arg Gln Asp Leu Val Asp Val Ala
            180                 185                 190

Asp Thr Asp Tyr Asp Leu Ile Val Leu Asp Phe Phe Asn Gly Glu
        195                 200                 205

Glu Phe Thr Ala Gln Gln Val Arg Gln Leu Gln Arg Lys Arg Asn Gly
        210                 215                 220

Arg Thr Arg Gln Val Leu Ala Thr Val Asn Ile Gly His Ala Glu Ser
225                 230                 235                 240

Asn Arg Tyr Tyr Trp Glu Asn His Trp Val Ser Asn Pro Pro Ser Trp
                245                 250                 255

Leu Arg Glu Glu Ile Ser Gly Ser Asn Gly Asp Tyr Tyr Val Asn Tyr
            260                 265                 270
```

```
Trp Asn Pro Ala Trp Gln Asp Ile Ile Tyr Gly Lys Asn Gly Ser Tyr
            275                 280                 285

Ile Glu Lys Ile Ala Asn Ala Gly Phe Asp Gly Ala Tyr Leu Gln Gly
        290                 295                 300

Leu Asp Ala Tyr Ala His Phe Gln Asn
305                 310

<210> SEQ ID NO 111
<211> LENGTH: 257
<212> TYPE: PRT
<213> ORGANISM: Carnobacterium inhibens subsp.

<400> SEQUENCE: 111

Glu Gly Lys Ser Asn Ser Lys Leu Glu Asn Thr Gly Glu Tyr Gly Val
1               5                   10                  15

Phe Leu Ser Leu Asp Gly Ser Glu Ala Ile Glu Ala Ser Glu Gly Tyr
            20                  25                  30

Glu Thr Val Ile Ile Asp Ala Gln Asn Leu Ser Glu Ala Glu Ile Thr
        35                  40                  45

Glu Met Gln Asp Arg Gly Gln Lys Val Tyr Ser Tyr Leu Asn Val Gly
    50                  55                  60

Ser Leu Glu Thr Tyr Arg Pro Tyr Tyr Glu Glu Phe Gln Tyr Leu Thr
65                  70                  75                  80

Leu Arg Pro Tyr Glu Asn Trp Glu Glu Glu Tyr Trp Val Asp Val Thr
                85                  90                  95

Asn Glu Asp Trp Gln Lys Phe Ser Ala Val Thr Leu Ala Asn Glu Leu
            100                 105                 110

Leu Asp Lys Gly Ile Asp Gly Phe Trp Ile Asp Asn Val Asp Val Tyr
        115                 120                 125

Trp Gln Phe Gln Thr Lys Glu Thr Tyr Ile Gly Val Glu Lys Ile Leu
    130                 135                 140

Lys Thr Leu Met Ser Tyr Gly Lys Pro Val Leu Ile Asn Gly Gly Asn
145                 150                 155                 160

Glu Phe Val Ser Ala Tyr Leu Gln Gln Asn Gln Gln Leu Asp Asp Ile
                165                 170                 175

Leu Thr Gly Val Asn Gln Glu Thr Val Phe Ser Ala Ile Asp Phe Glu
            180                 185                 190

Glu Asp Lys Leu Ser Thr Gln Thr Lys Glu Asn Gln Thr Tyr Tyr Leu
        195                 200                 205

Asn Tyr Leu Asp Thr Val Asp Lys Ala Gly Lys Glu Ile Tyr Leu Leu
    210                 215                 220

Glu Tyr Ser Thr Lys Lys Glu Leu Ala Lys Asp Val His Asp Tyr Ala
225                 230                 235                 240

Thr Lys Arg Gly Trp Gln Tyr Tyr Ile Ser Asp Ser Val Glu Leu Asp
                245                 250                 255

Asn

<210> SEQ ID NO 112
<211> LENGTH: 296
<212> TYPE: PRT
<213> ORGANISM: environmental bacterial community

<400> SEQUENCE: 112

Thr Gln Val Val Ser Asn Gln Lys Asp Thr Ser Lys Lys Met Gln Asp
1               5                   10                  15

Phe Val Ile Asn Ile Ser Lys Tyr Ala Arg Lys Phe Asp Ala Asp Phe
```

20                  25                  30
Ile Ile Ile Pro Gln Asn Gly Glu Glu Leu Ala Phe Ile Gly Ala Asn
            35                  40                  45

Pro Asp Lys Lys Leu Asn Thr Thr Phe Leu Asn Ala Ile Asn Gly Phe
     50                  55                  60

Gly Ile Glu Glu Leu Phe Tyr Asn Glu Thr Phe Lys Pro Asn Glu Tyr
 65                  70                  75                  80

Arg Ile Gly Leu Leu Gln Lys Ile Lys Asp Gln Lys Thr Ile Leu Val
                 85                  90                  95

Ser Glu Tyr Val Asn Asp Thr Thr Ile Val Asn Asp Ala His Asn Lys
            100                 105                 110

Asn Ser Asn Glu Gly Phe Ile Ser Phe Ile Arg Thr Lys Asp Asn Tyr
        115                 120                 125

His Tyr Ser Ile Ile Pro Lys Lys Ile Asn Asn Glu Asn Ser Glu Asn
    130                 135                 140

Ile Thr Ser Leu Lys Asp Val Lys Asn Phe Leu Tyr Leu Ile Asn Asn
145                 150                 155                 160

Ser Asn Phe Tyr Ser Lys Ser Gly Phe Leu Glu Ala Ile Ser Asn Thr
                165                 170                 175

Asn Tyr Asp Leu Ile Phe Ile Asp Leu Tyr His Asn Gly Val Leu Phe
            180                 185                 190

Lys Lys Glu Glu Ile Glu Arg Leu Lys Gln Lys Lys Asn Gly Gly Lys
        195                 200                 205

Arg Leu Val Val Cys Tyr Met Asn Ile Gly Ala Ala Glu Lys Tyr Arg
    210                 215                 220

Asn Tyr Trp Lys Arg Asp Trp Thr Leu Gly Asn Pro Ser Trp Leu Lys
225                 230                 235                 240

Lys Lys Tyr Asp Gly Tyr Asp Gln Glu Val Trp Val Glu Phe Trp Asn
                245                 250                 255

Lys Asp Trp Gln Lys Ile Val Tyr Gly Asn Asp Gln Ser Tyr Leu Ala
            260                 265                 270

Lys Ile Leu Glu Ala Gly Tyr Asp Gly Ala Tyr Leu Asp Asn Val Glu
        275                 280                 285

Ala Tyr Tyr Phe Leu Tyr Asn Asp
    290                 295

<210> SEQ ID NO 113
<211> LENGTH: 897
<212> TYPE: PRT
<213> ORGANISM: Pseudomonas composti

<400> SEQUENCE: 113

Gln Pro Ala Ser Val Ala Phe Trp Tyr Ala Asp Gln Leu Pro Leu Pro
1               5                   10                  15

Glu Leu Ser Gln Phe Glu Trp Val Val Val Glu Pro Asp His Val Ser
            20                  25                  30

Pro Gly Asp Leu Ala Tyr Leu Gln Lys Gln Gly Ser Glu Val Phe Ala
        35                  40                  45

Tyr Leu Ser Ile Gly Glu Phe Ala Gly Asp Val Ala Gln Ala Gly Leu
    50                  55                  60

Ser Glu Ala Thr Ser Val Val Arg Asn Asp Ala Trp Asn Ser Gln Val
65                  70                  75                  80

Met Asn Leu Ala Ser Pro Val Trp Arg Glu His Leu Phe Lys Arg Thr
                85                  90                  95

-continued

Ser Thr Leu Arg Gln Gln Gly Tyr Thr Gly Leu Phe Leu Asp Thr Leu
                100                 105                 110

Asp Ser Phe Gln Leu Gln Ala Gln Asp Leu Gln Gly Ser Gln Arg Glu
            115                 120                 125

Ala Leu Lys Ser Leu Leu Ser Glu Leu His Arg Arg Glu Pro Thr Leu
        130                 135                 140

Lys Leu Phe Phe Asn Arg Gly Phe Glu Val Leu Pro Glu Leu Pro Gly
145                 150                 155                 160

Val Ala Ser Ala Val Ala Val Glu Ser Ile Tyr Ala Gly Trp Asp Ala
                165                 170                 175

Gly Gly Gly Tyr Lys Glu Val Ser Gln Gly Asp Arg Asp Trp Leu Leu
            180                 185                 190

Pro Arg Leu Asp Ala Val Arg Lys Gln Gly Val Pro Val Val Ala Ile
        195                 200                 205

Glu Tyr Leu Pro Pro Glu Gln Arg Glu Gln Ala Arg Lys Leu Ala Thr
    210                 215                 220

Arg Leu Thr Gln Glu Gly Phe Ile Pro Tyr Val Thr Ser Pro Ala Leu
225                 230                 235                 240

Asp Ala Ile Gly Val Gly Gly Val Glu Val Gln Pro Arg Arg Ile Ala
                245                 250                 255

Leu Val Tyr Asp Ala Arg Glu Gly Glu Leu Glu Asp Asn Pro Gly His
            260                 265                 270

Val His Leu Gly Gly Leu Leu Glu Tyr Leu Gly Tyr Arg Val Asp Tyr
        275                 280                 285

Trp Pro Ala Asp Thr Thr Leu Pro Gln Arg Pro Leu Lys Gly Leu Tyr
    290                 295                 300

Ala Gly Ile Val Val Trp Met Thr Ser Gly Ser Pro Val Asp Arg Asp
305                 310                 315                 320

Tyr Phe Glu Asn Trp Leu Gly Gln Arg Leu Asp Glu Gln Val Pro Leu
                325                 330                 335

Ala Phe Met Ala Gly Met Pro Thr Glu Asn Asp Ser Leu Leu Asp Arg
            340                 345                 350

Leu Gly Ile Arg Thr Arg Ser Gln Pro Val Gly Lys Asp Ala Val Leu
        355                 360                 365

Leu Ser His Asp Ala Ala Leu Ile Gly Gly Phe Glu Ala Pro Leu Arg
    370                 375                 380

Leu Arg Thr Arg Asp Val Pro Pro Leu Thr Val Thr Ala Pro Glu Arg
385                 390                 395                 400

Thr Gln Ala Ala Leu Ser Leu Gln Ser Asp Asp Arg Val Tyr Val Pro
                405                 410                 415

Val Ala Thr Gly Asp Trp Gly Gly Tyr Ala Leu Ala Pro Tyr Val Phe
            420                 425                 430

Glu Glu Gly Leu Asp His Arg Arg Trp Val Leu Asp Pro Phe Ala Phe
        435                 440                 445

Ile Ser Arg Ala Phe Lys Leu Pro Ala Leu Pro Arg Pro Asp Thr Thr
    450                 455                 460

Thr Glu Asn Gly Arg Arg Ile Ala Thr Val His Leu Asp Gly Asp Gly
465                 470                 475                 480

Phe Val Ser Arg Ala Glu Val Pro Gly Ser Pro Tyr Ser Gly Ile Gln
                485                 490                 495

Val Leu Glu Asp Phe Ile Lys Pro Tyr Pro Leu Leu Thr Ser Val Ser
            500                 505                 510

Val Ile Glu Gly Glu Val Gly Pro Arg Gly Met Tyr Pro His Leu Ser 515                 520                 525

Arg Glu Leu Glu Pro Ile Ala Arg Glu Ile Phe Val Asn Pro Lys Val
    530                 535                 540

Glu Val Ala Ser His Thr Phe Ser His Pro Phe Phe Trp Gln Pro Glu
545                 550                 555                 560

Lys Ala Thr Lys Arg Glu Asn Phe Glu Ala Glu Tyr Gly Tyr Met Met
                565                 570                 575

Ala Ile Pro Gly Tyr Lys Thr Leu Asp Met Gln Arg Glu Val Val Gly
            580                 585                 590

Ala Arg Asp Tyr Ile Asn Gln Arg Leu Thr Thr Pro Lys Lys Pro Val
        595                 600                 605

Lys Met Ile Phe Trp Ser Gly Asp Ala Met Pro Ser Ala Glu Thr Ile
    610                 615                 620

Lys Leu Ala Tyr Asp Ser Gly Leu Pro Asn Val Asn Gly Gly Asn Thr
625                 630                 635                 640

Val Leu Thr Lys Ala Tyr Pro Ser Leu Thr Gly Leu Tyr Pro Leu Ile
                645                 650                 655

Arg Pro Thr Thr Gly Gly Leu His Phe Tyr Ala Pro Val Ile Asn Glu
            660                 665                 670

Asn Val Tyr Thr Asn Leu Trp Thr Gly Pro Tyr Tyr Gly Phe Arg Asp
        675                 680                 685

Val Gln Asp Thr Phe Ala Leu Thr Asp Ser Pro Arg Arg Leu Arg Gly
    690                 695                 700

Phe His Leu Tyr Tyr His Phe Tyr Ser Gly Thr Lys Gln Ala Ser Ile
705                 710                 715                 720

Arg Ala Met Arg Gln Ile Tyr Gln Thr Ile Leu Asp Gly Gln Pro Leu
                725                 730                 735

Ser Leu Trp Met Ser Asp Tyr Ile Lys Arg Val Glu Gly Leu Tyr Arg
            740                 745                 750

Ala Ser Leu Ala Arg Arg Ser Asp Gly Thr Trp Gln Val Lys Gly Leu
        755                 760                 765

Val Gly Met Arg Thr Leu Arg Leu Asp Pro Ser Leu Gly Trp Pro Asp
    770                 775                 780

Leu Ala Arg Ser Gln Gly Val Ala Gly Val Arg Asp Leu Ala Gln Gly
785                 790                 795                 800

Arg Tyr Val His Leu Thr Gly Ala Asp Ala Val Leu Ala Leu Arg Glu
                805                 810                 815

Thr Arg Asp Pro Arg Pro Ala Leu Glu Glu Ala Asn Ile Pro Leu Thr
            820                 825                 830

Gly Trp Arg Tyr Leu Asp Asp Lys Arg Val Thr Phe Ser Phe Leu Gly
        835                 840                 845

Glu Phe Pro Leu Ser Phe Ser Val Arg Ser Ala Gly Ala Cys His Val
    850                 855                 860

Thr Ala Gly Gly Gly Arg Phe Ser Gly Thr His Asp Asn Gly Val Trp
865                 870                 875                 880

His Phe Glu Leu Pro Met Lys Gln Val Ser Asp Ala Gln Leu Val Cys
                885                 890                 895

Asn

<210> SEQ ID NO 114
<211> LENGTH: 271
<212> TYPE: PRT
<213> ORGANISM: Paraburkholderia phenazinium

<400> SEQUENCE: 114

Gln Thr Ala Ala Asp Ala Ala Ser Asn Ala Ser Ala Thr Asn Ala
1               5                   10                  15

Ser Ala Gln Pro Ser Val Ala Phe Phe Tyr Gly Gly Gln Val Pro Ala
            20                  25                  30

Ala Ala Leu Ser Glu Phe Asp Ala Val Val Glu Pro Asp Ser Gly
        35                  40                  45

Phe Asp Pro Glu Ala Gln His Gly Gly His Thr Ala Trp Phe Ala Tyr
50                  55                  60

Val Ser Val Gly Glu Val Thr Pro Gln Arg Pro Tyr Tyr Ala Ala Met
65                  70                  75                  80

Pro Lys Glu Trp Leu Val Gly His Asn Ala Ala Trp Glu Ser Lys Val
                85                  90                  95

Val Asp Gln Asp Ala Pro Gly Trp Pro Ala Phe Tyr Leu Lys Gln Val
            100                 105                 110

Ile Ala Pro Leu Trp Arg Lys Gly Tyr Arg Gly Phe Phe Leu Asp Thr
        115                 120                 125

Leu Asp Ser Tyr Gln Leu Ile Ala Lys Thr Asp Ala Asp Arg Gln Arg
130                 135                 140

Gln Gln Ala Gly Leu Val Ala Val Ile Arg Ala Ile Lys Ala Arg Tyr
145                 150                 155                 160

Pro Arg Ala Met Leu Met Phe Asn Arg Gly Phe Glu Ile Leu Pro Gln
                165                 170                 175

Val His Glu Leu Val Tyr Ala Val Ala Phe Glu Ser Leu Tyr Ser Gly
            180                 185                 190

Trp Asp Gln Thr Lys Gln Ser Tyr Thr Gln Val Pro Leu Ala Asp Arg
        195                 200                 205

Asp Trp Leu Leu Gly Gln Ala Arg Ile Ile Arg Glu Gly Tyr Arg Leu
210                 215                 220

Pro Val Ile Ser Ile Asp Tyr Cys Ala Pro Gly Asp Glu Gln Cys Ala
225                 230                 235                 240

Arg Asp Thr Val Gln Lys Ile Cys Lys Asp Gly Leu Val Pro Tyr Val
                245                 250                 255

Thr Asp Gly Ala Leu Gln Thr Val Gly Val Gly Arg Ala Gly Arg
            260                 265                 270

<210> SEQ ID NO 115
<211> LENGTH: 266
<212> TYPE: PRT
<213> ORGANISM: Burkholderia sp-63093

<400> SEQUENCE: 115

Gln Gly Pro Ala Asp Met Pro Ala Gly Pro Ser Val Ala Leu Tyr Tyr
1               5                   10                  15

Gly Ala Asn Pro Pro Val Glu Glu Leu Ala Thr Phe Asp Val Val
            20                  25                  30

Val Asp Pro Asp Ala His Phe Asp Pro Arg Ala His Ala Lys Ala His
        35                  40                  45

Pro Val Trp Phe Ala Tyr Val Ser Val Gly Glu Val Asn Pro His Arg
50                  55                  60

Ala Tyr Tyr Ser Ala Met Pro Ser Ala Trp Leu Pro Gly Val Asn Asp
65                  70                  75                  80

Ala Trp Ala Ser His Val Ile Asp Gln Thr Ala Ala Glu Trp Pro Ala
                85                  90                  95

-continued

```
Phe Phe Val Asp Lys Val Ile Ala Pro Leu Trp Lys Lys Gly Tyr Arg
            100             105             110

Gly Phe Phe Leu Asp Thr Leu Asp Ser Tyr His Leu Ile Ala Lys Thr
        115             120             125

Asp Ala Ala Arg Ala Ala Gln Glu Ala Gly Leu Val Arg Val Ile Arg
    130             135             140

Ala Ile Lys Lys Arg Tyr Pro Lys Ala Lys Leu Ile Phe Asn Arg Gly
145             150             155             160

Phe Glu Val Leu Pro Gln Ile His Asp Leu Ala Tyr Met Val Ala Phe
                165             170             175

Glu Ser Leu Tyr Arg Gly Trp Asp Ala Gly Lys Gln Arg Tyr Thr Glu
            180             185             190

Val Pro Gln Ala Asp Arg Asp Trp Leu Leu Met Gln Ala Ala Thr Ile
        195             200             205

Arg Asp Gln Tyr Lys Leu Pro Val Leu Ser Ile Asp Tyr Cys Pro Pro
    210             215             220

Ala Asp Asp Thr Cys Ala Ala Ala Thr Ala Ala Arg Ile Thr Gln Ala
225             230             235             240

Gly Phe Val Pro Tyr Val Thr Asp Gly Gly Leu Ala Thr Val Gly Val
                245             250             255

Gly Ala Ala Gly Thr Gly Asn Glu Arg Pro
            260             265
```